(12) United States Patent
Yadidi

(10) Patent No.: US 12,343,425 B2
(45) Date of Patent: *Jul. 1, 2025

(54) DRY POWDER FORMULATIONS FOR INHALATION

(71) Applicant: Aspeya US Inc., Stamford, CT (US)

(72) Inventor: Kambiz Yadidi, Los Angeles, CA (US)

(73) Assignee: Aspeya US Inc., Stamford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/161,988

(22) Filed: Jan. 31, 2023

(65) Prior Publication Data

US 2023/0277450 A1 Sep. 7, 2023

Related U.S. Application Data

(63) Continuation of application No. 16/988,559, filed on Aug. 7, 2020, now Pat. No. 11,596,603, which is a continuation of application No. 15/798,079, filed on Oct. 30, 2017, now Pat. No. 10,772,832, which is a continuation of application No. PCT/US2016/030035, filed on Apr. 29, 2016.

(60) Provisional application No. 62/154,784, filed on Apr. 30, 2015.

(51) Int. Cl.

| | | |
|---|---|---|
| A61K 9/00 | (2006.01) |
| A61K 9/16 | (2006.01) |
| A61K 31/4365 | (2006.01) |
| A61K 31/616 | (2006.01) |
| A61K 47/24 | (2006.01) |
| A61P 7/02 | (2006.01) |
| A61P 9/10 | (2006.01) |

(52) U.S. Cl.
CPC .......... *A61K 9/0075* (2013.01); *A61K 9/1623* (2013.01); *A61K 9/1652* (2013.01); *A61K 31/4365* (2013.01); *A61K 31/616* (2013.01); *A61K 47/24* (2013.01); *A61P 7/02* (2018.01); *A61P 9/10* (2018.01)

(58) Field of Classification Search
CPC .. A61K 9/0075; A61K 9/1623; A61K 9/1652; A61K 31/4365; A61K 31/616; A61K 47/24; A61P 7/02; A61P 9/10
See application file for complete search history.

(56) References Cited

U.S. PATENT DOCUMENTS

| | | |
|---|---|---|
| 6,258,341 B1 | 7/2001 | Foster et al. |
| 10,772,832 B2 | 9/2020 | Yadidi et al. |
| 2004/0184995 A1 | 9/2004 | Katsuma et al. |
| 2006/0293273 A1 | 12/2006 | Mangano |
| 2010/0258118 A1 * | 10/2010 | Morton ............. A61M 15/0078 264/9 |
| 2014/0065219 A1 | 3/2014 | Bosch et al. |

FOREIGN PATENT DOCUMENTS

| | | |
|---|---|---|
| WO | WO2009019598 | 2/2009 |
| WO | WO2016019253 | 2/2016 |

* cited by examiner

*Primary Examiner* — Snigdha Maewall
(74) *Attorney, Agent, or Firm* — Oblon, McClelland, Maier & Neustadt, L.L.P.

(57) ABSTRACT

A respirable dry powder including acetylsalicylic acid in particles has a mass median aerodynamic diameter (MMAD) within a range of about 0.5 μm to about 10 μm. The respirable dry powder may contain a pharmaceutically acceptable excipient, such as a phospholipid, in an amount ranging from about 0.1% (w/w) to about 10% (w/w) of the particles.

16 Claims, 13 Drawing Sheets

| Sample | Approach | D(v 0.1) μm | D(v 0.5) μm | D(v 0.9) μm | D[3,2] μm | D[4,3] μm | Span |
|---|---|---|---|---|---|---|---|
| BREC-1511-024 (T = 0) | Jet Milled ASA Control | 0.6 | 1.5 | 3.0 | 1.2 | 1.7 | 1.597 |
| BREC-1511-024 (T = 1wk) | | 0.8 | 2.1 | 4.3 | 1.5 | 2.4 | 1.700 |
| BREC-1511-024 (T = 2wk) | | 0.8 | 2.2 | 4.6 | 1.5 | 2.5 | 1.747 |
| BREC-1511-024 (T = 4wk) | | 0.8 | 2.4 | 5.2 | 1.6 | 2.7 | 1.820 |
| BREC-1511-038A (T = 0) | Milled ASA Suspended in Hexane | 0.9 | 2.3 | 4.5 | 1.6 | 2.5 | 1.592 |
| BREC-1511-038A (T = 1wk) | | 0.9 | 2.2 | 4.4 | 1.7 | 2.5 | 1.544 |
| BREC-1511-038A (T = 2wk) | | 0.9 | 2.3 | 4.4 | 1.7 | 2.5 | 1.557 |
| BREC-1511-038A (T = 4wk) | | 0.9 | 2.3 | 4.6 | 1.7 | 2.6 | 1.545 |
| BREC-1511-038B (T = 0) | Milled ASA Suspended in Hexane with Lecithin | 0.9 | 2.0 | 3.9 | 1.6 | 2.2 | 1.487 |
| BREC-1511-038B (T = 1wk) | | 0.8 | 2.1 | 4.1 | 1.5 | 2.3 | 1.579 |
| BREC-1511-038B (T = 2wk) | | 0.8 | 2.1 | 4.2 | 1.6 | 2.4 | 1.574 |
| BREC-1511-038B (T = 4wk) | | 1.0 | 2.4 | 4.6 | 1.7 | 2.6 | 1.536 |

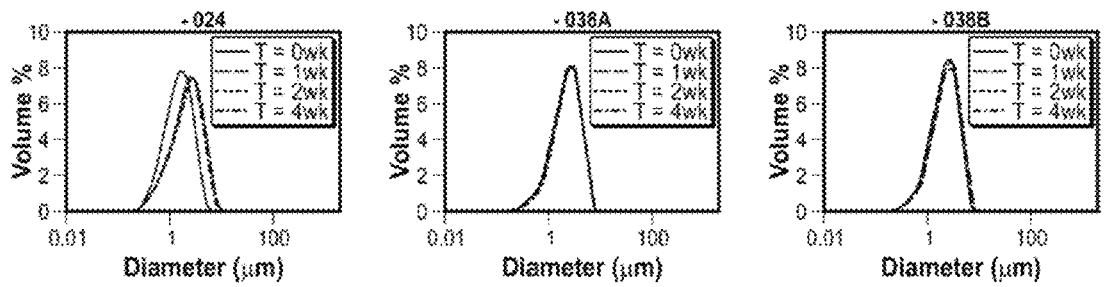

Figure 8

| Lot Number | Formulation | Time Point | Mass Median Aerodynamic Diameter (MMAD) (μm) | Geometric Standard Deviation (GSD) | Emitted Fraction (EF) (%) | Fine Particle Fraction (FPF) <5um (%) | Fine Particle Dose (mgA) |
|---|---|---|---|---|---|---|---|
| BREC1511-024 | Jet Milled ASA (Control) | Initial | 3.66±0.23 | 1.77±0.06 | 74.1±18.3 | 60.9±6.3 | 16.5±2.9 |
| | | 4 week | 6.00±0.10 | 1.87±0.01 | 87.4±1.2 | 22.1±1.4 | 7.2±0.4 |

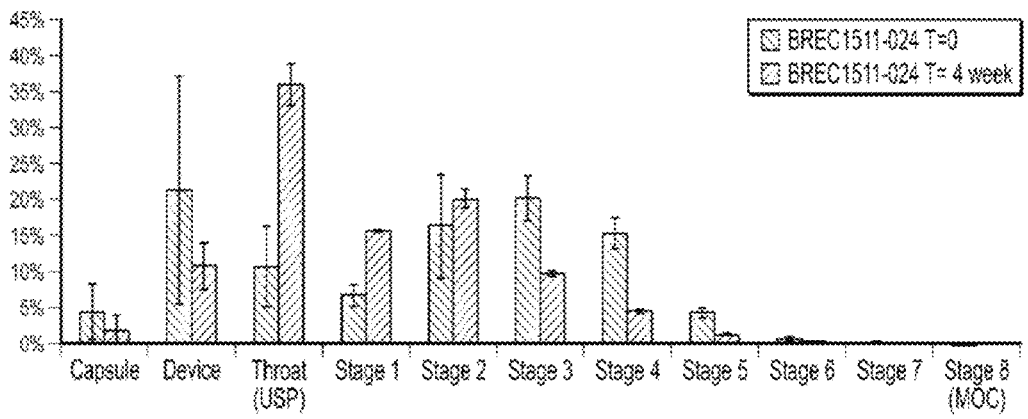

Fig. 9

| Lot Number | Formulation | Time Point | Mass Median Aerodynamic Diameter (MMAD) (μm) | Geometric Standard Deviation (GSD) | Emitted Fraction (EF) (%) | Fine Particle Fraction (FPF) <5um (%) | Fine Particle Dose (mgA) |
|---|---|---|---|---|---|---|---|
| BREC1511-024 | Jet Milled ASA (Control) | Initial | 3.66±0.23 | 1.77±0.06 | 74.1±18.3 | 60.9±6.3 | 12.7±0.3 |
| | | 2 week | Un-measurable | | 97.2 | 11.8 | 4.3 |

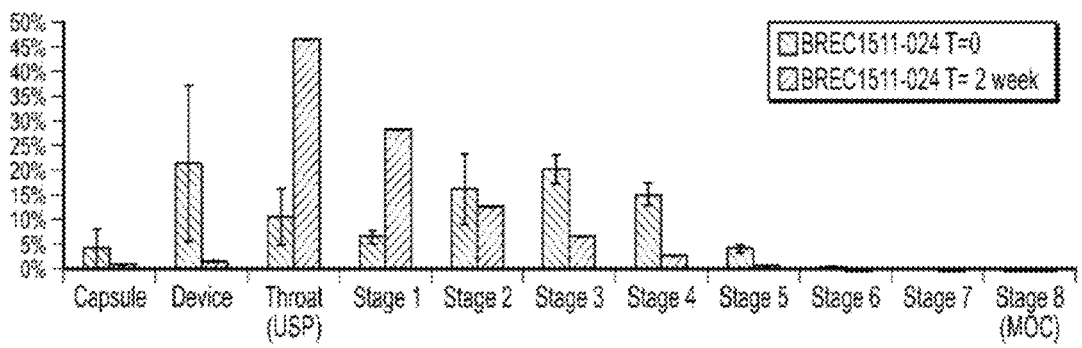

Fig. 15

| Lot Number | Formulation | Time Point | Mass Median Aerodynamic Diameter (MMAD) (μm) | Geometric Standard Deviation (GSD) | Emitted Fraction (EF) (%) | Fine Particle Fraction (FPF) <5um (%) | Fine Particle Dose (mgA) |
|---|---|---|---|---|---|---|---|
| BREC1511-038A | 100% ASA | Initial | 3.92 ± 0.13 | 1.63 ± 0.07 | 63.6 ± 12.7 | 58.8 ± 3.3 | 11.6 ± 1.1 |
| | | 2 week | 5.42 | 1.79 | 93.9 | 26.4 | 7.8 |

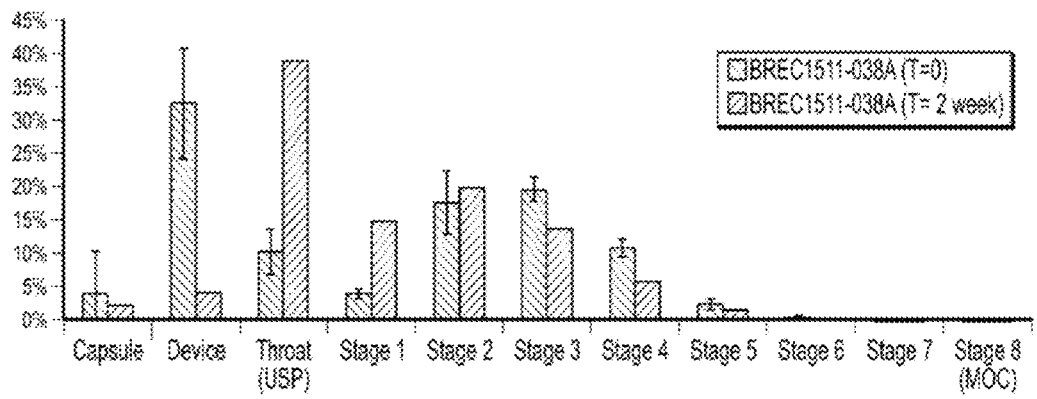

Fig. 16

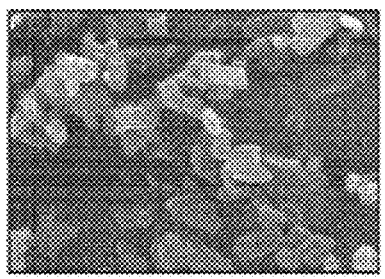
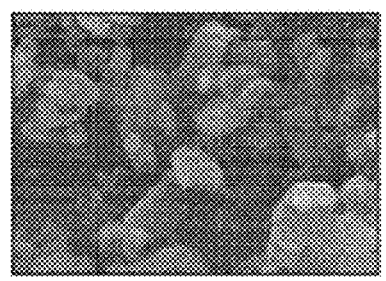
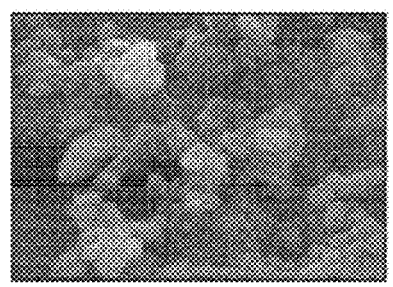
Fig. 19A  Fig. 19B  Fig. 19C
Fig. 19D  Fig. 19E

DRY POWDER FORMULATIONS FOR INHALATION

CROSS REFERENCE TO RELATED APPLICATIONS

This application is a continuation of U.S. patent application Ser. No. 16/988,559, filed on Aug. 7, 2020, which is a continuation of U.S. patent application Ser. No. 15/798,079, filed Oct. 30, 2017, now U.S. Pat. No. 10,772,832, issued Sep. 15, 2020, which is a continuation of PCT Application No. PCT/US2016/030035, filed Apr. 29, 2016, which claims priority to U.S. Provisional Application No. 62/154,784, filed Apr. 30, 2015, all of which are incorporated herein by reference in their entirety.

FIELD

The subject technology relates generally to pulmonary delivery of dry powder formulations of nonsteroidal anti-inflammatories (NSAIDs), such as aspirin or acetylsalicylic acid. The subject technology also relates generally to apparatuses and methods for delivery of substances, e.g., medication, to the lungs by inhalation for treating disease, such as ischemic or thromboembolic events, including cardiovascular disease.

BACKGROUND

Pulmonary delivery of therapeutic agents offers several advantages over other modes of delivery. These advantages include rapid onset, the convenience of patient self-administration, the potential for reduced drug side-effects, ease of delivery by inhalation, the elimination of needles, and the like. Inhalation therapy is capable of providing a drug delivery system that is easy to use in an inpatient or outpatient setting, results in very rapid onset of drug action, and produces minimal side effects.

Dry powder inhalation offers the possibility of delivering accurate and reproducible doses of a drug to the pulmonary vasculature. Telko et al. *Dry Powder Inhaler Formulation. Respiratory Care* 50(9):1209 (2005). Dry powder formulations for inhalation therapy are described in U.S. Pat. No. 5,993,805 to Sutton et al.; U.S. Pat. No. 6,921,6527 to Platz et al.: WO 0000176 to Robinson et al.; WO 9916419 to Tarara et al.; WO 0000215 to Bot et al: U.S. Pat. No. 5,855,913 to Hanes et al.; and U.S. Pat. Nos. 6,136,295 and 5,874,064 to Edwards et al.

Broad clinical application of dry powder inhalation delivery has been limited by difficulties in generating dry powders of appropriate particle size, particle density, and dispersibility, keeping the dry powder stored in a dry state and developing a convenient, hand-held device that effectively disperses the respirable dry particles to be inhaled in air. In addition, the particle size of dry powders for inhalation delivery is inherently limited by the fact that smaller respirable dry particles are harder to disperse in air. Dry powder formulations, while offering advantages over cumbersome liquid dosage forms and propellant-driven formulations, are prone to aggregation and low flowability, which considerably diminish dispersibility and the efficiency of dry powder-based inhalation therapies. For example, interparticular Van der Waals interactions and capillary condensation effects are known to contribute to aggregation of dry particles. Hickey, A. et al., *Factors Influencing the Dispersion of Dry Powders as Aerosols*, Pharmaceutical Technology, August, 1994.

To overcome such interparticle adhesive forces, Batycky et al. in U.S. Pat. No. 7,182,961 teach production of so called "aerodynamically light respirable particles," which have a volume median geometric diameter (VMGD) of greater than 5 microns (µm) as measured using a laser diffraction instrument such as HELOS (manufactured by Sympatec, Princeton, N.J.). See Batycky et al., column 7, lines 42-65. Another approach to improve dispersibility of respirable particles of average particle size of less than 10 µm, involves the addition of a water soluble polypeptide or addition of suitable excipients (including amino acid excipients such as leucine) in an amount of 50% to 99.9% by weight of the total composition. Eljamal et al., U.S. Pat. No. 6,582,729. However, this approach reduces the amount of active agent that can be delivered using a fixed amount of powder. Therefore, an increased amount of dry powder is required to achieve the intended therapeutic results, for example, multiple inhalations and/or frequent administration may be required. Still other approaches involve the use of devices that apply mechanical forces, such as pressure from compressed gasses, to the small particles to disrupt interparticular adhesion during or just prior to administration. See, e.g., U.S. Pat. No. 7,601,336 to Lewis et al., U.S. Pat. No. 6,737,044 to Dickinson et al., U.S. Pat. No. 6,546,928 to Ashurst et al., or U.S. Pat. Applications 20090208582 to Johnston et al.

Despite the advances in dry powder formulation, clinically there has been no effective dry powder formulation of acetylsalicylic acid (aspirin). Given the known effectiveness of acetylsalicylic acid for treating cardiovascular disease and more generally thromboembolic (ischemic) diseases such as stroke, there remains a need to develop dry powder formulations of acetylsalicylic acid, acetylsalicylic acid which can effectively and rapidly deliver doses to the patient in distress. Acetylsalicylic acid is an antiplatelet drug, which inhibits cyclooxygenase activity of platelet prostaglandin H synthase-1 and almost completely suppresses platelet capacity to generate the prothrombotic and proatherogenic thromboxane A2. De Caterina. *Clinical use of acetylsalicylic acid in ischemic heat disease: past, present and future*. Curr. Phar, Des. 18(33):5215-23 (2012). It has clearly been shown that antiplatelet therapy with acetylsalicylic acid reduces the risk of serious vascular events. Id. Acetylsalicylic acid has also been shown to be useful in the treatment of acute ischemic stroke as well as transient ischemic events. Zheng-Ming et al. Indications for Early Acetylsalicylic acid Use in Acute Ischemic Stroke. Stroke 31:1240-1249 (2000); Warlow Controversies in Stroke: Acetylsalicylic acid Should Be First-Line Antiplatelet Therapy in the Secondary Prevention of Stroke. Stroke 33:2137-2138 (2000). However, given the rapid first-pass metabolism of acetylsalicylic acid, there remains a need for providing novel formulations of nonsteroidal anti-inflammatory drugs ("NSAIDs"), such as acetylsalicylic acid, that are suitable for pulmonary delivery and may therefore bypass first-pass metabolism and avoid gastrointestinal side effects.

SUMMARY

The present dry powder composition comprises at least one NSAID, such as acetylsalicylic acid, as the active ingredient. The dry powder composition contains dry particles that comprise acetylsalicylic acid or a pharmaceutically acceptable salt thereof. The dry particles can be respirable. The dry particles may have a mass median aerodynamic diameter (MMAD) ranging from about 0.5 µm to about 10 µm, from about 1 µm to about 10 µm, from about 1 µm to about 5 µm, from about 3 µm to about 4 µm, from about 2 µm to about 5 µm, or about 20 µm or less. The dry particles may vary in size, e.g., with a geometric diameter (VMGD) between 0.5 µm and 30 µm.

The composition may further comprise a pharmaceutically acceptable excipient, such as one or more phospholipids, in an amount ranging from about 0.1% (w/w) to about 10% (w/w), from about 0% to about 99% (w/w), from about 0.01% to about 80% (w/w), from about 0.05% to about 70% (w/w), from about 0.1% to about 60% (w/w), from about 0.1% to about 50% (w/w), from about 0.1% to about 40% (w/w), from about 0.1% to about 30% (w/w), from about 0.1% to about 20% (w/w), from about 0.05% to about 8% (w/w), from about 0.1% to about 6% (w/w), from about 5% to about 10% (w/w), from about 3% to about 8% (w/w), from about 2% to about 6% (w/w), from about 0.1% to about 5% (w/w), from about 0.1% to about 4% (w/w), from about 0.1% to about 3% (w/w), from about 0.1% to about 2% (w/w), from about 0.1% to about 1% (w/w), from about 1% to about 6% (w/w), from about 1% to about 5% (w/w), from about 1% to about 4% (w/w), or from about 1% to about 3% (w/w), about 0.1% (w/w), about 5% (w/w), about 3% (w/w), or about 10% (w/w), of the composition.

Non-limiting examples of the phospholipids include dipalmitoyl phosphatidylcholine (DPPC), distearoyl phosphatidylcholine (DSPC), soy lecithin, or a combination thereof. In one embodiment, the weight percentage of the DSPC is 5% (w/w) of the composition. In another embodiment, soy lecithin is 0.1% (w/w) of the composition.

The dry particles may be coated with a pharmaceutically acceptable excipient, such as one or more phospholipids.

Acetylsalicylic acid, or a pharmaceutically acceptable salt thereof, may be in an amount greater than 20% (w/w), greater than 30% (w/w), greater than 40% (w/w), greater than 50% (w/w), greater than 60% (w/w), greater than 70% (w/w), greater than 80% (w/w), greater than 90% (w/w), of the composition.

The MMAD of the dry particles may vary less than about 10%, less than about 8%, less than about 6%, less than about 4%, or less than about 2%, after the dry powder composition is stored at 30° C. at 65% relative humidity for about 4 weeks, after the dry powder composition is stored at 50° C. at 75% relative humidity for about 2 weeks, or after the dry powder composition is stored at 50° C. for about 5 days.

The particles may have an MMAD size distribution where the particles exhibit: (i) a DV90 less than about 20 μm, a DV50 less than about 7 μm, and a DV10 less than about 2 μm; (ii) a DV90 less than about 10 μm, a DV50 less than about 4 μm, and a DV10 less than about 1 un: (iii) a DV90 less than about 6 μm, a DV50 less than about 3 μm, and a DV10 less than about 1 μm; (iv) a DV50 less than about 5 μm, and a DV10 less than about 2 μm; or (v) a DV50 ranging from about 2.5 μm to about 4 μm, and a DV10 ranging from about 0.8 μm to about 1.5 μm.

The DV90, DV50 and/or DV10 of the dry particles may vary less than about 10%, less than about 8%, less than about 6%, less than about 4%, or less than about 2%, after the dry powder composition is stored at 30° C. at 65% relative humidity for about 4 weeks.

The subject technology also provides a drug delivery system for treating (including prophylactic treatment or reducing the risk of) a cardiovascular disease (such as thrombosis), the system comprising the present composition. Acetylsalicylic acid may be present at a dose ranging from about 2 mg to about 80 mg, from about 5 mg to about 80 mg, from about 5 mg to about 60 mg, from about 5 mg to about 50 mg, from about 5 mg to about 40 mg, or from about 10 mg to about 40 mg.

In certain embodiments, the drug delivery system contains: a therapeutically effective dose of an NSAID (such as acetylsalicylic acid) in dry powder form; a dry powder inhaler, the dry powder inhaler comprising a mouthpiece, a reservoir for receiving the dose of the NSAID (such as acetylsalicylic acid), and an actuation member for making available the dose of the acetylsalicylic acid for inhalation by the patient through the mouthpiece. A single inhaled dose of the NSAID (such as acetylsalicylic acid) may be about 40 mg or less, or 30 mg or less. The dose of acetylsalicylic acid may be present at amounts ranging from about 5 to about 40 mg.

The formulation may further comprise clopidogrel.

In one embodiment, the pharmaceutically acceptable excipient is DSPC, the respirable dry powders substantially comprise dry particles having a MMAD ranging from about 3 to about 4 μm. The mass percent of stages in an NGI testing apparatus of the respirable powder yields may be at, stage 1 about 10% to about 13%, stage 2, about 20% to about 23%, stage 3, about 13% to about 15%, and stage 4, about 5% to about 6% and fine particle fraction ranges from about 45% to about 55%.

In another embodiment, the pharmaceutically acceptable excipient is soy lecithin, the respirable dry powders substantially comprise dry particles having a MMAD ranging from about 2.0 to about 3.0 μm. The mass percent of stages in an NGI testing apparatus of the respirable powder yields are at, stage 1 about 5% to about 10%, stage 2, about 10% to about 18%, stage 3, about 15% to about 20%, and stage 4, about 10% to about 15% and fine particle fraction ranges from about 50% to about 70%.

The composition may further comprise an excipient such as sodium lauryl sulfate (SLS), lactose, starch, cellulose, leucine, sodium citrate, maltodextrin, mannitol or a combination thereof.

In one embodiment, the particles may have a size distribution where 90% of the formulation comprises particles with an MMAD of about 6 μm or less, 50% of the formulation comprises particles having an MMAD of about 3 Jim or less, and 10% of the formulation comprises particles having an MMAD of about 1 μm or less.

The respirable dry powder compositions can include a pharmaceutically acceptable excipient, such as leucine, sodium citrate, maltodextrin or mannitol, which may be present in an amount of about 5% to about 90% or by weight.

In one embodiment, the NSAID, such as acetylsalicylic acid, is provided in a dry powder formulation comprising a mixture of particles of various sizes, for example, a mixture of (i) particles having a mean geometric diameter (VMGD) and/or mass median aerodynamic diameter (MMAD) of about 5 μm or less, and (ii) particles having a mean geometric diameter (VMGD) and/or mass median aerodynamic diameter (MMAD) of 15 μm or greater. In one embodiment, the composition may include a pharmaceutically acceptable excipient. In another embodiment, the composition is free or substantially free of excipient. In certain embodiments, the composition is free or substantially free of anti-aggregation excipient.

In another embodiment, the NSAID, such as acetylsalicylic acid, comprises dry particles having a mass median aerodynamic diameter (MMAD) within a range of about 0.5 μm to about 10 μm, wherein the dry powder further comprises one or more phospholipids in an amount ranging from about 0.1% (w/w) to about 10% (w/w) of the dry particles. The particles may have an MMAD size distribution where the particles exhibit: (i) a DV90 less than about 20 μm, a DV50 less than about 7 μm, and a DV10 less than about 2 μm; (ii) a DV90 less than about 10 μm, a DV50 less than about 4 μm, and a DV10 less than about 1 μm; or (iii) a DV90 less than about 6 μm, a DV50 less than about 3 μm, and a DV10 less than about 1 sun.

The present application also provides for methods in therapy (e.g., treatment, prophylaxis, or diagnosis). The present composition may be used for treatment (including prophylactic treatment, such as prevention or reducing the risk) of a cardiovascular disease (such thrombosis), and in the manufacture of a medicament for the treatment, prophylaxis or diagnosis of a cardiovascular or thromboembolic disease (such as thrombosis). In certain embodiments, the present application provides for a method of treating an ischemic event, reducing the risk of a thromboembolic event or treating thrombosis. The method contains administrating to a subject in need thereof a therapeutically effective dose of the present dry powder composition.

The thromboembolic event may be a myocardial infraction or a stroke. The thromboembolic event may be a transient ischemic event.

The thromboembolic event may be treated within about 5, 10 or 15 minutes of onset of an ischemic event.

BRIEF DESCRIPTION OF THE DRAWINGS

The accompanying drawings, which are included to provide further understanding of the subject technology and are incorporated in and constitute a part of this specification, illustrate aspects of the subject technology and together with the description serve to explain the principles of the subject technology.

FIG. 5A: 2 capsules were delivered to the NGI; FIG. 5B: 1 capsule was delivered to the NGI.

FIG. 6A: 2 capsules were delivered to the NGI; FIG. 6B: 1 capsule was delivered to the NGI.

FIG. 8 shows laser diffraction data of 100% jet-milled ASA (BREC-1511-024), BREC-1511-038A (spray dried from hexane, 100% ASA), spray dried from hexane 99.9/0.1 ASA/Lecithin (BREC-1511-038B) over the period of four weeks (time 0, week 1, week 2, and week 4) at 30° C. and 65% relative humidity (RH).

FIG. 9 shows the particle size distribution of BREC1511-024 particles based on NGI analysis (week 4, at 30° C. and 65% RH).

FIG. 12A: BREC1511-024 at initial time point. FIG. 12B: BREC1511-038A at initial time point. FIG. 12C: BREC1511-038B at initial time point. FIG. 12D: BREC1511-024 at 2 weeks. FIG. 12E: BREC1511-038A at 2 weeks. FIG. 12F: BREC1511-038B at 2 weeks.

FIG. 15 shows the particle size distribution of BREC1511-024 particles based on NGI analysis (after 2 weeks at 50° C./75% RH).

FIG. 16 shows the particle size distribution of BREC1511-038A particles based on NGI analysis (after 2 weeks at 50° C./75% RH).

FIGS. 19A-19E show particle morphology of BREC-1511-052A (FIG. 19A), BREC-1511-052B (FIG. 19B), BREC-1511-052C (FIG. 19C), BREC-1511-052D (FIG. 19D), and BREC-1511-052E (FIG. 19E) (images were obtained using SEM).

DETAILED DESCRIPTION

Figure 1:
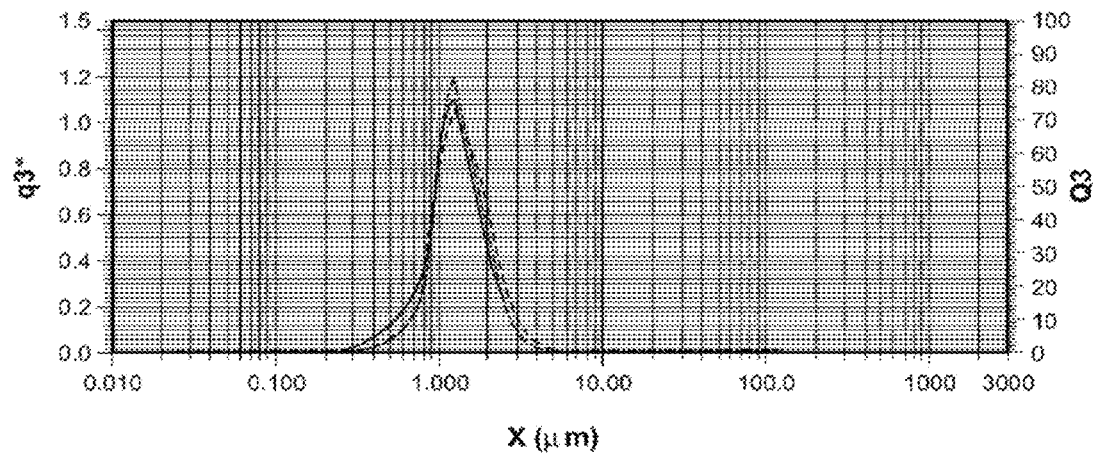
FIG. 1 shows laser diffraction data of Formulation 3727.

The present invention provides for a dry powder composition containing acetylsalicylic acid. The dry particles of the dry powder may have a mass median aerodynamic diameter (MMAD) within a range of about 0.5 μm to about 10 μm. The respirable dry powder may contain a pharmaceutically acceptable excipient, such as a phospholipid, in an amount ranging from about 0.1% (w/w) to about 10% (w/w) of the particles.

The dry particles of the present composition show stability. In certain embodiments, the MMAD of the dry particles of the present composition varies less than about 30%, less than about 25%, less than about 20%, less than about 15%, less than about 10%, less than about 9%, less than about 8%, less than about 7%, less than about 6%, less than about 5%, less than about 4%, less than about 3%, less than about 2%, or less than about 1%, after the composition is stored at 30° C. at 65% relative humidity for about 4 weeks, or stored at 50° C. at 75% relative humidity for about 2 weeks. In certain embodiments, the DV90, DV50 and/or DV10 of the dry particles of the present composition vary (varies) less than about 30%, less than about 25%, less than about 20%, less than about 15%, less than about 10%, less than about 9%, less than about 8%, less than about 7%, less than about 6%, less than about 5%, less than about 4%, less than about 3%, less than about 2%, or less than about 1%, after the composition is stored at 30° C. at 65% relative humidity for about 4 weeks, or stored at 50° C. at 75% relative humidity for about 2 weeks.

1. Introduction

Thromboembolic Symptoms and Events

A thromboembolic event, such as myocardial infarction, deep venous thrombosis, pulmonary embolism, thrombotic stroke, etc., can present with a group of symptoms that allow a patient or clinician to provide an initial therapy or treatment for the event, i.e., immediately, or within 1, 5, 10 or 15 minutes of onset of the thromboembolic event. In certain situations, an 81 mg, low dose, or "baby" acetylsalicylic acid or a regular acetylsalicylic acid (330 mg) may be orally administered in order to provide an initial treatment for the patient. However, oral administration may not act as quickly as necessary to provide a sufficient therapeutic effect and therefore, may lead to a less preferred outcome. Thus, the pulmonary drug delivery system and related methods or the present invention provide for an accelerated and more efficient pathway and treatment for reducing the risk of a thromboembolic event and/or providing treatment for a thromboembolic event. For example, certain embodiments provide systems and methods of administering a non-steroidal anti-inflammatory drug (NSAID) by inhalation, such as by a dry powder inhaler (DPI) or a metered dose inhaler (MDI).

Dry Powder Inhaler Technology

Delivery of a drug by inhalation in the early stages of an emergency situation can provide a fast-acting, effective form of preliminary treatment of certain medical conditions. For example, in one embodiment, upon receiving a complaint of a symptom of a serious thromboembolic event, a patient can be administered, by DPI, a therapeutic amount of a NSAID. The NSAID can address problems associated with or provide an initial treatment for the medical condition.

However, dry powder inhalation of drugs has generally been limited to dosages of less than a milligram. Recent developments in particle engineering, in particular the development of PulmoSphere® technology, have enabled the delivery of a larger amount of dry powder to the lungs in a single actuation. See David E. Geller, M. D., et al., Development of an inhaled dry-powder formulation of tobramycin using Pulmosphere™ technology, J Aerosol Med Pulm Drug Deliv. 2011 August; 24(4), pp. 175-82. In this publication, a dose of 112 mg tobramycin (in four capsules) was effectively delivered via PulmoSpheres®.

To date, there has been no single dose use of acetylsalicylic acid by dry powder inhaler to replace the traditional daily use of a NSAID (such as a baby acetylsalicylic acid) or emergency use of a NSAID as preventative care for symptoms of a thromboembolic event. Accordingly, in one embodiment, the methods provide for administering a NSAID by dry powder inhalation in an amount less than the dosage of a baby acetylsalicylic acid (e.g., less than 81 mg).

Therefore, a method for treating disease, e.g., by reducing the risk of a thromboembolic event, comprises administering a NSAID, such as a salicylate, by a DPI or MDI. For example, the method can comprise administering acetylsalicylic acid by a DPI or MDI. The administered dose (e.g., a single dose) can be less than 25 mg of acetylsalicylic acid. Further, in various embodiments, the administered dosage (e.g., a single dose) can be less than 20 mg of acetylsalicylic acid. The administered dosage (e.g., a single dose) can be less than 80 mg, less than 70 mg, less than 60 mg, less than 50 mg, less than 40 mg, less than 30 mg, less than 20 mg, less than 15 mg of acetylsalicylic acid, less than 12 mg of acetylsalicylic acid, less than 10 mg of acetylsalicylic acid, less than 8 mg of acetylsalicylic acid, less than 5 mg of acetylsalicylic acid, or less than 2 mg of acetylsalicylic acid.

In other embodiments, the dosage of acetylsalicylic acid (e.g., a single dose) can be from about 2 mg to about 30 mg, about 4 mg to about 25 mg of acetylsalicylic acid, about 6 mg to about 20 mg of acetylsalicylic acid, about 8 mg to about 15 mg of acetylsalicylic acid, about 10 mg to about 13 mg of acetylsalicylic acid, about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, or about 20 mg of acetylsalicylic acid. Such dosages can provide a bioequivalent dosage when compared to typical dosages of about 81 mg to about 325 mg, while demonstrating few negative side effects.

Thus, a NSAID, such as acetylsalicylic acid, can be administered by DPI or MDI in a single dose or multiple dose that delivers much less than a traditional oral dose of acetylsalicylic acid, which can provide an equivalent treatment while tending to avoid the negative side effects associated with certain NSAIDs, such as acetylsalicylic acid. Further, systems (devices) of administering such treatments are also provided.

The NSAID, in particular acetylsalicylic acid, can be formulated to include pharmaceutically acceptable excipients that are effective to improve aerodynamic performance, bioavailability and/or pharmacokinetics as compared to prior art methods of administration.

The DPI or MDI apparatus can have a mouthpiece and an actuation member for making available the NSAID for inhalation by a patient to reduce the risk of the thromboembolic event.

For example, a method of reducing the risk of a thromboembolic event is provided and can comprise administering a dose of a non-steroidal anti-inflammatory drug by a dry powder inhaler. The dose can be effective to reduce a risk of a thromboembolic event in a patient. The dry powder inhaler can have a mouthpiece and an actuation member for making available the dose of the non-steroidal anti-inflammatory drug for inhalation by the patient to reduce the risk of the thromboembolic event.

A drug delivery system can also be provided for treating a disease, for example, by reducing the risk of a thromboembolic (ischemic) event. The system can comprise a dose of a non-steroidal anti-inflammatory drug in powder form. The dose can be effective to reduce the risk of a thromboembolic event in a patient. The system can also comprise a dry powder inhaler. The dry powder inhaler can have a mouthpiece, a reservoir for receiving the dose of the non-steroidal anti-inflammatory drug, and an actuation member for making available the dose of the non-steroidal anti-inflammatory drug for inhalation by the patient through the mouthpiece.

The thromboembolic event may be a myocardial infarction, deep venous thrombosis, pulmonary embolism, or thrombotic stroke. The dose of the NSAID drug can be administered as a preliminary treatment in response to a symptom of a thromboembolic event. The NSAID may be acetylsalicylic acid and may be administered in a single dose or in multiple doses, e.g., 2, 3, 4, 5, 6, 7, 8, 9 or 10 or greater doses.

2. Definitions

The present dry particles or dry powders are suitable for delivery to the respiratory tract (e.g., pulmonary delivery) in a subject by inhalation. The dry particles may have a mass median aerodynamic diameter (MMAD) of less than about 20 μm, less than about 15 μm, less than about 10 μm, less than about 5 μm, from about 1 μm to about 10 μm, from about 1 μm to about 5 μm, from about 1 μm to about 3 μm, from about 1.7 μm to about 2.7 μm, or less.

The term "dispersible" describes the characteristic of a dry powder or dry particles to be dispelled into a respirable aerosol. Dispersibility of a dry powder or dry particles is expressed herein as the quotient of the volume median geometric diameter (VMGD) measured at a dispersion (i.e., regulator) pressure of 1 bar divided by the VMGD measured at a dispersion (i.e., regulator) pressure of 4 bar, or VMGD at 0.5 bar divided by the VMGD at 4 bar as measured by HELOS/RODOS. These quotients are referred to herein as "1/4 bar," and "0.5/4 bar," respectively, and dispersibility correlates with a low quotient. For example, 1/4 bar refers to the VMGD of respirable dry particles or powders emitted from the orifice of a RODOS dry powder disperser (or equivalent technique) at about 1 bar, as measured by a HELOS or other laser diffraction system, divided the VMGD of the same respirable dry particles or powders measured at 4 bar by HELOS/RODOS. Thus, a highly dispersible dry powder or dry particles will have a 1/4 bar or 0.5/4 bar ratio that is close to 1.0. Highly dispersible powders have a low tendency to agglomerate, aggregate or clump together and/or, if agglomerated, aggregated or clumped together, are easily dispersed or de-agglomerated as they emit from an inhaler and are breathed in by the subject. Dispersibility can also be assessed by measuring the size emitted from an inhaler as a function of flow rate.

The term "emitted dose" or "ED" refers to an indication of the delivery of a drug formulation from a suitable inhaler device after a firing or dispersion event. More specifically, for dry powder formulations, the ED is a measure of the percentage of powder that is drawn out of a unit dose package and that exits the mouthpiece of an inhaler device. The ED is defined as the ratio of the dose delivered by an inhaler device to the nominal dose (i.e., the mass of powder per unit dose placed into a suitable inhaler device prior to firing). The ED is an experimentally-measured parameter, and can be determined using the method of USP Section 601 Aerosols, Metered-Dose Inhalers and Dry Powder Inhalers, Delivered-Dose Uniformity, Sampling the Delivered Dose from Dry Powder Inhalers, United States Pharmacopeia Convention, Rockville, MD, 13th Revision, 222-225, 2007. This method utilizes an in vitro device set-up to mimic patient dosing.

The terms "FPF (<5.6)," "FPF (<5.6 μm)," and "fine particle fraction of less than 5.6 μm" refer to the fraction of a sample of dry particles that have an aerodynamic diameter of less than a certain size, e.g., 5.6 μm. For example, FPF (<5.6) can be determined by dividing the mass of respirable dry particles deposited on the stage one and on the collection filter of a two-stage collapsed Andersen Cascade Impactor (ACI) by the mass of respirable dry particles weighed into a capsule for delivery to the instrument. This parameter may also be identified as "FPF_TD (<5.6)," where TD means total dose. A similar measurement can be conducted using an eight-stage ACI. The eight-stage ACI cutoffs are different at the standard 60 l/min flow rate, but the FPF_TD (<5.6) can be extrapolated from the eight-stage complete data set. The eight-stage ACI result can also be calculated by the USP method of using the dose collected in the ACI instead of what was in the capsule to determine FPF.

The terms "FPF (<3.4)," "FPF (<3.4 μm)," and "fine particle fraction of less than 3.4 μm" refers to the fraction of a mass of respirable dry particles that have an aerodynamic diameter of less than a certain size, e.g., 3.4 μm. For example, FPF (<3.4) can be determined by dividing the mass of respirable dry particles deposited on the collection filter of a two-stage collapsed ACI by the total mass of respirable dry particles weighed into a capsule for delivery to the instrument. This parameter may also be identified as "FPF_TD (<3.4)," where TD means total dose. A similar measurement can be conducted using an eight-stage ACL. The eight-stage ACI result can also be calculated by the USP method of using the dose collected in the ACI instead of what was in the capsule to determine FPF.

The terms "FPF (<5.0)," "FPF (<5.0 μm)," and "fine particle fraction of less than 5.0 μm" as used herein, refer to the fraction of a mass of respirable dry particles that have an aerodynamic diameter of less than a certain size, e.g., 5.0 μm. For example, FPF (<5.0) can be determined by using an eight-stage ACI at the standard 60 L/min flow rate by extrapolating from the eight-stage complete data set. This parameter may also be identified as "FPF_TD (<5.0)," where TD means total dose.

The portion of the drug formulation falling within a size range is typically referred to as the fine particle fraction (FPF). In some cases, the FPF in the present invention can range from about 20% to about 90%, from about 20% to about 80%, from about 20% to about 70%, from about 20% to about 60%, from about 20% to about 50%, from about 20% to about 40%, from about 20% to about 30%, from about 30% to about 50%, or from about 30% to about 60%.

3. Non-Steroidal Anti-Inflammatory Drugs (NSAIDS)

NSAIDs, such as acetylsalicylic acid, can provide various beneficial effects and contribute to reducing the risk of a cardiovascular disease (such as thrombosis). However, the use of NSAIDs, such as acetylsalicylic acid, in a clinical setting has traditionally been limited to oral administration. Oral administration of acetylsalicylic acid, for example, can result in the loss or inactivation of approximately ⅔ of the oral dosage due to the first pass effect in the gut and liver. While one third of the dosage reaches the systemic blood stream and provides the desired effect, the negative side effects created by the fill dosage often deter patients from using acetylsalicylic acid on a regular or daily basis.

The methods and systems of the present invention allow for the beneficial effects of NSAIDs, such as acetylsalicylic acid, to be achieved on a regular basis and in emergency situations, while minimizing previous drawbacks associated with the use of NSAIDs.

Various studies have determined that acetylsalicylic acid has a significant effect on reducing the risk of myocardial infarction. These studies have used acetylsalicylic acid dosages of 325 mg. However, these studies have based their findings on oral administration of acetylsalicylic acid and have not suggested DPI or MDI administration.

Although inhaled dry powder formulations of acetylsalicylic acid have been developed, reports have stated that the formulation was not clinically feasible because it is difficult to meet the high dosage requirements of acetylsalicylic acid (~80 mg/day for low-dose prevention of coronary events and stroke, and at least 300 mg/day for pain or fever relief) via pulmonary delivery of dry powders.

In addition, these reports recognize that adverse effects of dry powder on the lungs, such as coughing, cannot be avoided unless the doses are less than a few tenths of a milligram in a single breath. Thus, prior teachings suggest that higher dosage requirements of acetylsalicylic acid would be impossible or difficult to meet using DPI (or MDI). Finally, there may be a higher incidence of acetylsalicylic acid intolerance in asthmatic patients when acetylsalicylic acid is delivered by inhalation than orally.

The methods and systems of the present invention provide for treating (including prophylactic treatment or reducing the risk of) a disease, for example, treating a cardiovascular disease (such as thrombosis) by administration of a low amount of a NSAID, such as a low dose of acetylsalicylic acid, by DPI. The dose can be much less than that of a baby acetylsalicylic acid (e.g., less than 81 mg). The administered dosage can be less than about 40 mg of acetylsalicylic acid. The administered dosage can be less than 25 mg of acetylsalicylic acid. Further, the administered dosage can be less than 20 mg of acetylsalicylic acid. The administered dosage can be less than 15 mg of acetylsalicylic acid. The administered dosage can also be less than 12 mg of acetylsalicylic acid. The administered dosage can be less than 10 mg of acetylsalicylic acid. Furthermore, the administered dosage can be less than 8 mg of acetylsalicylic acid. The administered dosage can be less than 5 mg of acetylsalicylic acid. In some embodiments, the administered dosage can be less than 2 mg of acetylsalicylic acid.

For example, the dosage can be from about 1 mg to about 40 mg. In various embodiments, the dosage can be from about 4 mg to about 25 mg of acetylsalicylic acid, about 6 mg to about 20 mg of acetylsalicylic acid, about 8 mg to about 15 mg of acetylsalicylic acid, about 10 mg to about 13 ng of acetylsalicylic acid or about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, or about 20 mg of acetylsalicylic acid. Alternatively, the dose of acetylsalicylic acid can be less than about 80 mg, about 1 mg to about 75 mg, about 2 mg to about 60 mg, about 5 mg to about 40 mg, about 10 mg to about 30 mg, about 12 mg to about 25 mg, about 15 mg to about 20 mg, about 60 mg to about 95 mg, about 50 mg to about 100 mg, about 50 mg to about 80 mg, about 40 mg to about 80 mg, about 20 mg to about 30 mg, about 30 mg to about 40 mg, about 40 mg to about 50 mg, about 50 mg to about 60 mg, about 60 mg to about 70 mg, about 70 mg to about 80 mg, about 80 mg to about 90 mg, or about 90 mg to about 100 mg.

In certain embodiments, NSAIDs can be used in various methods and systems. In some embodiments, NSAIDs can include salicylates, i.e., the salts and esters of salicylic acid, which have anti-platelet action. Further, NSAIDs can also include one or more of the following compounds listed in Table 1.

TABLE 1

| Examples of NSAIDs |
|---|
| Aspirin or acetylsalicylic acid |
| Celecoxib (Celebrex) |
| Dexdetoprofen (Keral) |
| Diclofenac (Voltaren, Cataflam, Voltaren-XR) |
| Diflunisal (Dolobid) |
| Etodolac (Lodine, Lodine XL) |
| Etoricoxib (Algix) |
| Fenoprofen (Fenopron, Nalfron) |
| Firocoxib (Equioxx, Previcox) |
| Flurbiprofen (Urbifen, Ausaid, Flurwood, Proben) |
| Ibuprofen (Advil, Brufen, Motrin, Nurofen, Medipren, Nuprin) |
| Indomethacin (Indocin, Indocin SR, Indocin IV) |
| Ketoprofen (Actron, Orudis, Oruvail, Ketoflam) |

TABLE 1-continued

| Examples of NSAIDs |
|---|
| Ketorolac (Toradol, Sprix, Toradol IV/IM, Toradol IM) |
| Licofelone (under development) |
| Lomoxicam (Xefo) |
| Loxoprofen (Loxonin, Loxomac, Oxeno) |
| Lumiracoxib (Prexige) |
| Meclofenamic acid (Meclomen) |
| Mefenamic acid (Ponstel) |
| Meloxicam (Movalis, Mel ox, Recoxa, Mobic) |
| Nabumetone (Relafen) |
| Naproxen (Aleve, Anaprox, Midol Extended Relief, Naprosyn, Naprelan) |
| Nimesulide (Sulide, Nimalox, Mesulid) |
| Oxaporozin (Daypro, Dayrun, Duraprox) |
| Parecoxib (Dynastat) |
| Piroxicam (Feldene) |
| Rofecoxib (Vioxx, Ceoxx, Ceeoxx) |
| Salsalate (Mono-Gesic, Salflex, Disalcid, Salsitab) |
| Sulindac (Clinoril) |
| Tenoxicam (Mobi flex) |
| Tolfenamic acid (Clotam Rapid, Tufnil) |
| Valdecoxib (Bextra) |

Other alternatives can also be used instead of a NSAID. Such alternatives include Plavix (clopidogrel), COX-2 inhibitors, other remedies such as Nattokinase (an enzyme (EC 3.4.21.62, extracted and purified from a Japanese food called nattō). Further, other drugs that provide different beneficial effects, such as being effective to reduce a risk of a cardiovascular disease (such as thrombosis) in a patient, can also be used in some embodiments. Thus, the discussion of methods and systems shall apply generally to these various alternatives, although for discussion purposes, the present disclosure often refers to acetylsalicylic acid. It is contemplated that the methods, effects, pharmacokinetic data, and other considerations relating to acetylsalicylic acid can be equally applied to other NSAIDs.

4. Dry Powders and Dry Particles

The dry particles of the subject technology may be dispersible. The size of the dry particles can be expressed in a variety of ways that are conventional in the art, such as, fine particle fraction (FPF), volumetric median geometric diameter (VMGD), or mass median aerodynamic diameter (MMAD).

The dry particles of the subject technology may have a VMGD as measured by HELOS/RODOS at 1.0 bar of about 10 μm or less (e.g., about 0.1 μm to about 10 μm). Preferably, the dry particles of the subject technology have a VMGD of about 9 μm or less (e.g., about 0.1 μn to about 9 μm), about 8 μm or less (e.g., about 0.1 μm to about 8 μm), about 7 μm or less (e.g., about 0.1 μm to about 7 μm), about 6 μm or less (e.g., about 0.1 μm to about 6 μm), about 5 μm or less (e.g., less than 5 μm, about 0.1 μm to about 5 μm), about 4 μm or less (e.g., 0.1 μm to about 4 μm), about 3 μm or less (e.g., 0.1 μm to about 3 μm), about 2 μm or less (e.g., 0.1 μm to about 2 μm), about 1 μm or less (e.g., 0.1 μm to about 1 μm), about 0.5 μm to about 6 μm, about 0.5 μm to about 5 μm, about 0.5 μm to about 4 μm, about 0.5 μm to about 3 μm, or about 0.5 μm to about 2 μm as measured by HELOS/RODOS at 1.0 bar. In an exemplary embodiment, the dry particles of the subject technology have a VMGD as measured by HELOS/RODOS at 1.0 bar of about 1.3 to about 1.7 μm. In another exemplary embodiment, the dry particles of the subject technology have a VMGD as measured by HELOS/RODOS at 1.0 bar of about 0.5 μm to about 2 μm.

Alternatively, the dry particles may have a VMGD as measured by HELOS/RODOS at 1.0 bar of about 30 µm or less (e.g., about 5 µm to about 30 µm). Preferably, the dry particles of the subject technology have a VMGD of about 25 µm or less (e.g., about 5 µm to about 25 µm), about 20 µm or less (e.g., about 5 µm to about 20 µm), about 15 µm or less (e.g., about 5 µm to about 15 µm), about 12 µm or less (e.g., about 5 µm to about 12 µm), about 10 µm or less (e.g., about 5 µm to about 10 µm), or about 8 µm or less (e.g., 6 µm to about 8 µm) as measured by HELOS/RODOS at 1.0 bar. The dry powders can comprise a mixture of particles having different sizes.

The respirable dry particles can have an MMAD of about 10 µm or less, such as an MMAD of about 0.5 µm to about 10 µm, about 1 µm to about 10 µm, about 0.5 µm to about 5 µm, or about 1 µm to about 5 µm. Preferably, the dry particles of the subject technology have an MMAD of about 5 µm or less (e.g. about 0.5 µm to about 5 µm, preferably about 1 µm to about 5 µm), about 4 µm or less (e.g., about 1 µm to about 4 µm), about 3.8 µm or less (e.g. about 1 µm to about 3.8 µm), about 3.5 μm or less (e.g. about 1 μm to about 3.5 μm), about 3.2 μm or less (e.g. about 1 μm to about 3.2 μm), about 3 μm or less (e.g. about 1 μm to about 3.0 μm), about 2.8 μm or less (e.g. about 1 μm to about 2.8 μm), about 2.2 μm or less (e.g. about 1 μm to about 2.2 μm), about 2.0 μm or less (e.g. about 1 μm to about 2.0 μm) or about 1.8 μm or less (e.g. about 1 micron to about 1.8 μm).

Alternatively, the dry powders and dry particles of the subject technology have a FPF of less than 5.0 μm (FPF_TD<5.0 μm) of at least about 20%, at least about 30% r, at least about 45%, at least about 40%, at least about 45%, at least about 50%, at least about 60%, at least about 65% or at least about 70%. Alternatively or in addition, the dry powders and dry particles of the subject technology have a FPF of less than 5.0 μm of the emitted dose (FPF_ED<5.0 μm) of at least about 45%, at least about 50%, at least about 60%, at least about 65%, at least about 70%, at least about 75%, at least about 80%, or at least about 85%.

In another embodiment, the dry powders and dry particles of the invention can have an FPF of less than about 5.6 μm (FPF<5.6 μm) of at least about 20%, at least about 30%, at least about 40%, preferably at least about 45%, at least about 50%, at least about 55%, at least about 60%, at least about 65%, or at least about 70%.

In a third embodiment, embodiment, the dry powders and dry particles of the invention can have an FPF of less than about 3.4 μm (FPF<3.4 μm) of at least about 20%, preferably at least about 25%, at least about 30%, at least about 35%, at least about 40%, at least about 45%, at least about 50%, or at least about 55%.

The dry powders and dry particles may have a tap density of about 0.1 g/cm$^3$ to about 1.0 g/cm$^3$. For example, the small and dispersible dry particles have a tap density of about 0.1 g/cm$^3$ to about 0.9 g/cm$^3$, about 0.2 g/cm$^3$ to about 0.9 g/cm$^3$, about 0.2 g/cm$^3$ to about 0.9 g/cm$^3$, about 0.3 g/cm$^3$ to about 0.9 g/cm$^3$, about 0.4 g/cm$^3$ to about 0.9 g/cm, about 0.5 g/cm$^3$ to about 0.9 g/cm$^3$, or about 0.5 g/cm$^3$ to about 0.8 g/cm$^3$, greater than about 0.4 g/cc, greater than about 0.5 g/cc, greater than about 0.6 g/cc, greater than about 0.7 g/cc, about 0.1 g/cm$^3$ to about 0.8 g/cm$^3$, about 0.1 g/cm$^3$ to about 0.7 g/cm$^3$, about 0.1 g/cm$^3$ to about 0.6 g/cm$^3$, about 0.1 g/cm$^3$ to about 0.5 g/cm$^3$, about 0.1 g/cm$^3$ to about 0.4 g/cm$^3$, about 0.1 g/cm$^3$ to about 0.3 g/cm$^3$, less than 0.3 g/cm$^3$. In a preferred embodiment, tap density is greater than about 0.4 g/cm$^3$; in another preferred embodiment, tap density is greater than about 0.5 g/cm$^3$. Alternatively, tap density may be less than about 0.4 g/cm$^3$.

The dry powders and dry particles can have a water or solvent content of less than about 15% by weight of the dry particle. For example, the dry particles can have a water or solvent content of less than about 15% by weight, less than about 13% by weight, less than about 11.5% by weight, less than about 10% by weight, less than about 9% by weight, less than about 8% by weight, less than about 7% by weight, less than about 6% by weight, less than about 5% by weight, less than about 4% by weight, less than about 3% by weight, less than about 2% by weight, less than about 1% by weight or be anhydrous. In another embodiment, the dry particles of the subject technology can have a water or solvent content of less than about 6% and greater than about 1%, less than about 5.5% and greater than about 1.5%, less than about 5% and greater than about 2%, about 2%, about 2.5%, about 3%, about 3.5%, about 4%, about 4.5% about 5%.

Depending on the specific applications, the present composition (e.g., the present dry powders or dry particles) may contain a low or high percentage of active ingredient in the composition. For example, the dry particles may contain 3% or more, 5% or more, 10% or more, 15% or more, 20% or more, 25% or more, 30% or more, 35% or more, 40% or more, 50% or more, 60% or more, 70% or more, 75% or more, 80% or more, 85% or more, 90%, or more, 95% or more, about 30% to about 99%, about 40% to about 99%, about 50% to about 99%, about 60% to about 99%, about 70% to about 99%, about 80% to about 99%, about 40% to about 95%, or about 50% to about 95% (weight percentage, w/w) of the active ingredient (e.g., acetylsalicylic acid).

5. Delivery of Dry Powders

In a dry powder inhalation technique, a patient can use a dry powder inhaler to inhale a powder formulation of a drug, such as a NSAID. The dose is effective to reduce a risk of a thromboembolic event in the patient.

Various types of inhalers can be used to provide the drug using a DPI or MDI delivery system. The dose administered can be effective to reduce a risk of a thromboembolic event in a patient.

For example, the dry powder inhaler 10 can comprise a mouthpiece, a reservoir for receiving the NSAID, and an actuation member for making available the NSAID for inhalation by a patient through the mouthpiece.

The methods and systems of the present invention may be adapted for use with any DPI or MDI device, including, but not limited to Aerolizer®, Diskus®, Ellipta®, Flexhaler®, Handihaler®, Neobaler®, Pressair®, Rotahaler®, Turbuhaler® or Twisthaler® Plastiape, CDMHaler (see, http://www.nationaljewish.org/healthinfo/medications/devices/dry-powder).

The methods and systems of the invention provide an apparatus and method for providing a therapeutically effective dose of an NSAID in order to reduce the risk of a thromboembolic event. As discussed above, the general approach is to deliver an NSAID in a pharmaceutically acceptable powdered form (e.g., Acetylsalicylic acid, and/or derivatives thereof) by means of an inhaler.

With respect to the particle size distribution (PSD), the present composition may contain particles having same (or similar) size distribution, or particles having different size distributions. The particle sizes of the present composition may have a mono-modal, bimodal or multimodal distribution. As a result, the present composition may produce mono-modal, bimodal or multimodal absorption. In other words, administration of the present composition may result in a mono-modal, bimodal or multimodal concentration-time profile.

For example, the present composition may contain one, two or three groups of the following: particles with a median aerodynamic diameter in a range from about 1 µm to about 5 µm, particles with a median aerodynamic diameter in a range from about 5 µm to about 15 µm, and particles with a median aerodynamic diameter greater than about 15 µm, Mixing particles of the same active ingredient (e.g., acetylsalicylic acid), using batches of particles having different size distributions, may reduce bridging. For example, while a composition having a relatively uniform particle size will aggregate, providing a blended composition having some particles with a median aerodynamic diameter in a range from about 1 µm to about 5 µm, other particles with a median aerodynamic diameter in a range from about 5 µm to about 15 µm, and still other particles with a median aerodynamic diameter greater than about 15 µm, may inhibit aggregation and maintain the deposition characteristics of the preparation. In effect, the pharmaceutically active compound is used to replace the function of an excipient (such as lactose) with respect to preventing aggregation during storage of the medicament.

In addition, by selecting the proportions of the various particle sizes, one can provide formulations that are faster or slower acting, based on the location of where the drug is ultimately deposited. For example, some embodiments provide a preparation that comprises 80% acetylsalicylic acid particles with a median aerodynamic diameter of about 1 µm to about 5 µm, and about 20% of particles with a median aerodynamic diameter of at least 15 µm. Other combinations are possible as well, and those of skill in the art will readily appreciate that faster acting preparations will comprise proportionately more smaller particles, while slower acting preparations will comprise proportionately more large particles. Thus, using the apparatus and methods described herein it is therefore possible to provide a therapeutically effective dose of an NSAID such as acetylsalicylic acid via the respiratory tract, at least as rapidly as can be achieved by oral dosing.

Where a slower acting dosage form is desired, the formulation may include increasing fractions of particles with a median aerodynamic diameter in the range from about 5 µm to about 10 µm, or 15 µm or greater. These preparations would result in deposition in either the airways or oral cavity and pharynx and thus provide a more gradual increase in circulating levels of acetylsalicylic acid and its metabolic derivatives.

Accordingly, one aspect of the subject technology provides a dry powder that comprises a mixture of particles of various sizes.

For example, the dry powder can comprise particles of large sizes, as measured by VMGD (e.g., VMGD≥15 µm, such as ≥20 µm or 20-30 µm) and of small sizes, as measured by VMGD (e.g., VMGD≤5 µm, such as ≤1-3 µm) at a ratio (w:w) of: about 1:1, about 1:2, about 1:3, about 1:4, about 1:5, about 1:6, about 1:7, about 1:8, about 1:10, about 1:15, about 1:20, about 1:25, about 1:30, about 1:40, about 1:50, about 1:100, about 2:1, about 3:1, about 4:1, about 5:1, about 6:1, about 7:1, about 8:1, about 9:1, about 10:1, about 15:1, about 20:1, about 25:1, about 30:1, about 40:1, about 50:1, or about 100:1, etc.

Alternatively, the dry powder can comprise: about 1%, about 5%, about 10%, about 15%, about 20%, about 25%, about 30%, about 35%, about 40%, about 45%, about 50%, about 55%, about 50%, about 55%, about 60%, about 65%, about 70%, about 75%, about 80%, about 85%, about 90%, about 95%, or about 99% (weight percentage) of particles having VMGD of about 10 µm or less, preferably about 5 µm or less. Particles of 10 µm or less generally can reach lungs, and particles of 5 µm or less (e.g., 1-3 µm) generally can reach alveoli.

In another embodiment, the dry powder can comprise: about 1%, about 5%, about 10%, about 15%, about 20%, about 25%, about 30%, about 35%, about 40%, about 45%, about 50%, about 55%, about 50%, about 55%, about 60%, about 65%, about 70%, about 75%, about 80%, about 85%, about 90%, about 95%, or about 99% (weight percentage) of particles having VMGD of between about 5 µm to about 20 µm, preferably between about 5 µm to about 15 µm, or between about 5 µm to about 10 µm.

Alternatively, the dry powder can comprise: about 1%, about 5%, about 10%, about 15%, about 20%, about 25%, about 30%, about 35%, about 40%, about 45%, about 50%, about 55%, about 50%, about 55%, about 60%, about 65%, about 70%, about 75%, about 80%, about 85%, about 90%, about 95%, or about 99% (weight percentage) of particles having VMGD of about 15 µm, 20 µm or more.

The above features can be combined. For example, the dry power can comprise about 50% of particles of about 5 µm or less (VMGD), about 25% of particles of about 5 to about 15 µm (VMGD), and about 25% of particles of about 15 µm or more (VIGD).

The dry powder can also comprise a mixture of particles having various mass median aerodynamic diameters (MMAD). For example, the dry powder can comprise particles of large sizes (e.g., MMAD 2: 15 µm, such as 2:20 µm or 20-30 µm) and of small sizes (e.g., MMAD: 5 µm, such as 1-3 µm) at a ratio (w:w) of: about 1:1 about 1:2, about 1:3 about 1:4, about 1:5, about 1:6, about 1:7, about 1:8, about 1:10, about 1:15, about 1:20, about 1:25, about 1:30, about 1:40, about 1:50, about 1:100, about 2:1, about 3:1, about 4:1, about 5:1, about 6:1, about 7:1, about 8:1, about 9:1, about 10:1, about 15:1 about 20:1, about 25:1, about 30:1, about 40:1, about 50:1, or about 100:1, etc Alternatively the dry powder can comprise: about 1%, about 5%, about 10%, about 15%, about 20%, about 25%, about 30%, about 35%, about 40%, about 45%, about 50%, about 55%, about 50%, about 55%, about 60%, about 65%, about 70%, about 75%, about 80%, about 85%, about 90%, about 95%, or about 99% (weight percentage) of particles having MMAD of about 10 µm or less, preferably about 5 µm or less. Particles of 10 µm or less generally can reach lungs, and particles of 5 µm or less (e.g., 1-3 µm) generally can reach alveoli.

In another embodiment, the dry powder can comprise: about 1%, about 5%, about 10%, about 15%, about 20%, about 25%, about 30%, about 35%, about 40%, about 45%, about 50%, about 55%, about 50%, about 55%, about 60%, about 65%, about 70%, about 75%, about 80%, about 85%, about 90%, about 95%, or about 99% (weight percentage) of particles having MMAD of between about 5 µm to about 20 µm, preferably between about 5 µm to about 15 µm or between about 5 µm to about 10 µm.

In another embodiment, the dry powder can comprise: about 1%, about 5%, about 10%, about 15%, about 20%, about 25%, about 30%, about 35%, about 40%, about 45%, about 50%, about 55%, about 50%, about 55%, about 60%, about 65%, about 70%, about 75%, about 80%, about 85%, about 90%, about 95%, or about 99% (weight percentage) of particles having MMAD of about 15 µm or more, preferably 20 µm or more.

The above features can be combined. For example, the dry power can comprise about 50% of particles of about 5 µm or less (MMAD), about 25% of particles of about 5 to about 15 µm (MMAD), and about 25% of particles of about 15 µm or more (MMAD).

In certain embodiments, the dry powder may not have an excipient, which may be an anti-aggregation (or anti-bridging) excipient.

The dry powder can comprise a mixture of particles of various sizes, and is effective to substantially prevent or reduce particle bridging. In certain embodiments, at least about 40%, at least about 45%, at least about 50%, at least about 55%, at least about 60%, at least about 65%, at least about 70%, at least about 75%, at least 80%, at least about 85%, or at least about 90% of the NSAID (such as acetylsalicylic acid) in the dry powder is delivered to the alveolar spaces of a lung.

6. Methods for Preparing Dry Powders and Dry Particles

The dry particles and dry powders can be prepared using any suitable method. Many suitable methods for preparing dry powders and particles are conventional in the art, and include single and double emulsion solvent evaporation, spray drying, milling (e.g., jet milling), blending, solvent extraction, solvent evaporation, phase separation, simple and complex coacervation, interfacial polymerization, suitable methods that involve the use of supercritical carbon dioxide ($CO_2$), and other suitable methods. Dry particles can be made using methods for making microspheres or microcapsules known in the art. These methods can be employed under conditions that result in the formation of dry particles having the desired aerodynamic properties (e.g., aerodynamic diameter and geometric diameter). If desired, dry particles with desired properties, such as size and density, can be selected using suitable methods, such as sieving.

Spray Drying

Dry particles can be produced by spray drying. Suitable spray drying techniques are described, for example, by K. Masters in "*Spray Drying Handbook*", John Wiley & Sons, New York (1984); and spray drying techniques developed by BUCHI Laboratory Equipment or GEA Niro drying technology. Generally, during spray drying, heat from a hot gas such as heated air or nitrogen is used to evaporate a solvent from droplets formed by atomizing a continuous liquid feed. If desired, the spray drying or other instruments, e.g., jet milling instrument, used to prepare the dry particles can include an inline geometric particle sizer that determines a geometric diameter of the respirable dry particles as they are being produced, and/or an inline aerodynamic particle sizer that determines the aerodynamic diameter of the respirable dry particles as they are being produced.

For spray drying, solutions, emulsions or suspensions that contain the components of the dry particles to be produced in a suitable solvent (e.g., aqueous solvent, organic solvent, aqueous-organic mixture or emulsion) are distributed to a drying vessel via an atomization device. For example, a nozzle or a rotary atomizer may be used to distribute the solution or suspension to the drying vessel. For example, a rotary atomizer having a 4- or 24-vaned wheel may be used. Examples of suitable spray dryers that can be outfitted with either a rotary atomizer or a nozzle, include, Mobile Minor Spray Dryer or the Model PSD-1, both manufactured by Niro, Inc. (Denmark). Actual spray drying conditions will vary depending, in part on the composition of the spray drying solution or suspension and material flow rates. The person of ordinary skill will be able to determine appropriate conditions based on the compositions of the solution, emulsion or suspension to be spray dried, the desired particle properties and other factors. In general, the inlet temperature to the spray dryer is about 100° C. to about 300° C., and preferably is about 220° C. to about 285° C. The spray dryer outlet temperature will vary depending upon such factors as the feed temperature and the properties of the materials being dried. Generally, the outlet temperature is about 50° C. to about 150° C., preferably about 90° C. to about 120° C., or about 98° C. to about 108° C. If desired, the respirable dry particles that are produced can be fractionated by volumetric size, for example, using a sieve, or fractioned by aerodynamic size, for example, using a cyclone, and/or further separated according to density using techniques known to those of skill in the art.

To prepare the dry particles of the subject technology, generally, a solution, emulsion or suspension that contains the desired components of the dry powder (i.e., a feed stock) is prepared and spray dried under suitable conditions. Preferably, the dissolved or suspended solids concentration in the feed stock is at least about 1 g/L, at least about 2 g/L, at least about 5 g/L, at least about 10 g/L, at least about 15 g/L, at least about 20 g/L, at least about 30 g/L, at least about 40 g/L, at least about 50 g/L, at least about 60 g/L, at least about 70 g/L, at least about 80 g/L, at least about 90 g/L, or at least about 100 g/L. The feedstock can be provided by preparing a single solution or suspension by dissolving or suspending suitable components (e.g., salts, excipients, other active ingredients) in a suitable solvent. The solvent, emulsion or suspension can be prepared using any suitable methods, such as bulk mixing of dry and/or liquid components or static mixing of liquid components to form a combination. For example, a hydrophilic component (e.g., an aqueous solution) and a hydrophobic component (e.g., an organic solution) can be combined using a static mixer to form a combination. The combination can then be atomized to produce droplets, which are dried to form respirable dry particles. Preferably, the atomizing step is performed immediately after the components are combined in the static mixer.

In one example, dry particles that comprise acetylsalicylic acid can be prepared by spray drying. Spray drying is a commonly used method of drying a liquid feed through a hot gas. It is a method whereby solutions or slurries can be rapidly dried to particulate form by atomizing the liquid in a heated chamber. Typically, the hot gas can be air. When preparing chemically sensitive materials such as pharmaceuticals, or when solvents such as ethanol are used, oxygen-free atmosphere may be required, such as nitrogen. Spray drying is frequently used in the food preparation industry and has become an important method for the dehydration of fluid foods such as milk, coffee, and egg powder. The process is also adaptable to preparations of pharmaceutical and chemical formulations.

The liquid feed varies depending on the material being dried and is not limited to food or pharmaceutical products, and may be a solution, colloid or suspension. The process is a one-step rapid method that typically eliminates additional processing. By controlling process conditions particles of the desired size can be reproducibly formed.

The spray drying can be conducted in the presence or absence of one or more excipients. In some cases, excipients can be included with the active pharmaceutical ingredient such that a complex particle of active pharmaceutical ingredient (API) and excipient can be produced in a single step process. In other cases, an active pharmaceutical particulate preparation can be produced in a first spray-drying process, and that product then modified by the subsequent addition of one or more pharmaceutically acceptable excipients. In some cases, it is possible to add excipients by a subsequent spray-drying process.

In some spray-drying methods, the liquid feed is pumped through an atomizer nozzle, or array of nozzles, that produce fine droplets that are introduced into the main drying chamber. Atomizers can vary there being rotary, single fluid, two-fluid, and ultrasonic designs. These different designs provide a variety of advantages, applicability and disadvantages depending on the particular spray drying process required. The hot drying gas can be passed as a concurrent or counter-current flow to the atomizer direction. The concurrent flow enables the particles to have a lower residence time within the system and the particle separator thus operates more efficiently. In some systems the particle separator is a cyclone device. The counter-current flow method enables a greater residence time of the particles in the chamber. Therefore, in general a spray-drying method will consist of the steps of pre-concentration of liquid, atomization, drying in a hot gas atmosphere, separation of the dried powder from moist gas, cooling, and then packaging of the finished product.

In one embodiment, feed solutions with acetylsalicylic acid concentrations of either 2% w/w or 5% w/w, were prepared by adding acetylsalicylic acid to the appropriate solvent followed by stirring until a homogeneous solution was obtained. A BUCHI spray dryer model B-290 Advanced was used in all experiments. The unit was equipped with a two fluid nozzle where the nozzle and diameter were 1.4 mm and 0.7 mm, respectively. The high-performance cyclones were used to collect the dried product. The spray-drying unit was operated in open cycle, with the aspirator blowing nitrogen at 100% of capacity, corresponding to a flow rate of the dry nitrogen of approximately 40 kg per hour. The flow rate of atomization nitrogen was adjusted to 40 mm or 50 mm in the rotameter, depending on the particular trial. Before feeding the stock solution, the spray dryer was stabilized with the solvent. During the stabilization period, the solvent flow rate was adjusted in order to give the target outlet temperature. After stabilization of the outlet temperature, the feed of the spray dryer was commuted from the solvent to the product solution (inlet temperature was then readjusted to maintain the outlet temperature in the target value). At the end of the stock solution, the feed was once more commuted to solvent, in order to rinse the feed line and carry out a controlled shutdown.

The initial objective of these experiments was to isolate the amorphous form of acetylsalicylic acid, in order to fully characterize it. However, as was discovered from a review of the literature, acetylsalicylic acid presents a negative Tg (of −30° C.), and as such the option of producing a crystalline size reduced active pharmaceutical with this technique was attempted. For that purpose, for solutions of acetylsalicylic acid in ethanol (the most suited solvent to dissolve the acetylsalicylic acid, given its high solubility and its approval for inhalation use) were prepared and spray dried as follows. Inlet temperature ranged from about 80° C. to about 160° C. Outlet temperature was initially set to 65° C. In one experiment the outlet temperature was increased to 100° C. in an attempt to accelerate the amorphous-crystalline conversion, in the hopes that this would reduce losses that are typical of the transient glassy state of the material. However, increasing the outlet temperature did not produce any appreciable increase in overall yield of product. The rotameter was varied from about 40 mm to about 50 mm. Feed rate was typically about 5 mL per minute. Following spray drying, a number of analytical methods were used to evaluate the resulting product.

X-ray powder diffraction (XRPD) showed that in each of the four different batches prepared acetylsalicylic acid appeared to be crystalline in form, and the diffractogram was similar to that of the starting material. In addition, the spray dried products presented thermal grams that were identical to the input material. The overall yield ranged from about 55% to about 65%.

The melting temperature of the resulting spray dried product ranged from about 133° C. to about 137° C., comparing favorably with the published melting point for acetylsalicylic acid (136° C.). A measure of hygroscopic properties showed a weight change ranging from −0.4% to about 1.2% when the products were exposed to an atmosphere with 95% relative humidity. These results suggest no issues with hygroscopic behavior and that with respect to this property, spray dried acetylsalicylic acid behaves in a manner similar to that of unprocessed acetylsalicylic acid.

Particle size distribution analysis showed that $DV_{10}$ ranged from about 0.9 μm to about 1.2 μm, $DV_{50}$ ranged from about 3 sun to about 6 μm, and $DV_{90}$ ranged from about 8 μm to about 24 μm. It was discovered that by reducing feed concentration of acetylsalicylic acid to 2% w/w a smaller average particle size could be obtained, which was within typical inhalation range.

HPLC analysis showed acetylsalicylic acid purity to range from about 92% to about 98%, with the major "impurity" being salicylic acid, which ranged from about 0.3% to about 0.5%. Residual solvent ranged from about 90 ppm to about 150 ppm, well below the limits defined in the ICH Q3A guidelines.

The feedstock, or components of the feed-stock, can be prepared using any suitable solvent, such as an organic solvent, an aqueous solvent or mixtures thereof. Suitable organic solvents that can be employed include but are not limited to alcohols such as, for example, ethanol, methanol, propanol, isopropanol, butanols, and others. Other organic solvents include but are not limited to perfluorocarbons, dichloromethane, chloroform, ether, ethyl acetate, methyl tert-butyl ether and others. Co-solvents that can be employed include an aqueous solvent and an organic solvent, such as, but not limited to, the organic solvents as described above. Aqueous solvents include water and buffered solutions (such as phosphate buffer).

The feedstock or components of the feed stock can have any desired pH, viscosity or other properties. If desired, a pH buffer can be added to the solvent or co-solvent or to the formed mixture. Generally, the pH of the mixture ranges from about 3 to about 8.

Jet Milling

Respirable particles can also be produced by jet-milling. See, e.g., techniques developed by Apex Process Technology or Jetpharma SA. Jet milling is a process of using highly compressed air or other gasses, usually in a vortex motion, to impact fine particles against each other in a chamber. Jet mills are capable of reducing solids to particle sizes in the low-micron to submicron range. The grinding energy is created by gas streams from horizontal grinding air nozzles. Particles in the fluidized bed created by the gas streams are accelerated towards the center of the mill, colliding with slower moving particles. The gas streams and the particles carried in them create a violent turbulence and as the particles collide with one another they are pulverized.

In certain embodiments, jet-milling was able to produce acetylsalicylic acid particles with a FPF within the desired inhalable range for maximal deposition at the deepest levels of the lung. In some cases the $DV_{90}$ was less than about 9 µm, in some cases less than about 5 µm, and in some cases less than about 3 µm. Particles produced by jet milling can be efficiently and predictably delivered from a dry powder inhaler device, and at least 25% of the particles are of a size that would be expected to deposit within the alveolar spaces of the lungs. In some cases at least 50% of the particles are of a size that would be expected to deposit within the alveolar spaces of the lungs. In one embodiment, at least 75% of the particles are of a size that would be expected to deposit within the alveolar spaces of the lungs. In another embodiment, at least 90% of the particles are of a size that would be expected to deposit within the alveolar spaces of the lungs.

Wet Polishing

Wet polishing is a process that combines a technology to attain a small particle size (either a bottom up technique such as controlled crystallization or nanocrystallization or top down technique such as high shear mixing or high pressure homogenization) with a suitable isolation technology (for example spray drying or filtration with a drying process). See, e.g., techniques developed by Hovione. These combinations can be used to tune the particle size and morphology to meet specific drug delivery needs. The method allows control of particle size distribution with tight spans and in-process sampling, and maintains crystalline state (little or no amorphous content).

Wet polishing technique can be repeated multiple times to achieve a particular size of about 500 nanometers or less. Studies were undertaken to investigate whether wet polishing could provide an appropriate method for producing acetylsalicylic acid particles of an inhalable size and which were deliverable from a dry powder inhaler device. Initially, a literature review was conducted in order to determine the best candidate anti-solvent for use in reducing acetylsalicylic acid particle size by a wet-polishing method. Solvents were evaluated by their predicted ability with respect to minimal solubility of acetylsalicylic acid. From this review, the following candidate solvents were identified: water benzene, toluene, hexane n-heptane, dibutyl ether and di-isopropyl-ether.

After considering a number of factors in the end it was determined that only n-heptane and toluene fulfilled all the requirements, and therefore these were selected for further evaluation. Suspensions of acetylsalicylic acid at 5% w/w were prepared with the various anti-solvents, by charging the required amount of anti-solvent, charging the required amount of acetylsalicylic acid, and then stirring until a homogeneous suspension was obtained. The suspensions were qualitatively evaluated at room temperature and then filtered using a 0.45 μm membrane, which was then placed in an oven and dried at 60° C. until the solvent had completely evaporated. A quantitative analysis was performed on the residue that remained in the membrane by weighing the membrane before and after the test. From this analysis it was determined that acetylsalicylic acid was partially soluble in toluene, and displayed a phobic behavior towards n-heptane.

Suspensions were prepared using either toluene or n-heptane at an acetylsalicylic acid concentration of 5% w/w. Each individual suspension was then subjected to a milling operation using a Microfluidics Model M-110EH-30 apparatus. Milling was conducted at a pressure of 50 bar using a 200 μm chamber for between 20 and 70 cycles. Input temperatures ranged from about 80° C. to about 140° C.

Output temperatures ranged from about 65° C. to about 90° C. The process yield ranged from about 5% to about 25%.

Analysis of the resulting product revealed a $DV_{10}$ ranging from about 1.5 μm to about 3.3 μm, $DV_{50}$ ranging from about 3.3 μm to about 6.7 μm, and $DV_{90}$ ranging from about 6.3 μm to about 12.0 μm. HPLC assay of the final product revealed a composition of acetylsalicylic acid ranging from 90% to about 98%, with impurities ranging from about 1.4% to about 12%. The primary impurity was salicylic acid. It was also observed that all of the products obtained by wet polishing were more hygroscopic than the raw material, showing a water gain of about 5% when in the presence of 95% relative humidity.

In addition, when tested for aerodynamic performance, acetylsalicylic acid processed by wet polishing performed poorly in two different dry powder delivery devices. When examining devices loaded with either 15 mg or 40 mg, a significant amount of material (about 25 to 30%) was retained within the inhalation device itself. Overall, the results suggested that wet polishing alone impacts to a significant extent the physical and chemical properties of acetylsalicylic acid, and therefore were seen to be less desirable for producing a pharmaceutical product for inhalation. Wet polishing may nonetheless be a suitable method for micronization of acetylsalicylic acid for other purposes.

In some cases, it is possible to produce acetylsalicylic acid particles of a desired size using a process known as controlled crystallization. It is well known in the art that the crystalline state of most compounds is more thermodynamically stable that the amorphous state. As a result, producing acetylsalicylic acid in crystalline form is expected to improve stability of the active ingredient. In addition, production of acetylsalicylic acid in crystalline form also provides the potential to modify the active ingredient to optimize various biochemical properties, such as solubility, dissolution rate and pH solubility profile (among others) in order to improve pharmacokinetic performance. In some cases, sequential crystallization steps can be used to improve the purity of the active ingredient and selectively remove undesirable impurities.

Similarly, through the proper selection of various solvents and anti-solvents, it is possible to manipulate physical characteristics such as crystal shape. It is well known that certain crystal shapes are difficult to handle both at the product development and manufacturing stages. For example, needles and flakes are widely regards as less desirable particle shapes. It is possible however, to manipulate crystal formation in order to direct the final product to more suitable crystal shapes. In some cases, it is possible to grow crystals with high aspect ratios using non-polar hydrocarbon solvents such as hexane or heptane. In contrast, crystals having a low aspect ratio can be produced using polar solvents such as methanol or ethanol. The addition of surface active "impurities" can also be used to inhibit crystal growth in certain planar forms.

The solubility of acetylsalicylic acid in a number of solvents was first evaluated prior to initiating controlled crystallization by addition of a suitable anti-solvent. The results are shown in the following Table 2.

TABLE 2

Solubility of acetylsalicylic acid

| Solvent | T (° C.) | g/ml | T (° C.) | g/ml |
|---|---|---|---|---|
| EtOH | 23 | 0.125 | 3 | 0.063 |
| Acetone | 23 | 0.200 | 3 | 0.143 |

TABLE 2-continued Solubility of acetylsalicylic acid

| Solvent | T (° C.) | g/ml | T (° C.) | g/ml |
|---|---|---|---|---|
| MeOH | 23 | 0.167 | 3 | 0.133 |
| DMF | 23 | 0.500 | — | — |
| THF | 23 | 0.500 | 3 | 0.250 |
| PEG-200 | 23 | 0.077 | — | — |

Next, several small crystallization experiments were carried out to evaluate the behavior of the acetylsalicylic acid in different systems. Each experiment consisted of dissolving 2 μm of acetylsalicylic acid in a solvent (T=20-25° C.), and then adding this solution to the anti-solvent (100 vol. of anti-solvent at ~5° C.). The suspension obtained was stirred for 15 min and solid material collected by filtration and then dried. Table 3 summarizes the conditions of each experiment.

TABLE 3

Summary of the crystallization experiments

| Solvent | (v/w) | T (° C.) | Anti-Solvent | (v/w) | T (° C.) | Crystals | Yield |
|---|---|---|---|---|---|---|---|
| EtOH | 8 | 20-25 | H₂O | 100 | 4 | yes | 51.5 |
| EtOH | 8 | 20-25 | n-Hept | 100 | 4 | yes | 58.0 |
| EtOH | 8 | 20-25 | Toluene | 100 | 4 | no | — |
| EtOH | 8 | 20-25 | H₂O | 100 | 4 | yes | 53.0 |
| H2SO4 | 0.05 | | | | | | |
| THF | 2.5 | 20-25 | H₂O | 100 | 4 | yes | 53.5 |
| THF | 2.5 | 20-25 | Toluene | 100 | 4 | yes | 45.5 |
| THF | 2.5 | 20-25 | n-Hept | 100 | 4 | yes | 89.0 |
| MeOH | 6 | 20-25 | H₂O | 100 | 4 | yes | 64.5 |
| MeOH | 6 | 20-25 | n-Hept | 100 | 4 | yes | 17.0 |
| MeOH | 6 | 20-25 | Toluene | 100 | 4 | no | — |
| Acetone | 7 | 20-25 | H₂O | 100 | 3 | yes | 43.0 |
| Acetone | 7 | 20-25 | n-Hept | 100 | 4 | yes | 71.5 |
| Acetone | 7 | 20-25 | Toluene | 100 | 4 | yes | 34.5 |

Excipients

Particles described herein can be encapsulated, e.g., by a pharmaceutical excipient such as lactose, sugar, or a polymer.

In addition, particles described herein can be mixed and/or coated with various pharmaceutically acceptable excipients. Excipients can be included in order to improve aerodynamic performance of the active drug, to improve bioavailability, increase stability, to modulate pH, to provide sustained release properties, to provide taste-masking of an irritating drug and/or to improve pharmacokinetic performance.

With dry powder formulations, excipients can also provide a carrier function to reduce clumping of the active pharmaceutical ingredient and to improve suspension of the formulation in the airflow as the pharmaceutical preparation is being inhaled. Such carriers can include substances such as, but not limited to, sugars/sugar alcohols such as glucose, saccharose, lactose and fructose, starches or starch derivatives, oligosaccharides such as dextrins, cyclodextrins and their derivatives, polyvinylpyrrolidine, alginic acid, tylose, silicic acid, cellulose, cellulose derivatives, sugar alcohols such as mannitol or sorbitol, calcium carbonate, calcium phosphate, lactose, lactitol, dextrates, dextrose, maltodextrin, saccharides including monosaccharides, disaccharides, polysaccharides; sugar alcohols such as arabinose, ribose, mannose, sucrose, trehelose, maltose and dextran.

In some cases, an excipient can be provided in order to coat the active pharmaceutical ingredient, thus "masking" it. Masking is especially useful when the unmodified active pharmaceutical is imitating or otherwise unpleasant to the recipient. For example, in some cases it has been shown that coating a bitter molecule with a hydrogenated oil and surfactant combination is effective to cover the otherwise unpleasant taste of the active ingredient.

Non-limiting examples of pharmaceutically acceptable excipients include phospholipids. The phospholipids may or may not have surfactant properties. Examples of suitable phospholipid excipients include, without limitation, phosphatidylcholines, phosphatidylethanolamines, phosphatidylinositol, phosphatidylserines, sphingomyelin or other ceramides, as well as phospholipid containing oils such as lecithin oils. Combinations of phospholipids, or mixtures of a phospholipid(s) and other substance(s), may be used. In one embodiment, the phospholipids used as excipients are soy lecithin. In another embodiment, the phospholipid is endogenous to the lung.

Non-limiting examples of the phospholipids that may be used in the present composition include, soy lecithin, dipalmitoylphosphatidylcholine (DPPC), distearoylphosphatidylcholine (DSPC), dilaurylolyphosphatidylcholine (DLPC), dimyristoylphosphatidylcholine (DMPC), dioleoylphosphatidylcholine (DOPC), dilaurylolylphosphatidylglycerol (DLPG), dimyristoylphosphatidylglycerol (DMPG), dipahnitoylphosphatidylglycerol (DPPG), distearoylphosphatidylglycerol (DSPG), dioleoylphosphatidylglycerol (DOPG), dimyristoyl phosphatidic acid (DMPA), dimyristoyl phosphatidic acid (DMPA), dipahnitoyl phosphatidic acid (DPPA), dipalmitoyl phosphatidic acid (DPPA), dimyristoyl phosphatidylethanolamine (DMPE), dipalmitoyl phosphatidylethanolamine (DPPE), dimyristoyl phosphatidylserine (DMPS), dipalmitoyl phosphatidylserine (DPPS), dipahnitoyl sphingomyelin (DPSP), and distearoyl sphingomyelin (DSSP).

In one embodiment, soy lecithin, dipalmitoyl phosphatidylcholine (DPPC), distearoyl phosphatidylcholine (DSPC) or a mixture thereof are used as an excipient.

An excipient may be used to in the present composition. The excipient(s) may be present at levels ranging from about 0% to about 99% (w/w), from about 0.01% to about 80% (w/w), from about 0.05% to about 70% (w/w), from about 0.1% to about 60% (w/w), from about 0.1% to about 50% (w/w), from about 0.1% to about 40% (w/w), from about 0.1% to about 30% (w/w), from about 0.1% to about 20% (w/w), from about 0.1% to about 10% (w/w), from about 0.05% to about 8% (w/w), from about 0.1% to about 6% (w/w), from about 5% to about 10% (w/w), from about 3% to about 8% (w/w), from about 2% to about 6% (w/w), from about 0.1% to about 5% (w/w), from about 0.1% to about 4% (w/w), from about 0.1% to about 3% (w/w), from about 0.1% to about 2% (w/w), from about 0.1% to about 1% (w/w), from about 1% to about 6% (w/w), from about 1% to about 5% (w/w), from about 1% to about 4% (w/w), or from about 1% to about 3% (w/w) of the particles. In certain embodiments, one or more excipients (e.g., one or more phospholipids) are present at levels in a range from about 0.1% to about 10% (w/w), from about 1% to about 5% (w/w), about 0.1%, about 5% (w/w), about 3%, or about 10% (w/w) of the particles.

In addition, in some embodiments, the surfactant can be provided in combination with one or more additional excipients including absorbents, acidifiers, alkalizers, buffers, antimicrobial agents, antioxidants, binders, solubilizing agents, solvents, viscosity modifiers, humectants and combinations thereof. In some embodiments the formulation includes salts in amounts effective to render the dissolved formulation isosmotic with the lung.

Respirable dry particles and dry powders can be fabricated and then separated, for example, by filtration or centrifugation by means of a cyclone, to provide a particle sample with a preselected size distribution. For example, greater than about 30%, greater than about 40%, greater than about 50%, greater than about 60%, greater than about 70%, greater than about 80%, or greater than about 90% of the respirable dry particles in a sample can have a diameter within a selected range. The selected range within which a certain percentage of the respirable dry particles fall can be, for example, any of the size ranges described herein, such as between about 0.1 to about 3 μm VMGD.

The diameter of the respirable dry particles, for example, their VMGD, can be measured using an electrical zone sensing instrument such as a Multisizer lie, (Coulter Electronic, Luton. Beds, England), or a laser diffraction instrument such as a HELOS system (Sympatec, Princeton, NJ). Other instruments for measuring particle geometric diameter are well known in the art. The diameter of respirable dry particles in a sample will range depending upon factors such as particle composition and methods of synthesis. The distribution of size of respirable dry particles in a sample can be selected to permit optimal deposition within targeted sites within the respiratory system.

Experimentally, aerodynamic diameter can be determined using time of flight (TOF) measurements. For example, an instrument such as the Model 3225 Aerosizer DSP Particle Size Analyzer (Amherst Process Instrument, Inc., Amherst, MA) can be used to measure aerodynamic diameter. The Aerosizer measures the time taken for individual respirable dry particles to pass between two fixed laser beams.

Aerodynamic diameter also can be experimentally determined directly using conventional gravitational settling methods, in which the time required for a sample of respirable dry particles to settle a certain distance is measured. Indirect methods for measuring the mass median aerodynamic diameter include the Andersen Cascade Impactor (ACI) and the multi-stage liquid impinger (MSLI) methods. Another method of measuring the aerodynamic diameter is with a Next Generation Impactor (NGI). The NGI operates on similar principles of inertial impaction as the ACI. The NGI consists of seven stages and can be calibrated at flow rates of 30, 60, and 100 LPM. In contrast to the ACI, for which the impactor stages are stacked, the stages of the NGI are all in one plane. Collection cups are used to collect the particles below each stage of the NGI. U.S. Pat. No. 8,614,255. The methods and instruments for measuring particle aerodynamic diameter are well known in the art.

The dry powder of the present formulation comprises substantially dry particles having a mass median aerodynamic diameter (MMAD) within a range of about 0.5 μm to about 10 μm, wherein the dry powder further comprises one or more phospholipids in an amount ranging from about 0.1% (w/w) to about 10% (w/w) of the dry particles. The particles may have an MMAD size distribution where the particles exhibit: (i) a $DV_{90}$ less than about 20 μm, a $DV_{50}$ less than about 7 μm, and a $DV_{10}$ less than about 2 μm; (ii) a $DV_{90}$ less than about 10 μm, a $DV_{50}$ less than about 4 μn, and a $DV_{10}$ less than about 1 μm; or (iii) a $DV_{90}$ less than about 6 μm, a $DV_{50}$ less than about 3 μm, and a $DV_{10}$ less than about 1 μm.

The dry powder may comprise particles coated with a pharmaceutically acceptable excipient. The pharmaceutically acceptable excipient can be a phospholipid having surfactant properties, such as dipalmitoyl phosphatidylcholine (DPPC), distearoyl phosphatidylcholine (DSPC) or soy lecithin, in an amount ranging from about 0.1% to about 10% w/w or in an amount ranging from about 1% to about 5% w/w. In one embodiment, the weight percentage of the DSPC on the dry particles is 5% w/w. In another embodiment, the respirable dry powder of the soy lecithin of the dry particles is 0.1% w/w.

The drug delivery system of the present invention is effective in reducing the risk of a thronboembolic event or treat thrombosis. The dose of acetylsalicylic acid may be present at amounts ranging from about 5 to about 40 mg. The formulation my further comprise clopidogrel. The respirable dry powders can have an emitted dose ranging from about 75% to about 95%.

In one embodiment, the pharmaceutically acceptable excipient is DSPC, the respirable dry powders substantially comprise dry particles having a MMAD ranging from about 3 to about 4 μm and an emitted dose greater than about 90%. In this embodiment, the mass percent of stages in an NGI testing apparatus of the respirable powder yields are at, stage 1 about 10% to about 13%, stage 2, about 20% to about 23%, stage 3, about 13% to about 15%, and stage 4, about 5% to about 6% and fine particle fraction ranges from about 45% to about 55%. Ranges between 80%-120% of actual percentages as set forth above are encompassed within each embodiment.

In another embodiment, the pharmaceutically acceptable excipient is soy lecithin, the respirable dry powders substantially comprise dry particles having a MMAD ranging from about 2.0 to about 3.0 μn and an emitted dose ranging from about 70% to about 85%. In this embodiment, the mass percent of stages in an NGI testing apparatus of the respirable powder yields are at, stage 1 about 5% to about 10%, stage 2, about 10% to about 18%, stage 3, about 15% to about 20%, and stage 4, about 10% to about 15% and fine particle fraction ranges from about 50% to about 70%. Ranges between 80%-120% of actual percentages set forth above are encompassed within each embodiment.

Tap density is a measure of the envelope mass density characterizing a particle. The envelope mass density of a particle of a statistically isotropic shape is defined as the mass of the particle divided by the minimum sphere envelope volume within which it can be enclosed. Features which can contribute to low tap density include irregular surface texture and porous structure. Tap density can be measured by using instruments known to those skilled in the art such as the Dual Platform Microprocessor Controlled Tap Density Tester (Vankel, NC), a GeoPyc™ instrument (Micromeritics Instrument Corp., Norcross, GA), or SOTAX Tap Density Tester model TD2 (SOTAX Corp., Horsham, PA). Tap density can be determined using the method of USP Bulk Density and Tapped Density. United States Pharmacopia convention, Rockville, MD, $10^{th}$ Supplement, 4950-4951, 1999.

Fine particle fraction (FPF) can be used as one way to characterize the aerosol performance of a dispersed powder. Fine particle fraction describes the size distribution of airborne respirable dry particles. Gravimetric analysis, using a Cascade impactor, is one method of measuring the size distribution, or fine particle fraction, of airborne respirable dry particles. The Andersen Cascade Impactor (ACI) is an eight-stage impactor that can separate aerosols into nine distinct fractions based on aerodynamic size. The size cutoffs of each stage are dependent upon the flow rate at which the ACI is operated. The ACI is made up of multiple stages consisting of a series of nozzles (i.e., a jet plate) and an impaction surface (i.e., an impaction disc). At each stage an aerosol stream passes through the nozzles and impinges upon the surface. Respirable dry particles in the aerosol stream with a large enough inertia will impact upon the plate. Smaller respirable dry particles that do not have enough inertia to impact on the plate will remain in the aerosol stream and be carried to the next stage. Each successive stage of the ACI has a higher aerosol velocity in the nozzles so that smaller respirable dry particles can be collected at each successive stage.

If desired, a two-stage collapsed ACI can also be used to measure fine particle fraction. The two-stage collapsed ACI consists of only the top two stages of the eight-stage ACI and allows for the collection of two separate powder fractions. Specifically, a two-stage collapsed ACI is calibrated so that the fraction of powder that is collected on stage one is composed of respirable dry particles that have an aerodynamic diameter of less than 5.6 µm and greater than 3.4 µm. The fraction of powder passing stage one and depositing on a collection filter is thus composed of respirable dry particles having an aerodynamic diameter of less than 3.4 µm. The airflow at such a calibration is approximately 60 L/min. Formulation produced by the methods described herein can be effectively delivered at airflow rates ranging from about 20 L/min to about 60 L/min.

An ACI can be used to approximate the emitted dose, which herein is called gravimetric recovered dose and analytical recovered dose. "Gravimetric recovered dose" is defined as the ratio of the powder weighed on all stage filters of the ACI to the nominal dose. "Analytical recovered dose" is defined as the ratio of the powder recovered from rinsing all stages, all stage filters, and the induction port of the ACI to the nominal dose. The FPF TD (<5.0) is the ratio of the interpolated amount of powder depositing below 5.0 µm on the ACI to the nominal dose. The FPF RD (<5.0) is the ratio of the interpolated amount of powder depositing below 5.0 µm on the ACI to either the gravimetric recovered dose or the analytical recovered dose.

Another way to approximate emitted dose is to determine how much powder leaves its container, e.g. capsule or blister, upon actuation of a dry powder inhaler (DPI). This takes into account the percentage leaving the capsule, but does not take into account any powder depositing on the DPI. The emitted dose is the ratio of the weight of the capsule with the dose before inhaler actuation to the weight of the capsule after inhaler actuation. This measurement can also be called the capsule emitted powder mass (CEPM).

A Multi-Stage Liquid Impinger (MSLI) is another device that can be used to measure particle size distribution or fine particle fraction. The Multi-stage liquid Impinger operates on the same principles as the ACI, although instead of eight stages, MSLI has five. Additionally, each MSLI stage consists of an ethanol-wetted glass frit instead of a solid plate. The wetted stage is used to prevent particle bounce and re-entrainment, which can occur when using the ACI. U.S. Pat. No. 8,614,255.

The subject technology also relates to a respirable dry powder or respirable dry particles produced using any of the methods described herein.

The dry particles of the subject technology can also be characterized by the chemical stability of the salts or the excipients that the dry particles comprise. The chemical stability of the constituent salts can affect important characteristics of the particles including shelf-life, proper storage conditions, acceptable environments for administration, biological compatibility, and effectiveness of the salts. Chemical stability can be assessed using techniques well known in the art. One example of a technique that can be used to assess chemical stability is reverse phase high performance liquid chromatography (RP-HPLC).

If desired, the dry particles and dry powders described herein can be further processed to increase stability. An important characteristic of pharmaceutical dry powders is whether they are stable at different temperature and humidity conditions. Unstable powders will absorb moisture from the environment and agglomerate, thus altering particle size distribution of the powder.

Excipients, such as maltodextrin, may be used to create more stable particles and powders. The maltodextrin may act as an amorphous phase stabilizer and inhibit the components from converting from an amorphous to crystalline state. Alternatively, a post-processing step to help the particles through the crystallization process in a controlled way (e.g., on the baghouse at elevated humidity) can be employed with the resultant powder potentially being further processed to restore their dispersibility if agglomerates formed during the crystallization process, such as by passing the particles through a cyclone to break apart the agglomerates. Another possible approach is to optimize around process conditions that lead to manufacturing particles that are more crystalline and therefore more stable. Another approach is to use different excipients, or different levels of current excipients to attempt to manufacture more stable forms of the salts.

The respirable dry particles and dry powders described herein are suitable for inhalation therapies. The respirable dry particles may be fabricated with the appropriate material, surface roughness, diameter, and tap density for localized delivery to selected regions of the respiratory system such as the deep lung or upper or central airways. For example, higher density or larger respirable dry particles may be used for upper airway delivery, or a mixture of varying size respirable dry particles in a sample, provided with the same or a different formulation, may be administered to target different regions of the lung in one administration.

In order to relate the dispersion of powder at different inhalation flow rates, volumes, and from inhalers of different resistances, the energy required to perform the inhalation maneuver can be calculated. Inhalation energy can be calculated from the equation $E=R^2Q^2V$ where E is the inhalation energy in Joules, R is the inhaler resistance in $kPa^{1/2}$/LPM, Q is the steady flow rate in L/min and V is the inhaled air volume in L.

Healthy adult populations are predicted to be able to achieve inhalation energies ranging from 2.9 to 22 Joules by using values of peak inspiratory flow rate (PIFR) measured by Clarke et al. (Journal of Aerosol Med, 6(2), p. 99-110, 1993) for the flow rate Q from two inhaler resistances of 0.02 and 0.055 kPa1/2/LPM, with a inhalation volume of 2 L based on both FDA guidance documents for dry powder inhalers and on the work of Tiddens et al. (Journal of Aerosol Med, 19, (4), p. 456-465, 2006) who found adults averaging 2.2 L inhaled volume through a variety of DPIs.

Dry powder particles can also be prepared using cone-jet mode of electrohydrodynamic atomization, as described by Li et al., Chemical Engineering Science 61 (2006) 3091-3097. For example, an acetylsalicylic acid solution flowing through a needle can be subjected to an electric field to generate droplets. The method is said to generate a near-monodispersed distribution of droplet relics, leading to form acetylsalicylic acid particulate crystals.

7. Methods of Treatment

In other aspects, the subject technology is a method for treating (including prophylactic treatment or reducing the risk) of a cardiovascular disease (such as thrombosis), comprising administering to the respiratory tract of a subject in need thereof an effective amount of respirable dry particles or dry powder, as described herein.

Cardiovascular diseases include, for example, atherosclerosis, coronary artery disease (CAD), angina pectoris (commonly known as "angina"), thrombosis, ischemic heart disease, coronary insufficiency, peripheral vascular disease, myocardial infarction, cerebrovascular disease (such as stroke), transient ischemic attack, arteriolosclerosis, small vessel disease, elevated cholesterol, intermittent claudication or hypertension.

The respirable dry particles and dry powders can be administered to the respiratory tract of a subject in need thereof using any suitable method, such as instillation techniques, and/or an inhalation device, such as a dry powder inhaler (DPI) or metered dose inhaler (MDI). A number of DPIs are available, such as, the inhalers disclosed is U.S. Pat. Nos. 4,995,385 and 4,069,819, Spinhaler® (Fisons, Loughborough, U.K.), Rotahalers®, Diskhaler® and DiskusZ (GlaxoSmithKline, Research Triangle Technology Park, North Carolina). FlowCapss®, XCaps (Hovione, Loures, Portugal), Inhalators® (BoehringerIngelheim, Gennany), Aerolizer® (Novartis, Switzerland), and others known to those skilled in the art.

Generally, inhalation devices (e.g., DPIs) are able to deliver a maximum amount of dry powder or dry particles in a single inhalation, which is related to the capacity of the blisters, capsules (e.g. size 000, 00, 0E, 0, 1, 2, 3, and 4, with respective volumetric capacities of 1.37 ml, 950 μl, 770 μl, 680 μl, 480 μl, 360 μl, 270 μl, and 200 μl) or other means that contain the dry particles or dry powders within the inhaler. Accordingly, delivery of a desired dose or effective amount may require two or more inhalations. Preferably, each dose that is administered to a subject in need thereof contains an effective amount of respirable dry particles or dry powder and is administered using no more than about 4 inhalations. For example, each dose of respirable dry particles or dry powder can be administered in a single inhalation or 2, 3, or 4 inhalations. The respirable dry particles and dry powders are preferably administered in a single, breath-activated step using a breath-activated DPI. When this type of device is used, the energy of the subject's inhalation both disperses the respirable dry particles and draws them into the respiratory tract.

The respirable dry particles or dry powders can be delivered by inhalation to a desired area within the respiratory tract, as desired. It is well known that particles with an MMAD of about 1 μm to about 3 μm, can be effectively delivered to the deep lung regions such as the alveolar spaces. Larger aerodynamic diameters, for example, from about 3 μm to about 5 μm can be delivered to the central and upper airways.

For dry powder inhalers, oral cavity deposition is dominated by inertial impaction and so characterized by the aerosols Stokes number (DeHaan et aL. Journal of Aerosol Science, 35 (3), 309-331, 2003). For equivalent inhaler geometry, breathing pattern and oral cavity geometry, the Stokes number, and so the oral cavity deposition, is primarily affected by the aerodynamic size of the inhaled powder. Hence, factors that contribute to oral deposition of a powder include the size distribution of the individual particles and the dispersibility of the powder. If the MMAD of the individual particles is too large, e.g. above 5 μm, then an increasing percentage of powder will deposit in the oral cavity. Likewise, if a powder has poor dispersibility, it is an indication that the particles will leave the dry powder inhaler and enter the oral cavity as agglomerates. Agglomerated powder will perform aerodynamically like an individual particle as large as the agglomerate, therefore even if the individual particles are small (e.g., MMAD of about 5 μm or less), the size distribution of the inhaled powder may have an MMAD of greater than about 5 μm, leading to enhanced oral cavity deposition.

Certain embodiments provide a powder in which the particles are small (e.g., MMAD of 5 μm or less, e.g. between about 1 μm to 5 μm), and are highly dispersible (e.g. 1/4 bar or alternatively, 0.5/4 bar of 2.0, and preferably less than 1.5). The respirable dry powder may be comprised of respirable dry particles with an MMAD between 1 to 4 μm or 1 to 3 μm, and have a 1/4 bar less than 1.4, or less than 1.3, and more preferably less than 1.2.

The absolute geometric diameter of the particles measured at 1 bar using the HELOS system is not critical provided that the particle's envelope density is sufficient such that the MMAD is in one of the ranges listed above, wherein MMAD is VMGD times the square root of the envelope density (MMAD=VMGD*sqrt (envelope density)). If it is desired to deliver a high unit dose of salt using a fixed volume-dosing container, then, particles of higher envelop density are desired. High envelope density allows for more mass of powder to be contained within the fixed volume-dosing container. Preferable envelope densities are greater than 0.1 g/cm$^3$, greater than 0.25 g/cm$^3$, greater than 0.4 g/cm$^3$, greater than 0.5 g/cm$^3$, and greater than 0.6 g/cm$^3$.

The respirable dry powders and particles of the subject technology can be employed in compositions suitable for drug delivery via the respiratory system. For example, such compositions can include blends of the respirable dry particles of the subject technology and one or more other dry particles or powders, such as dry particles or powders that contain another active agent, or that consist of or consist essentially of one or more pharmaceutically acceptable excipients.

Respirable dry powders and dry particles suitable for use in the methods of the subject technology can travel through the upper airways (i.e., the oropharynx and larynx), the lower airways, which include the trachea followed by bifurcations into the bronchi and bronchioli, and through the terminal bronchioli which in turn divide into respiratory bronchiole leading then to the ultimate respiratory zone, the alveoli or the deep lung. In one embodiment of the subject technology, most of the mass of respirable dry powders or particles deposit in the deep lung. In another embodiment of the subject technology, delivery is primarily to the central airways. In another embodiment, delivery is to the upper airways.

The respirable dry particles or dry powders of the subject technology can be delivered by inhalation at various parts of the breathing cycle (e.g., laminar flow at mid-breath). An advantage of the high dispersibility of the dry powders and dry particles of the subject technology is the ability to target deposition in the respiratory tract. For example, breath controlled delivery of nebulized solutions is a recent development in liquid aerosol delivery (Dalby et a, in Inhalation Aerosols, edited by Hickey 2007, p. 437). In this case, nebulized droplets are released only during certain portions of the breathing cycle. For deep lung delivery, droplets are released in the beginning of the inhalation cycle, while for central airway deposition, they are released later in the inhalation.

The dry powders of this subject technology provide advantages for targeting the timing of drug delivery in the breathing cycle and also location in the human lung. Because the respirable dry powders of the subject technology can be dispersed rapidly, such as within a fraction of a typical inhalation maneuver, the timing of the powder dispersal can be controlled to deliver an aerosol at specific times within the inhalation.

With a highly dispersible powder, the complete dose of aerosol can be dispersed at the beginning portion of the inhalation. While the patient's inhalation flow rate ramps up to the peak inspiratory flow rate, a highly dispersible powder will begin to disperse already at the beginning of the ramp up and could completely disperse a dose in the first portion of the inhalation. Since the air that is inhaled at the beginning of the inhalation will ventilate deepest into the lungs, dispersing the most aerosol into the first part of the inhalation is preferable for deep lung deposition. Similarly, for central deposition, dispersing the aerosol at a high concentration into the air which will ventilate the central airways can be achieved by rapid dispersion of the dose near the mid to end of the inhalation. This can be accomplished by a number of mechanical and other means such as a switch operated by time, pressure or flow rate that diverts the patient's inhaled air to the powder to be dispersed only after the switch conditions are met.

Aerosol dosage, formulations and delivery systems may be selected for a particular therapeutic application, as described, for example, in Gonda, I. "Aerosols for delivery of therapeutic and diagnostic agents to the respiratory tract," in Critical Reviews in Therapeutic Drug Carrier Systems, 6: 273-313 (1990); and in Moren, "Aerosol Dosage Forms and Formulations." in Aerosols in Medicine. Principles, Diagnosis and Therapy, Moren, et al., Eds., Esevier, Amsterdam (1985).

Suitable intervals between doses that provide the desired therapeutic effect can be determined based on the severity of the condition, overall well-being of the subject and the subjects tolerance to respirable dry particles and dry powders and other considerations. Based on these and other considerations, a clinician can determine appropriate intervals between doses. Respirable dry particles and dry powders may be administered once, twice or three times a day or on an as needed basis.

In various embodiments the amount of NSAID, such as acetylsalicyclic acid, delivered to the respiratory tract (e.g., lungs, respiratory airway) is about 0.001 mg/kg body weight/dose to about 2 mg/kg body weight/dose, about 0.002 mg/kg body weight/dose to about 2 mg/kg body weight/dose, about 0.005 mg/kg body weight/dose to about 2 mg/kg body weight/dose, about 0.01 mg/kg body weight/dose to about 2 mg/kg body weight/dose, about 0.02 mg/kg body weight/dose to about 2 mg/kg body weight/dose, about 0.05 mg/kg body weight/dose to about 2 mg/kg body weight/dose, about 0.075 mg/kg body weight/dose to about 2 mg/kg body weight/dose, about 0.1 mg/kg body weight/dose to about 2 mg/kg body weight/dose, about 0.2 mg/kg body weight/dose to about 2 mg/kg body weight/dose, about 0.5 mg/kg body weight/dose to about 2 mg/kg body weight/dose, or about 0.75 mg/kg body weight/dose to about 2 mg/kg body weight/dose.

In certain embodiments, at least about 50%, at least about 60%, at least about 70%, at least about 75%, at least about 80%, at least about 85%, at least about 90%, at least about 95%, or at least about 99%, of the administered acetylsalicylic acid reaches the systemic circulation of a subject within about 60 minutes upon administration, or within about 40 minutes upon administration, or within about 30 minutes upon administration, or within about 20 minutes upon administration, or within about 15 minutes upon administration, or within about 5 minutes upon administration.

The dosing of acetylsalicyclic acid may be adjusted so that PGI2 synthesis capacity of the nasal, bronchial or pulmonary epithelial of endothelial cells, including nasal mucosa cells, is not inhibited.

In certain embodiments, the method and delivery devices described herein can deliver acetylsalicylic acid, and pharmacologically active metabolic byproducts of acetylsalicylic acid thereof, to the systemic circulation, at levels that are substantially the same, or higher as compared to those delivered by oral administration of about 30 mg of acetylsalicylic acid, about 40 mg of acetylsalicylic acid, about 50 mg of acetylsalicylic acid, about 80 mg of acetylsalicylic acid or about 160 mg of acetylsalicylic acid.

The doses of acetylsalicylic acid administered in order to achieve a level (or an average level among a population of patients) that is substantially the same, or higher as compared to those delivered by oral administration of about 30 mg, about 40 mg, about 50 mg, about 80 mg, or about 160 mg of acetylsalicylic acid can be determined by conventional methods. The dosing, administration techniques and schedules are known in the art and are within the ability of the skilled clinician. For example, the serum level of acetylsalicylic acid, or a metabolite thereof, in a subject (or average serum level among a population of subjects) can be determined by conventional pharmacokinetic or pharmacodynamics studies.

In certain embodiments, the method and delivery devices described herein can deliver acetylsalicylic acid to the systemic circulation such that the circulating plasma level of acetylsalicylic acid is at least about 1 μg/mL, at least about 2 μg/mL, at least about 3 μg/mL, at least about 4 μg/mL, at least about 5 μg/mL, oat least about 6 μg/mL, within about 60 minutes upon administration, or within about 40 minutes upon administration, or within about 30 minutes upon administration, or within about 20 minutes upon administration, or within about 15 minutes upon administration, or within about 5 minutes upon administration.

In other embodiments, the method and delivery devices described herein can deliver acetylsalicylic acid to the systemic circulation such that circulating plasma level of salicylate is about 8 μg/mL, about 9 μg/mL, about 10 μg/mL, about 11 μg/mL, about 12 μg/mL, or about 15 μg/mL, within about 60 minutes upon administration, or within about 40 minutes upon administration, or within about 30 minutes upon administration, or within about 20 minutes upon administration, or within about 15 minutes upon administration, or within about 5 minutes upon administration.

If desired or indicated, the respirable dry particles and dry powders described herein can be administered with one or more other therapeutic agents. The other therapeutic agents can be administered by any suitable route, such as orally, parenterally (e.g., intravenous, intraarterial, intramuscular, or subcutaneous injection), topically, by inhalation (e.g., intrabronchial, intranasal or oral inhalation, intranasal drops), rectally, vaginally, and the like. The respirable dry particles and dry powders can be administered before, substantially concurrently with, or subsequent to administration of the other therapeutic agent. Preferably, the respirable dry particles and dry powders and the other therapeutic agent are administered so as to provide substantial overlap of their pharmacologic activities.

The following examples of specific aspects for carrying out the present invention are offered for illustrative purposes only, and are not intended to limit the scope of the present invention in any way.

Example 1 Development of Acetylsalicylic Acid Particles for Inhalation

This study was designed to develop phospholipid coated acetylsalicylic acid particles with particle size less than 2.0 μm for deep lung tissue delivery. This development work was carried out to achieve following target particle size: Dv50 of 0.5 nm to 2.0 μm; Dv90 of 1.5 to 2.0 μm.

Jet milling was selected as a method for micronization of acetylsalicylic acid particles to achieve target particle size. Jet milling operation was successfully reproduced with Dv50s of 0.4 μm and Dv90s of 1.3 μm and 1.6 μm for the two batches manufactured. Micronized particles were then spray-dried using DSPC (1,2-distearoyl-(sn)-glycero-3-phosphocholine) or soy lecithin to reduce particle agglomeration and irritation on inhalation. 79% yield for DSPC/acetylsalicylic acid and 54% yield for soy lecithin/acetylsalicylic acid were obtained.

Particle size analysis at each step was carried out. Spray-dried DSPC/acetylsalicylic acid particles ranged from 1.8 to 3.6 μm and lecithin/acetylsalicylic acid particles ranged from 1.7 to 3.3 μm.

DSC studies showed no change in the crystalline structure of acetylsalicylic acid before and after spray-drying with DSPC. TGA showed 0.6% moisture content for both pre- and post-spray-dried particles indicating absence of any residual solvent after spray-drying.

Formulation Development

1. Acetylsalicylic Acid

Rhodine 3040 US obtained from Rhodia Inc. was used for all experiments. Particles were dispersed in 0.1% w/w docusate sodium in water and observed under a light microscope to confirm particle size. Particles ranging from 66 to 280 μm were observed confirming data from certificate of analysis, though observed "rounding" of the particulates is indicative of partial dissolution in the aqueous dispersant.

2. Particle Size Analysis

Particle size analysis was carried out using laser diffraction and light microscopy.

2.1. Laser Diffraction

Horiba LA-950 V2 with fraction cell was used for laser diffraction studies using the following parameters: dispersion media: 0.05% w/w soy lecithin dissolved in n-hexane; refractive index of media: 1.334; refractive index of acetylsalicylic acid particles: 1.5623; i-value: 0.01. The i-value is an imaginary component that is used by the laser diffraction algorithm to account for the absorption of light by the particles. A stock dispersion of particles in the same media was prepared and added drop-wise to the fraction cell containing a magnetic stirrer bar until the intensity meter showed red laser between 80% and 90%, while blue laser was between 70% and 90%. Once stabilized, the volumetric mean diameter Dv10, Dv50 and Dv90 were measured. This laser diffraction method developed for uncoated particles was not used for spray-dried phospholipid/acetylsalicylic acid particles as they did not disperse well in the selected media.

2.2 Light Microscopy

Photomicrographs of the pre- and post-micronized uncoated particles were taken by dispersing them in a solution of 0.1% w/w docusate sodium in purified water USP, and using a digital imaging light microscope (Olympus BX51 with Clemex ST-2000 controller) at 400-times or 1000-times magnification. As spray-dried phospholipid/acetylsalicylic acid particles were found to not disperse well in the selected media, photomicrographs were taken after spreading them in the dry state over glass slides.

3. Jet Milling Trials Using Sturtevant Qualification Mill

Initial work was carried out using a Sturtevant Qualification mill with venturi #1 using nitrogen as the carrier gas. Material was fed through vibratory feeder at controlled rate and at predetermined feed and grind pressure. The effect of grinding pressure, feed rate, and second pass were studied on particle size reduction and the conditions are reported in Table 4.

TABLE 4

Jet Milling Trials using Sturtevant Qualification Mill

| Formulation Milling run | 3694 Pass#1 | 3695 Pass#1 | 3701 Pass#1 | 3702 Pass#2 of Formulation 3695 |
|---|---|---|---|---|
| P_Feed (bar) | 7 | 7 | 7 | 7 |
| P_Grind (bar) | 3.5 | 5 | 3.5 | 5 |
| F_Flow (g/hr) | 17 | 17 | 54 | 7 |

3.1 Effect of Grind Pressure

Formulations 3694 and 3695 were compared to study effect of grind pressure on PSD (particle size distribution). Laser diffraction and microscopy results were obtained are presented in Table 5. Microscopy and laser diffraction data were found to correlate very well. When grinding pressure was increased from 3.5 to 5 bar, a measurable decrease in particle size was observed as would be expected.

TABLE 5

Effect of Grind Pressure on Acetylsalicylic acid Particle Size

| | Average (% RSD)/n = 3 | |
|---|---|---|
| Formulation | 3694 | 3895 |
| Dv10 (μm) | 1.9 (1.0) | 1.2 (2.2) |
| Dv50 (μm) | 3.3 (1.8) | 2.4 (1.9) |
| Dv90 (μm) | 5.9 (2.8) | 4.9 (2.6) |
| Microscopy (μm) | 1.7-5.1 | 2.0-3.5 |

3.2 Effect of Feed Rate

Formulations 3694 and 3701 were compared to study the effect of material feed rate on particle size using microscopy (Table 6). Clearly, as the flow rate was increased from 17 g/hr to 54 g/hr, significantly larger particles were obtained. This is likely the result of new material entering the milling chamber and pushing out particles to the collection bag before they undergo sufficient attrition.

TABLE 6

Effect of Feed Rate on Particle Size

| Formulation | 3694 | 3701 |
|---|---|---|
| Microscopy (μm) | 1.7-5.1 | 5.2-42.1 |

3.3 Effect of Second Milling Pass

In order to achieve the target particle size of Dv50 of 1.5 μm and Dv90 of 2 μm, formulation 3695 was passed the through mill for a second pass. Particle size analysis was carried out using laser diffraction and microscopy (Table 7). Significant particle size reduction was achieved on the second pass through the jet mill which implies that acetylsalicylic acid particles undergo first order size reduction, and that final particle size obtained depends upon initial particle size used.

TABLE 7

Effect of Second Milling Pass on Particle Size

| Formulation | 3695 | 3702 |
|---|---|---|
| Microscopy (μm) | 2.0-3.5 | 0.8-2.4 |

4. Jet Milling Using Sturtevant Sanitary Design Mill

In order to achieve higher feed rate with better control as well as to increase batch size, the larger 2" sanitary design mill was used according to parameters listed in Table 8. Material was processed on a second pass as well to reduce particle size to target. Formulations 3727 and 3734 were compared with 3705 and 3725 processed using the Qualification mill respectively to study reproducibility in PSD. An antistatic device was necessary to feed the powder for the second pass to minimize the effects of the static electricity imparted during the first pass.

TABLE 8

Jet Milling using Sturtevant Sanitary Design Mill
Aggregated particles with high static charge were obtained in all cases.

| | Q-Mill | | 2" Mill | |
|---|---|---|---|---|
| Mill Used | | 3725 | | 3734 |
| | | Pass #2 | | Pass #2 |
| Formulation | 3705 | (Formulation | 3727 | (Formulation |
| Milling run | Pass #1 | 3705) | Pass #1 | 3727) |
| P_Venturi (bar) | 4.1 | 2.8 | 4.1 | 2.9 |
| P_Grind (bar) | 2.8 | 2.1 | 2.8 | 2.1 |
| F_Flow (g/hr) | 132 | 78 | 142 | 59 |
| Batch size (g) | 80 | 50 | 200 | 120 |

Aggregated particles with high static charge were obtained in all cases.

4.1 Particle Size Analysis

Figure 2:
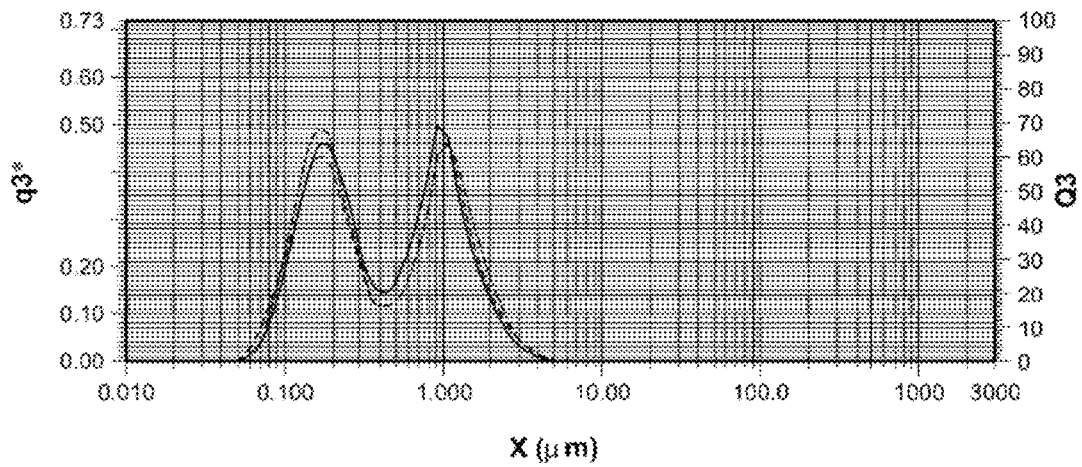
FIG. 2 shows laser diffraction data of Formulation 3734.

Particle size analysis of above formulations was carried out using laser diffraction and microscopy (Table 9, FIG. 1 and FIG. 2). Reproducible results in particle size reduction were obtained with comparable Dv10, Dv50 and Dv90 values between the two mill sizes, even with batch size increased from 80 g to 200 g for the first pass and from 50 g to 120 g for the second pass. Monomodal PSD was obtained for the first pass while a bimodal distribution was observed for the second pass.

TABLE 9

Particle Size Analysis of Jet Milled Acetylsalicylic Acid
Formulations Prepared Using Sanitary Design Mill

| | Average (% RSD)/n = 3 | | | |
|---|---|---|---|---|
| Formulation | 3705 | 3725 | 3727 | 3734 |
| Dv10 (μm) | 0.9 (5.2) | 0.1 (1.9) | 0.8 (10.0) | 0.1 (1.6) |
| Dv50 (μm) | 1.5 (3.3) | 0.4 (6.3) | 1.3 (5.2) | 0.4 (12.9) |

TABLE 9-continued

Particle Size Analysis of Jet Milled Acetylsalicylic Acid
Formulations Prepared Using Sanitary Design Mill

| | Average (% RSD)/n = 3 | | | |
|---|---|---|---|---|
| Formulation | 3705 | 3725 | 3727 | 3734 |
| Dv90 (μm) | 2.6 (4.2) | 1.8 (6.0) | 2.2 (8.7) | 1.5 (5.1) |
| Microscopy | 1.2-2.6 μm | 0.9-1.8 μm | 1.1-3.2 μm | 0.9-2.3 μm |

5. Coating

Spray-drying was used for coating. Jet milled formulation 3734, processed two passes on the 2" sanitary mill, was used further to coat with either DSPC or soy lecithin. Particles were dispersed in n-hexane containing lipid and spray-drying was selected as a method to remove solvent. In order to achieve coating around all individual particles, it was required to disperse Jet milled particles completely without settling, and therefore, continuous stirring was employed throughout the spray-drying operation.

5% w/w DSPC was used as it was found from previous work to mitigate irritation when inhaled. Additionally, soy lecithin was also used in the concentration of 0.1% w/w. As acetylsalicylic acid is insoluble in n-hexane, it was selected as a dispersion media for the micronized particles. Also, it has boiling point of 70° C. which is much below the melting point of acetylsalicylic acid (~135° C.) and therefore, an inlet temperature of 85° C. should remove solvent without affecting the acetylsalicylic acid particles.

A Buchi-290 spray dryer equipped with nozzle of 0.7 mm diameter was used for the study. Spray-drying was performed using nitrogen as the carrier gas with the aspirator set at 100% capacity. The flow rate of nitrogen was adjusted to 1052 L/hr (50 mm in rotameter). Before feeding the stock dispersion, feed rate was adjusted using dispersing media alone to achieve targeted outlet temperature and stabilization of the system.

5.1 Spray-Drying Using DSPC

DSPC (Lipoid PC 18:0/18:0) is an endogenous lung phospholipid with a phase transition temperature of 55° C. On heating at this temperature, DSPC transforms into a liquid crystalline phase from the gel phase, and the phospholipid layer is dispersed in n-hexane as a monolayer with a random and non-rigid structure. When jet milled acetylsalicylic acid particles are dispersed in the DSPC/Hexane solution, a well dispersed colloidal suspension was formed without noticeable settling. From this, it was hypothesized that spray-drying should be able to coat individual acetylsalicylic acid particles on solvent removal. Details of the processing are reported in Table 10.

TABLE 10

Spray-Drying Parameters for DSPC/Acetylsalicylic acid Formulation

| Formulation | 3739 |
|---|---|
| Suspension preparation | |
| DSPC (g) | 0.50 |
| n-hexane (g) | 490 |
| Jet milled ASA (g) | 9.50 |
| % Solid in feed | 2 |
| Suspension temperature (° C.) | 55 |
| Spray-drying parameters | |
| Inlet temperature (° C.) | 85 |

TABLE 10-continued

Spray-Drying Parameters for DSPC/Acetylsalicylic acid Formulation

| Formulation | 3739 |
|---|---|
| Outlet temperature (° C.) | 56 |
| Flow rate (g/min) | 3.9 |
| Flow meter (mm) | 50 |
| Suspension temperature (° C.) | 55 |
| % Yield | 79 |

No excessive sticking to the spray-drying chamber was observed during processing and a yield of 79% was obtained. Also, the coated particles obtained were observed to be denser and less static than uncoated particles.

5.1.1 Particle Size Analysis

The spray-dried DSPC coated particles were found to not disperse as well in the 0.05% w/w soy lecithin/n-hexane solution used for particle size analysis of the uncoated acetylsalicylic acid particles. Some agglomeration was observed by microscopy compared to uncoated, though PSD ranges of the primary particles was collated from the microscopic images (Table 11).

TABLE 11

Particle Size of Micronized Uncoated and Spray-Dried DSPC/Acetylsalicylic acid Particles

| Formulation | 3734 | 3739 |
|---|---|---|
| Description | Micronized uncoated | Spray-dried DSPC/aspirin |
| Microscopy (μm) | 0.9-2.3 | 1.8-3.6 |

5.1.2 Differential Scanning Calorimetry (DSC)

A DSC study was carried out on raw acetylsalicylic acid, uncoated milled particles of formulation 3734 and spray-dried DSPC/acetylsalicylic acid particles of formulation 3739 to study any change in the crystallinity of the acetylsalicylic acid induced from processing.

Samples were sealed in 40 μL aluminum pans with pierced lids and analyzed using a differential scanning calorimeter (Mettler-Toledo DSC equipped with STAR® software V10.00). The samples were heated from 25° C. to 160° C. at a rate of 10° C. per minute. An empty pan served as the reference.

Figure 3:
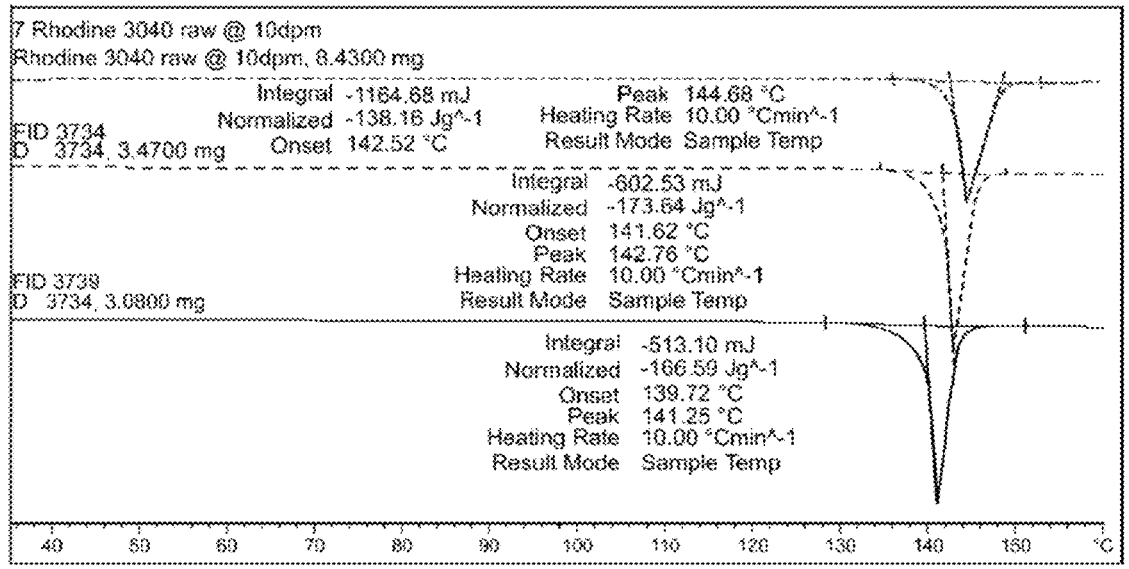
FIG. 3 shows DSC thermograms of raw, micronized uncoated and spray-dried DSPC/acetylsalicylic acid particles.

In all samples, a sharp endothermic peak corresponding to acetylsalicylic acid melting was observed. No other polymorphic conversion was observed. Also, no significant shift in peak was observed confirming no change in crystallinity of the acetylsalicylic acid on processing (FIG. 3, Table 12).

TABLE 12

DSC Analysis of Raw, Micronized Uncoated and Spray-Dried DSPC/Acetylsalicylic acid Particles

| Sample | Onset temperature (°C) | Peak temperature (°C) |
|---|---|---|
| Rhodine 3040 US raw | 142.5 | 144.7 |
| Micronized uncoated aspirin | 141.6 | 142.8 |
| Spray-dried DSPC/aspirin | 139.7 | 141.3 |

5.1.3 Thermogravimetric Analysis (TGA)

TGA was carried out for the micronized uncoated acetylsalicylic acid particles of formulation 3734 and spray-dried DSPC % acetylsalicylic acid particles of formulation 3739 to evaluate those for residual solvent and change in moisture content of the particles on spray-drying.

TGA of spray-dried powder carried out in 40 μL aluminum open pans by heating them from 25° C. to 160° C. at a rate of 10° C. per minute using Mettler-Toledo TGA/DSC1 equipped with STARS software V10.00. The % weight loss was measured from 25° C. to 120° C. and compared between pre- and post-spray-drying.

Figure 4:
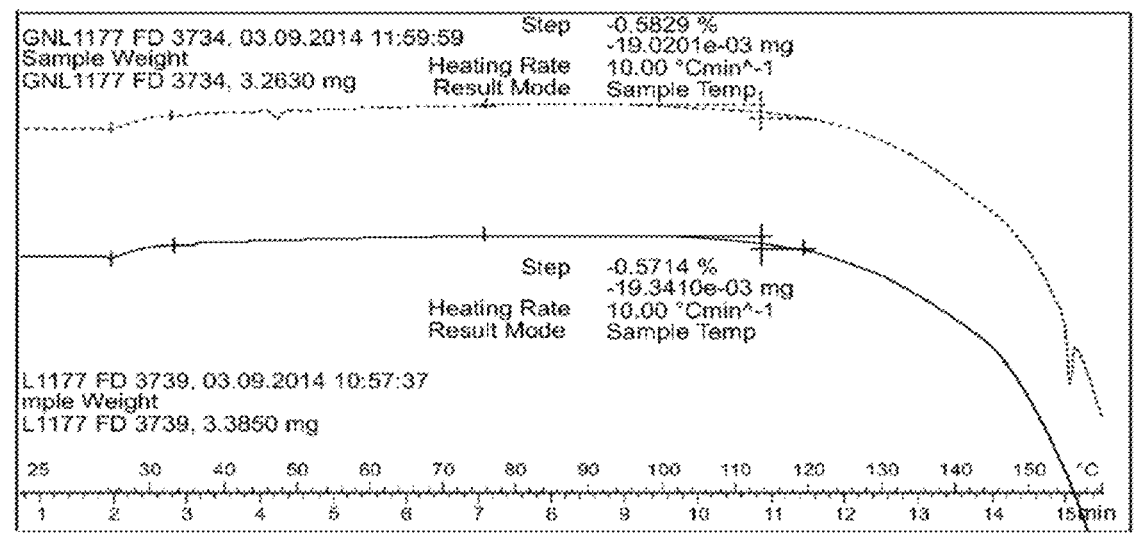
FIG. 4 shows TGA of micronized uncoated and spray-dried DSPC/acetylsalicylic acid particles.
Figure 5A:
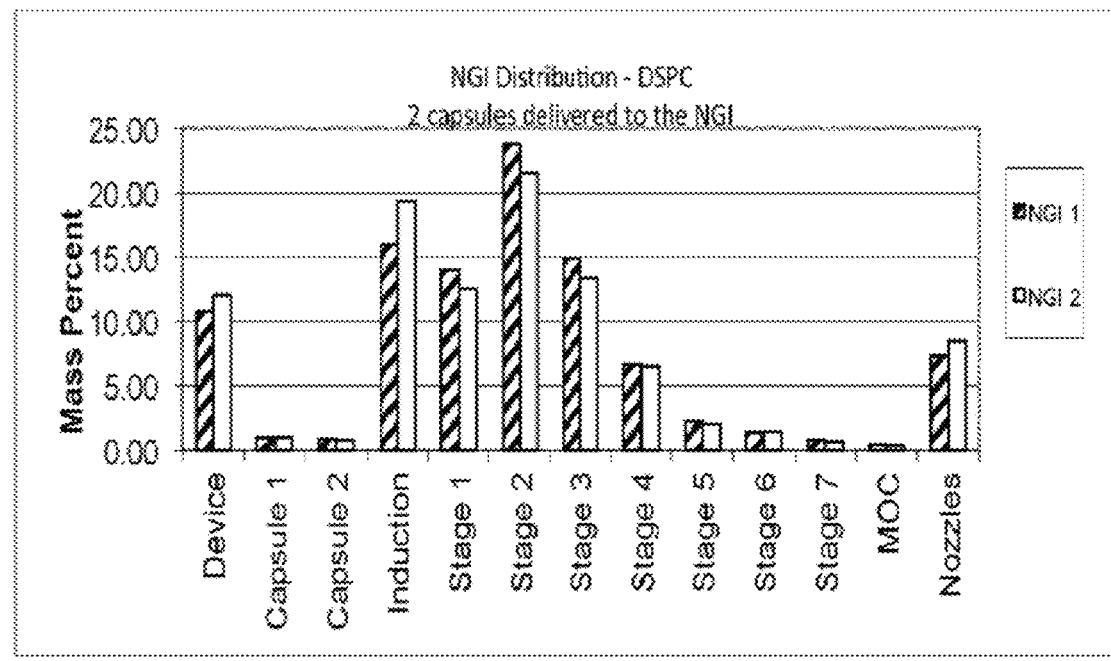
FIGS. 5A and 5B show the particle size distribution of spray-dried DSPC/acetylsalicylic acid particles based on NGI analysis.
Figure 5B:
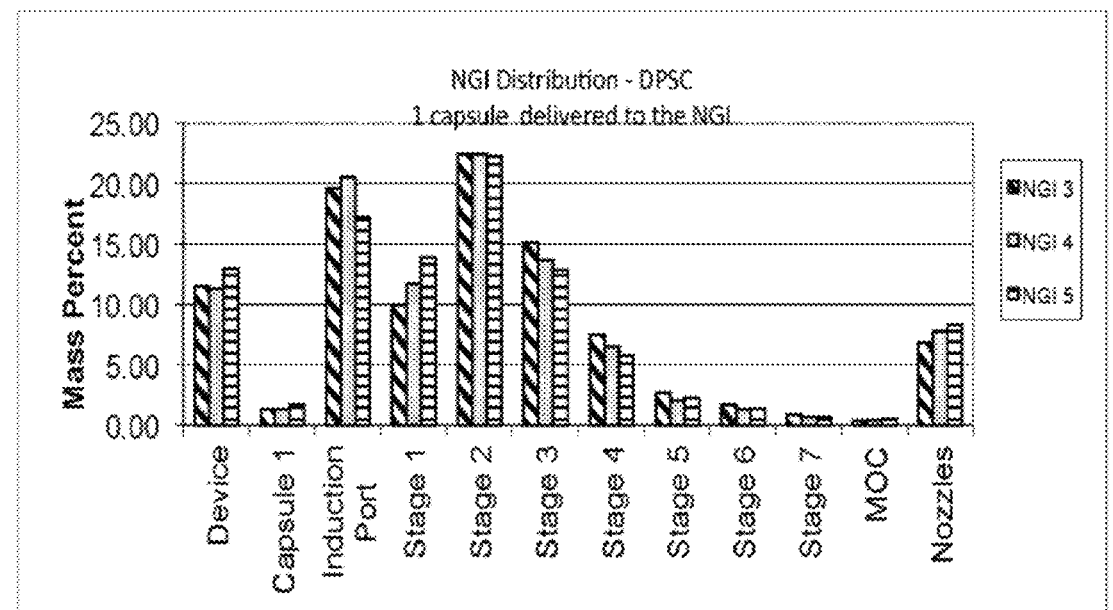
Figure 6A:
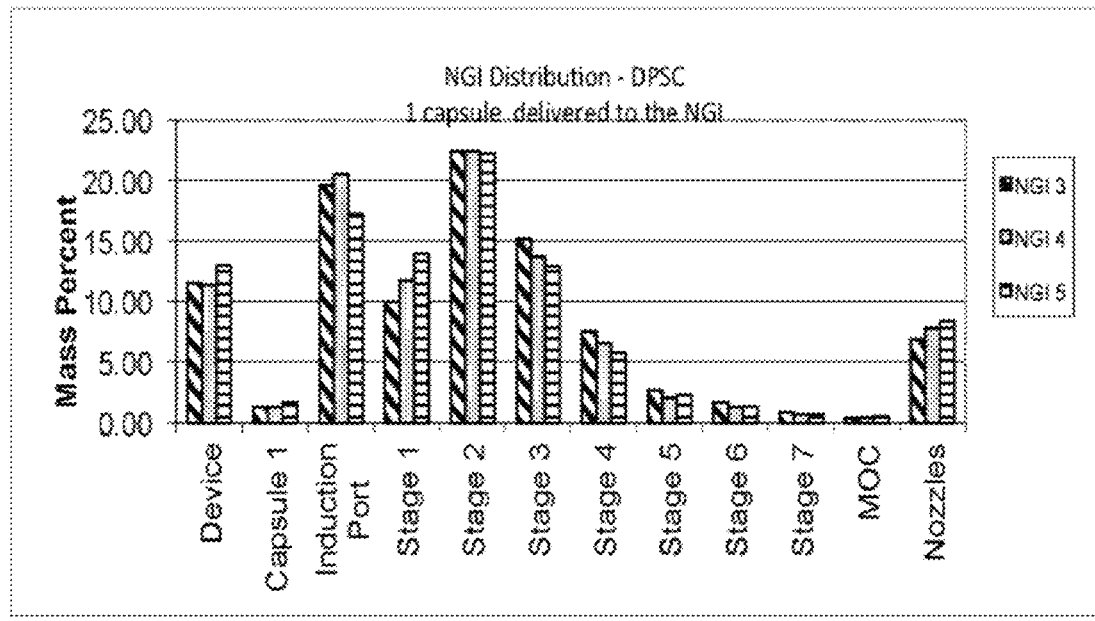
FIGS. 6A and 6B show the particle size distribution of spray-dried soy lecithin/acetylsalicylic acid particles based on NGI analysis.
Figure 6B:
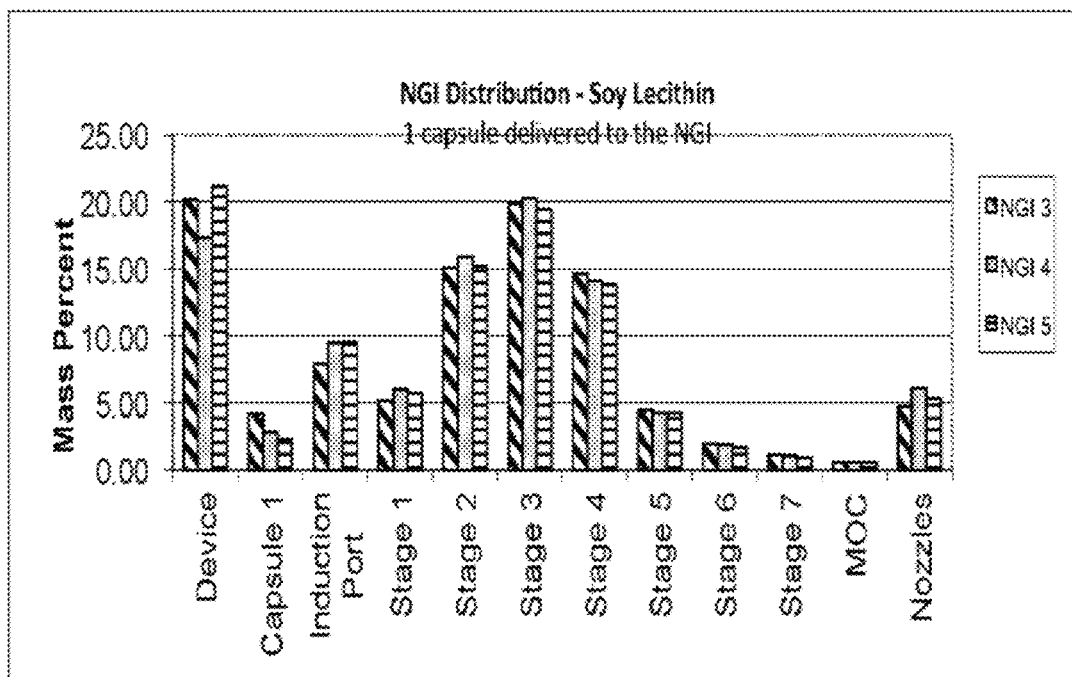

TGA data suggests that there is no residual hexane in spray-dried particles, as the % weight loss before and after spray drying show similar values. The 0.57% weight loss is likely indicative of the moisture content of pre- and post-spray-dried acetylsalicylic acid particles (FIG. 4, Table 13).

TABLE 13

% Weight Loss for Micronized Uncoated and Spray-Dried DSPC/Acetylsalicylic acid Particles

| Formulation | weight loss (g) |
|---|---|
| Micronized uncoated aspirin | 0.58 |
| Spray-dried DSPC/aspirin | 0.57 |

5.2 Spray-Drying Acetylsalicylic Acid Particles Using Soy Lecithin

Soy lecithin was selected as an excipient as it is also approved for inhalation drug delivery and it was able to disperse jet milled acetylsalicylic acid particles well. Therefore, it was expected to be able to coat individual acetylsalicylic acid particle on solvent removal. Soy lecithin was dissolved in n-hexane and jet milled acetylsalicylic acid particles dispersed in it with stirring. However, unlike the dispersion of acetylsalicylic acid in DSPC, the soy lecithin in 0.1% w/w concentration was not able to form colloidal dispersion, and some settling was observed. Therefore, continuous stirring of the feed suspension during spray-drying was used to maintain the dispersion of the acetylsalicylic acid particles. Spray-drying was carried out to remove n-hexane and coat acetylsalicylic acid particles using the parameters in Table 14. A 54% yield was obtained.

TABLE 14

Spray-Drying Parameters for Soy Lecithin/Acetylsalicylic acid Formulation

| Formulation | 3740 |
|---|---|
| Suspension preparation | |
| Soy lecithin (g) | 0.01 |
| n-hexane (g) | 490 |
| Jet milled ASA (g) | 9.99 |
| % Solid in feed | 2 |
| Suspension temperature (° C.) | RT |
| Spray-drying parameters | |
| Inlet temperature (° C.) | 85 |
| Outlet temperature (° C.) | 59 |
| Flow rate (g/min) | 3.9 |
| Flow meter (mm) | 50 |
| Suspension temperature | RT |
| Yield | 54% |

5.2.1 Particle Size Analysis

Particle size analysis was carried out using powder microscopy and compared with micronized uncoated and spray-dried DSPC/acetylsalicylic acid. Particle size of both spray-dried formulations suggest satisfactory results (Table 15).

TABLE 15

Particle Size Analysis of Spray-dried Soy Lecithin/Acetylsalicylic acid Particles

| Formulation Description | 3734 Micronized uncoated aspirin | 3739 Spray-dried DSPC/aspirin | 3740 Spray-dried soy lecithin/Aspirin |
|---|---|---|---|
| Microscopy (μm) | 0.9-2.3 | 1.8-3.6 | 1.7-3.3 |

CONCLUSIONS

The micronization of acetylsalicylic acid yielded an approximately 70 fold reduction in the starting particle size. Spray-drying with DSPC or soy lecithin resulted in satisfactory particle size for deep lung tissue drug delivery with maximum size of 3.6 μm. Spray-dried DSPC/acetylsalicylic acid particles were found to be less static than soy lecithin/acetylsalicylic acid particles, and even less static than micronized uncoated acetylsalicylic acid particles. The crystalline structure of acetylsalicylic acid did not change during milling or spray drying as observed by DSC study. DSC studies also suggested absence of any other event such as polymorph conversion during processing. No traces of residual solvent found in spray dried DSPC/acetylsalicylic acid during TGA analysis.

Example 2 Emitted Dose Analysis of DSPC/Acetylsalicylc Acid Particles and Soy Lecithin/Acetylsalicylc Acid Particles DPI devices, e.g. Plastiape, were used to evaluate emitted doses of the DSPC/acetylsalicylic acid particles and soy lecithin/acetylsalicylic acid particles.

TABLE 16

| Powder Type | DPI Device | Flow Rate (slpm) | Fill Weight (mg) | Initial Device Weight (g) | Final Device Weight (g) | Total Emitted Dose (mg) | % Emitted (based on fill weight) |
|---|---|---|---|---|---|---|---|
| Acetylsalicylic acid (Soy Lecithin) | Plastiape | 100.0 | 20.11 | 10.49661 | 10.48124 | 15.37 | 76.4 |
| Acetylsalicylic acid (Soy Lecithin) | Plastiape | 100.0 | 32.81 | 10.55421 | 10.53301 | 21.20 | 64.6 |

Lactose was used to test proper de-vice setup.

Example 3 Particle Size Distribution (PSD) Analysis of Inhaled Acetylsalicylic Acid by Dry Dispersion and Laser Diffraction Particle size analysis was carried out using laser diffraction analysis of dry dispersed spray-dried DSPC/acetylsalicylic acid particles of formulation 3739 (Table 17), and spray-dried soy lecithin/acetylsalicylic acid particles formulation 3740 (Table 18) (see Example 1 for the preparation of DSPC/acetylsalicylic acid particles and soy lecithin/acetylsalicylic acid particles).

TABLE 17

| Lens | Primary Pressure (bar) | Replicate | Particle Size (μm) | | | | | Optical Conc. |
|---|---|---|---|---|---|---|---|---|
| | | | X10 | X50 | X90 | VMD | GSD | |
| R3 | 1.0 | 1 | 0.96 | 2.29 | 4.47 | 2.56 | 1.82 | 8.71 |
| R2 | 1.0 | 1 | 0.83 | 2.31 | 4.49 | 2.56 | 1.90 | 7.56 |
| | | 2 | 0.79 | 2.24 | 4.44 | 2.49 | 1.93 | 7.10 |
| R1 | 0.7 | 1 | 0.66 | 2.63 | 5.27 | 2.88 | 2.07 | 9.21 |
| | | 2 | 0.64 | 2.59 | 5.18 | 2.84 | 2.07 | 5.72 |
| | 0.9 | 1 | 0.62 | 2.34 | 4.63 | 2.57 | 2.01 | 4.78 |
| | | 2 | 0.57 | 2.31 | 4.68 | 2.55 | 2.09 | 5.98 |
| | 1.0 | 1 | 0.58 | 2.31 | 4.69 | 2.54 | 2.11 | 10.98 |
| | | 2 | 0.60 | 2.34 | 4.69 | 2.56 | 2.08 | 6.53 |
| | | 3 | 0.56 | 2.31 | 4.76 | 2.57 | 2.14 | 6.74 |
| | | 4 | 0.57 | 2.26 | 4.51 | 2.48 | 2.07 | 7.97 |
| | | 5 | 0.58 | 2.28 | 4.53 | 2.49 | 2.06 | 8.20 |
| | 1.2 | 1 | 0.56 | 2.13 | 4.17 | 2.32 | 2.03 | 4.38 |
| | | 2 | 0.55 | 2.12 | 4.17 | 2.32 | 2.05 | 12.60 |
| | 2.0 | 1 | 0.60 | 2.03 | 4.03 | 2.54 | 1.97 | 6.03 |
| | | 2 | 0.54 | 2.03 | 4.25 | 2.57 | 2.12 | 7.63 |
| | 3.0 | 1 | 0.55 | 1.84 | 3.68 | 2.13 | 2.03 | 8.88 |
| | | 2 | 0.52 | 1.81 | 3.63 | 2.01 | 2.07 | 8.49 |
| | 4.0 | 1 | 0.47 | 1.79 | 3.64 | 2.00 | 2.12 | 6.41 |
| | | 2 | 0.52 | 1.80 | 3.58 | 2.00 | 2.03 | 7.56 |

TABLE 18

| Lens | Primary Pressure (bar) | Replicate | Particle Size (μm) | | | | | Optical Conc. |
|---|---|---|---|---|---|---|---|---|
| | | | X10 | X50 | X90 | VMD | GSD | |
| R1 | 1.0 | 1 | 0.50 | 1.91 | 3.90 | 2.12 | 2.11 | 11.28 |
| | | 2 | 0.50 | 1.89 | 3.73 | 2.07 | 2.03 | 3.89 |
| | | 3 | 0.49 | 1.90 | 3.83 | 2.11 | 2.09 | 9.58 |
| | | 4 | 0.52 | 1.90 | 3.66 | 2.06 | 2.00 | 4.70 |
| | | 5 | 0.49 | 1.90 | 3.83 | 2.10 | 2.08 | 6.84 |
| | | Average % RSD | 0.502 | 1.900 | 3.792 | 2.091 | 2.062 | |

RSD: relative standard deviation.

Example 4 NGI (Next-Generation Impactor) Analysis of Spray Dried Acetylsalicylic Acid/DPSC Particles The dry powders of Example 1 were evaluated for aerodynamic performance. The DPI device used was a monodose inhaler. The NGI test conditions ranged between 20° C. and 25° C., and between 40% and 50% RH (relative humidity) (Table 19).

TABLE 19

|  | NGI 1 | NGI 2 | NGI 3 | NGI 4 | NGI 5 |
|---|---|---|---|---|---|
| Controlled condition | 21.83C/46.7% RH | 22.66C/47.3% RH | 21.93C/46.9% RH | 21.93C/46.9% RH | 21.99C/43.1% RH |
| Measured Flow | 99.1 SLPM | 98.4 SLPM | 97.6 SLPM | 100.0 SLPM | 100.5 SLPM |

Table 20 shows the aerodynamic properties of DSPC/acetylsalicylic acid particles.

TABLE 20

|  | 2 capsules | | 1 capsule | | |
|---|---|---|---|---|---|
|  | NGI 1 | NGI 2 | NGI 3 | NGI 4 | NGI 5 |
| Device, µg | 7876.4 | 9010.6 | 4267.0 | 4118.0 | 5115.8 |
| Capsule 1, µg | 653.6 | 717.9 | 484.6 | 464.5 | 670.5 |
| Capsule 2, µg | 616.2 | 560.3 | NA | NA | NA |
| Induction Port, µg | 11611.6 | 14550.8 | 7253.0 | 7454.4 | 6792.6 |
| Stage 1, µg | 10232.0 | 9393.6 | 3704.8 | 4257.6 | 5481.2 |
| Stage 2, µg | 17402.0 | 16198.0 | 8284.4 | 8136.4 | 8758.4 |
| Stage 3, µg | 10882.4 | 9993.6 | 5600.8 | 4976.4 | 5087.6 |
| Stage 4, µg | 4884.0 | 4864.4 | 2791.2 | 2387.2 | 2273.6 |
| Stage 5, µg | 1670.0 | 1514.8 | 983.2 | 757.6 | 891.2 |
| Stage 6, µg | 983.8 | 1076.6 | 619.8 | 471.9 | 530.3 |
| Stage 7, µg | 575.6 | 498.2 | 318.9 | 262.9 | 284.1 |
| MOC, µg | 320.8 | 292.4 | 134.0 | 158.0 | 201.7 |
| Nozzles, µg | 5364.8 | 6363.2 | 2546.4 | 2833.6 | 3280.8 |
| Nominal loaded mass (mg) | 74 | 74 | 37 | 37 | 37 |
| ED (mg) | 63.93 | 64.75 | 32.24 | 31.70 | 33.58 |
| Nominal % ED (mg) | 86% | 88% | 87% | 86% | 91% |
| FPD (mg) | 32.2 | 30.8 | 16.6 | 15.1 | 16.0 |
| FPF (%) | 50.4 | 47.5 | 51.5 | 47.7 | 47.5 |
| MMAD (µm) | 3.94 | 3.93 | 3.62 | 3.91 | 4.12 |
| GSD | 1.91 | 1.94 | 1.91 | 1.94 | 2.00 |
| Recovery (%) | 99.8 | 100.0 | 101.2 | 100.1 | 103.7 |

Example 5 NGI Analysis of Spray Dried Acetylsalicylic Acid/Soy Lecithin Particles The dry powders of Example 1 were evaluated for aerodynamic performance. The DPI device used was a monodose inhaler. The NGI test conditions ranged between 20° C. and 25° C., and between 40% and 50% RH (relative humidity)(Table 21).

TABLE 21

|  | NGI 1 | NGI 2 | NGI 3 | NGI 4 | NGI 5 |
|---|---|---|---|---|---|
| Controlled condition | 22.57 C./49.6% RH | 22.16 C./48.7% RH | 22.14 C./47.9% RH | 21.76 C./45.1% RH | 21.66 C./45.1% RH |
| Measured Flow | 98.7 SLPM | 97.6 SLPM | 99.0 SLPM | 100.0 SLPM | 97.5 SLPM |

Table 22 shows the aerodynamic properties of soy lecithin/acetylsalicylic acid particles.

TABLE 22

|  | 2 capsules | | 1 capsule | | |
|---|---|---|---|---|---|
|  | NGI 1 | NGI 2 | NGI 3 | NGI 4 | NGI 5 |
| Device, µg | 13139.2 | 15032.8 | 7664.0 | 6554.6 | 8382.0 |
| Capsule 1, µg | 1259.1 | 1607.1 | 1595.1 | 1078.2 | 916.0 |
| Capsule 2, µg | 2893.7 | 1050.2 | NA | NA | NA |
| Induction Port, µg | 5834.4 | 5586.6 | 3008.0 | 3604.4 | 3795.8 |
| Stage 1, µg | 4378.4 | 5104.0 | 1962.0 | 2274.8 | 2266.0 |
| Stage 2, µg | 12060.0 | 12890.8 | 5726.0 | 6028.0 | 6028.0 |
| Stage 3, µg | 15818.4 | 16041.6 | 7544.0 | 7687.2 | 7712.0 |
| Stage 4, µg | 11276.8 | 11301.6 | 5556.8 | 5345.6 | 5485.6 |
| Stage 5, µg | 3305.2 | 3182.0 | 1692.4 | 1622.4 | 1694.4 |
| Stage 6, µg | 1272.6 | 1161.2 | 749.5 | 728.2 | 658.7 |
| Stage 7, µg | 708.4 | 605.2 | 436.4 | 414.9 | 366.2 |
| MOC, µg | 340.8 | 375.8 | 231.8 | 228.6 | 236.9 |
| Nozzles, µg | 4105.6 | 4928.0 | 1812.8 | 2306.4 | 2121.6 |
| Nominal loaded mass (mg) | 74 | 74 | 37 | 37 | 37 |
| ED (mg) | 59.10 | 61.18 | 28.72 | 30.24 | 30.37 |
| Nominal % ED (mg) | 80% | 83% | 78% | 82% | 82% |
| FPD (mg) | 42.7 | 43.7 | 20.9 | 21.2 | 21.2 |
| FPF (%) | 72.3 | 71.5 | 72.7 | 70.0 | 69.7 |
| MMAD (µm) | 2.71 | 2.79 | 2.65 | 2.72 | 2.72 |
| GSD | 1.72 | 1.73 | 1.75 | 1.75 | 1.75 |
| Recovery (%) | 104.6 | 104.0 | 104.4 | 103.1 | 104.5 |

HPLC analysis of acetylsalicylic acid in NGI and Delivered Dose samples was carried out as follows.

Equipment

The HPLC column was Phenomenex Luna C18(2) 5 µm, 4.6×100 mm. Shimadzu HPLC Equipment was used, including Shimadzu SIL-HTC Autosampler, Shimadzu CTO-10ASVP Column Oven. Shimadzu LC-10ADVP Binary HPLC Pump, Shimadzu DGU-14A Inline Degasser, Shimadzu UV Detector, and Computer with Shimadzu Class VP software.

Materials

Mobile Phase A was 69:28:3 Water:Methanol:Glacial Acetic Acid. Mobile Phase B was 97:3 Methanol:Glacial Acetic Acid. Diluent was 95:5 Methanol:Glacial Acetic Acid. Needlewash was 50:50 Water:Methanol. The working standard was 750 µg/mL acetylsalicylic acid (working standard A "WSA" and working standard B "WSB").

HPLC Conditions and Analysis

Flow rate was 2.0 mL/min. The sample injection volume was 10 µL. The gradient was run according to the timing scheme in Table 23.

TABLE 23

| HPLC Gradient Program | |
|---|---|
| Time (min) | % B |
| 0.00 | 0.0 |
| 3.80 | 0.0 |
| 3.81 | 100.0 |
| 5.80 | 100.0 |
| 5.81 | 0.0 |
| 8.00 | STOP |

The analysis of the samples was in the following sequence:

| | | |
|---|---|---|
| A. | Blank | (2 injections) |
| B. | Working Standard A | (6 injections) |
| C. | Working Standard B | (2 injections) |
| D. | Blank | (1 injection) |
| E. | Sample | (1 injection each) |
| F. | WSB (QC Standard) | (1 injection) |

Repeat steps E-F as necessary ensuring that the last injection of a sequence is a QC standard.

The standard agreement between WSA and WSB must be within 97.0-103.0%. The QC standard agreement between the ongoing standard analysis and initial analysis (n=2) for WSB must between 97.0-103.0%.

The standard agreement between WSA and WSB was calculated according to the equation below.

$$SA = \frac{A_{WSA}}{A_{WSB}} \times \frac{C_{WSB}}{C_{WSA}} \times 100$$

Where:
SA=Standard Agreement (%)
$A_{WSA}$=WSA Average Area (n=6)
$A_{WSB}$=WSB Average Area (n=2)
$C_{WSA}$=WSA Theoretical Concentration (µg/mL)
$C_{WSB}$=WSB Theoretical Concentration (µg/mL)
100=Conversion to %

The % recovery of the QC standard(s) was calculated according to the equation below.

$$QC = \frac{A_{QC}}{A_{WSB}} \times 100$$

Where:
QC=QC % Recovery
$A_{QC}$=QC Area
$A_{WSB}$=Initial WSB Average Area (n=2)
100=Conversion to %

The concentration of samples was calculated according to the equation below.

$$C_{SX} = \frac{A_{SX}}{A_{WSA}} \times C_{WSA}$$

Where:
$C_{SX}$=Sample Concentration (µg/mL)
$A_{SX}$=Sample Area
$A_{WSA}$=WSA Average Area (n=6) Area
$C_{WSA}$=Theoretical WSA Concentration (µg/mL)

Example 6 Spray Pattern and Plume Geometry

Spray pattern and plume geometry characterization of spray pattern and plume geometry of the formulation will be evaluated using standard methodology (see, http://www.proveris.com/products/sprayview/; see also, http://www.oxfordlasers.com/imaging/spray-pattern-plume-geometry-measurement).

Various factors can affect the spray pattern and plume geometry, including the size and shape of the actuator orifice, the design of the actuator, the size of the metering chamber, the size of the stem orifice of the valve, the vapor pressure in the container, and the nature of the formulation. Spray pattern testing will be tested on all formulations under a variety of different temperature and humidity conditions.

Example 7—Dry Powder Stability Testing

The following test parameters will be analyzed for the dry powder formulations.

i. Appearance and Color

The appearance of the content of the container and the appearance of the container and closure system (i.e., the valve and its components and the inside of the container) will be analyzed. To determine whether there is any color is associated with the formulation (either present initially or from degradative processes occurring during shelf life.

ii. Microbial Limits

The microbial quality will be controlled for the total aerobic count, total yeast and mold count, and freedom from designated indicator pathogens. Appropriate testing will be done to show that the drug product does not support the growth of microorganisms and that microbial quality is maintained throughout the expiration period.

iii. Water or Moisture Content

Water or moisture content will be analyzed. Changes in particle size distribution, morphic form, and other changes such as crystal growth or aggregation will be evaluated.

iv. Dose Content Uniformity

Dose content uniformity will be evaluated across multiple batches, formulations and under stability testing condition. The amount of active ingredient per determination will be evaluated to show that the emitted dose is 80-120 percent of label claim for more than one of ten containers. The dose content uniformity over container life will also be evaluated.

v. Particle Size Distribution

Particle size distribution will be evaluated across all batches, formulations as well as under stability testing conditions. For particular formulations, the total mass of drug collected on all stages and accessories will be shown to lie between 85 and 115 percent of label claim on a per actuation basis.

vi. Stability studies will be performed on all batches as well as each formulation. The test storage conditions in the stability protocol for a drug product intended for storage under controlled room temperature conditions will include (1) accelerated (40±2° C./75±5% Relative Humidity (RH)), (2) intermediate (30±2° C./60±5% RH), if applicable, and (3) long-term (25±2° C./60±5% RH) conditions.

Examples 8-12

Particle Size Analysis

Particle size analysis was carried out using laser diffraction and light microscopy.

A Malvern Mastersizer 2000 equipped with a Scirocco 2000 Sample Dispersion Unit was used to measure the geometric particle size of the samples. For each measurement approximately 50-100 mg of powder was loaded into the micro volume tray. Measurement parameters can be found in Table 24. 3 replicates are run per sample and the average of the three replicates is reported to 3 decimal places.

TABLE 24

| | |
|---|---|
| Sampler | Scirocco, original configuration |
| Sample Tray | Micro Volume |
| Material Name | Fraunhofer (RI = 0) |
| Calculation Model | General Purpose - normal sensitivity |

TABLE 24-continued

| | |
|---|---|
| Background Measurement Time | 10 seconds |
| Sample Measurement Time | 30 seconds |
| Obscuration Limits | 1-6% |
| Obscuration Filtering | Enable filtering, 30 second time out |
| Feed Rate | 75% |
| Dispersive Air Pressure | 4.0 Bar |

Morphology

Scanning Electron Microscopy

Field emission scanning electron microscopy (FE-SEM, FEI, Sirion, USA) was used to examine the morphology and surface appearance of various ASA particles. The samples were attached to specimen stubs with two-sided adhesive tape and Pt-coated with a sputter coater (BAL-TEC, SCD 005, Germany) at 30 mA for 150 s. The coated microcapsules were examined using a Sirion SEM at 10 kV with a 1.5 nm resolution according to a previously reported method (Rosenberg et al., 1985).

HPLC Analysis:

Equipment

The HPLC column was Phenomenex Luna 3u C18(2) 50 mm, 4.6 µm, which caused the drug to elute at ~1.3 minutes.

| HPLC Method Conditions | |
|---|---|
| Analytical Column | Phenomenex Luna 3µ C18, 4.0 × 300 mm, 5 µm |
| Mobile Phase A | 10 mM Sodium Heptanesulfonte in 85:15 Water:Acetonitrile (pH 3.4 with Acetic Acid) |
| Mobile Phase B | NA |
| Diluent | 1% Formic Acid in Acetonitrile |
| Flow Rate | 2.0 mL/min |
| Column Temperature | 40° C. |
| Injection Volume | 10 µL |
| UV Wavelength | 280 nm |
| Run Time | 5.0 min (Isocratic) |

The particle size measurement is taken by quantifying deposition amounts by HPLC and entering these values into a program CITDAS—Copley Inhaler Testing Data Analysis Software.

Batches of aspirin formulation, manufactured using either a jet milled or solution based approach were evaluated for the general characteristics, as well as for the stability studies (see Example 8). For some of the aspirin (ASA) formulations of the present invention. ASA was jet milled to <5 µm and suspended at 2 wt % in hexane, followed by spray drying. Additionally, the impact of including lecithin into the formulation was also tested. Thus, properties of jet milled ASA, which was suspended at 2 wt % in hexane, and then spray dried in the presence or absence of lecithin were evaluated in Example 8.

General manufacturing and yield characteristics of jet-milled control (BREC1511-024, 100% jet-milled ASA), spray dried from hexane, 100% ASA (BREC1511-038A), and spray dried from hexane 99.9/0.1 ASA/Lecithin (BREC1511-038B) are depicted in Table 25 (Example 8).

Next, the accelerated stability study of the formulations was carried out. Bulk stability, particle size stability, and aerosol stability of ASA formulations are described in Example 8.

Bulk powder aliquots were prepared under dry conditions and placed in amber glass jar, after which they were sealed with desiccant in Mylar bags. The bulk stability study incorporated a 4-week analysis of samples at 30° C. and 65% relative humidity (RH).

The following formulations were prepared according to the protocol described in Example 8: 100% jet-milled ASA (BREC1511-024), BREC1511-038A (spray dried from hexane containing 100% ASA), and spray dried from hexane containing 99.9/0.1 ASA/Lecithin (BREC1511-038B).

RP-HPLC assay showed that there was no significant loss of potency or increase in degredents over the period of 4 weeks (Table 26). Also, under the 65% relative humidity conditions, none of the formulations contained any measureable water, nor was there any uptake detected.

Particle size stability over the period of 4 weeks for formulations generated from milling (FIG. 8) was evaluated. Particle size analysis at each step (0 week, 1 week, 2 weeks, and 4 weeks) was carried out using Malvern particle size analyzer.

Of the formulations tested, spray dried milled ASA from 100% hexane (BREC-1511-038A) and spray dried milled ASA suspended in hexane with lecithin (BREC-1511-038B) exhibited particle size stability over 4 weeks of analysis (FIG. 8).

The profile of particles obtained at time 0 (30° C. and 65% relative humidity (RH)) for spray dried milled ASA suspended in 100% hexane (BREC-1511-038A) was the following: D(v0.1)=0.9 µm; D(v0.5)=2.3 µm; D(v0.9)=4.5 µm; D[3, 2]=1.6 µm; and D[4, 3]=2.5 µm (FIG. 8). The profile of particles obtained at 4 weeks (30° C. and 65% relative humidity (RH)) for spray dried milled ASA suspended in 100% hexane (BREC-1511-038A) was the following: D(v0.1)=0.9 µm; D(v0.5)=2.3 µm; D(v0.9)=4.6 µm; D[3, 2]=1.7 µm; and D[4, 3]=2.6 µm (FIG. 8).

The profile of particles obtained at time 0 (30° C. and 65% relative humidity (RH)) for spray dried milled ASA suspended in hexane with lecithin (BREC-1511-038B) was the following: D(v0.1)=0.9 µm; D(v0.5)=2.0 µm; D(v0.9)=3.9 µm; D[3, 2]=1.6 µm; and D[4, 3]=2.2 µm (FIG. 8). The profile of particles obtained at 4 weeks (30° C. and 65% relative humidity (RH)) for spray dried milled ASA suspended in hexane with lecithin (BREC-1511-038B) was the following: D(v0.1)=1.0 µm; D(v0.5)=2.4 µm; D(v0.9)=4.6 µm; D[3.2]=1.7 µm; and D[4, 3]=2.6 µm (FIG. 8).

Taken together, particle size stability studies provide that spray dried milled ASA suspended in 100% hexane, as well as spray dried milled ASA suspended in hexane with lecithin, displays stability over the prolonged period (about at 30° C. and 65% relative humidity (RH), where the particle size distribution changed less than 10% over time.

Following the particle size stability analysis, aerosol performance assay was carried out using a low resistance dry powder inhaler device. The aerodynamic particle size distributions of BREC1511-024, BREC1511-038A, and BREC1511-038B emitted from the dry powder inhaler (DPI) were measured with an eight stage next generation pharmaceutical impactor (NGI). The NGI is a particle-classifying cascade impactor for testing metered-dose, dry-powder, and similar inhaler devices. One unique feature of NGI is a micro-orifice collector (MOC) that captures in a collection cup extremely small particles normally collected on the final filter in other impactors. The particles captured in the MOC cup can be analyzed in the same manner as the particles collected in the other impactor stage cups (Marple et al. *Journal of Aerosol Medicine*, v. 16, (2003).

Particle size distributions at week 0 and week 4 were compared determining mass median aerodynamic diameter (MMAD), geometric standard deviation (GSD), emitted fraction (EF), fine particle fraction (FPF)<5 micrometers, and fine particle dose (FPD). Table 27 provides a summary of findings of aerodynamic properties for each formulation, whereas FIG. 9 (BREC1511-024), FIG. 10 (BREC1511-038A), and FIG. 11 (BREC1511-038B), show detailed particle size distribution at week 0 and week 4 based on NGI analysis.

Aerosol performance studies revealed that spray dried milled ASA suspended in 100% hexane (BREC1511-038A) (FIG. 10), and spray dried milled ASA suspended in hexane with lecithin (BREC1511-038B) (FIG. 11) maintained the same aerosol properties during the 4 weeks, or did not exhibit a significant aerosol property shift during the 4 weeks. On the contrary, BREC1511-024, displayed a large shift in properties, with dramatic increase in MMAD and decrease in FPF (FIG. 9).

In conclusion, the results obtained in these studies demonstrate that (1) general potency and purity of bulk powder is unchanged after 4 weeks at 30° C. and 65% RH; (2) spray dried milled ASA suspended in 100% hexane (BREC1511-038A) and spray dried milled ASA suspended in hexane with lecithin (BREC1511-038B) showed stability over the period of 4 weeks; and (3) spray dried milled ASA suspended in 100% hexane (BREC1511-038A) and spray dried milled ASA suspended in hexane with lecithin (BREC1511-038B) do not exhibit any change (or exhibit slight changes) in the aerosol performance after 4 weeks. On the contrary, jet milled products changed dramatically after 4 week's condition.

Figure 10:
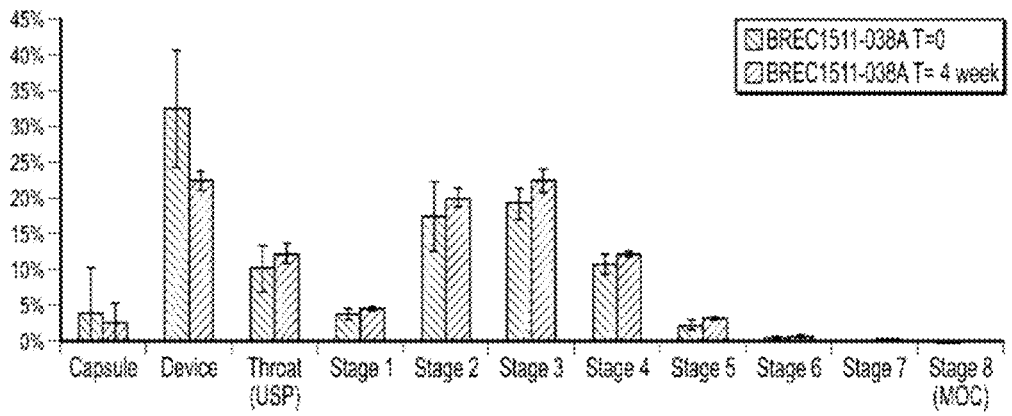
FIG. 10 shows the particle size distribution of BREC1511-038A particles based on NGI analysis (week 4, at 30° C. and 65% RH).

As shown in FIG. 10, BREC1511-038A displayed the following characteristics at 0 time point: MMAD: 3.92±0.13 μm; geometric standard deviation (GSD): 1.67±0.02; emitted fraction (EF): 63.6±12.7%; fine particle fraction (FPF)<5 μm: 58.8±3.3%; and fine particle dose (FPD): 11.6±1.1 mg. After 4 weeks at 30° C. and 65% RH, BREC1511-038A had the following characteristics: MMAD: 3.90±0.08 pan; GSD: 1.64±0.02: EF: 75.1±3.2%: FPF: 58.2±2.2%; and FPD: 12.1±0.8 mg.

Figure 11:
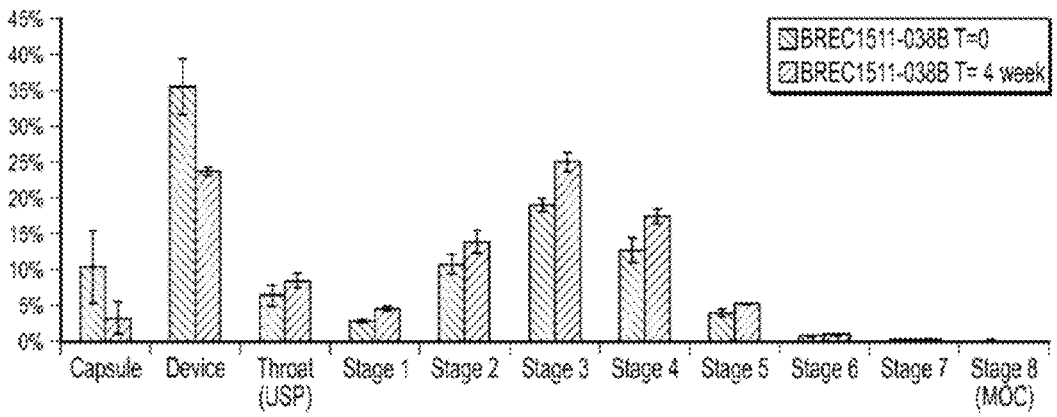
FIG. 11 shows the particle size distribution of BREC1511-038B particles based on NGI analysis (week 4, at 30° C. and 65% RH).

As shown in FIG. 11, BREC1511-038B displayed the following characteristics at 0 time point: MMAD: 3.36±0.09 μm; geometric standard deviation (GSD): 1.67±0.02; emitted fraction (EF): 55.2±3.2%; fine particle fraction (FPF)<5 μm: 70.1±3.0%; and fine particle dose (FPD): 12.9±1.5 mg. After 4 weeks at 30° C. and 65% RH, BREC1511-038B had the following characteristics: MMAD: 3.36±0.09±m; GSD: 1.73±0.03; EF: 73.8±2.3%; FPF: 69.4±2.3%; and FPD: 16.9±1.5 mg.

In certain embodiments, the dry particles of the present composition have an MMAD which varies less than about 10%, less than about 6%, or less than about 1%, after the composition is stored at 30° C. at 65% relative humidity for about 4 weeks.

Next, particle size distribution analysis was performed to characterize the formulation before and after the 2-week storage period at 50° C./75% RH. Average D(0.1), D(0.5) and D(0.9), D(3, 2), and D(4,3) values for BREC1511-024, BREC1511-038A, and BREC1511-038B are shown in Table 11.

Figure 14:
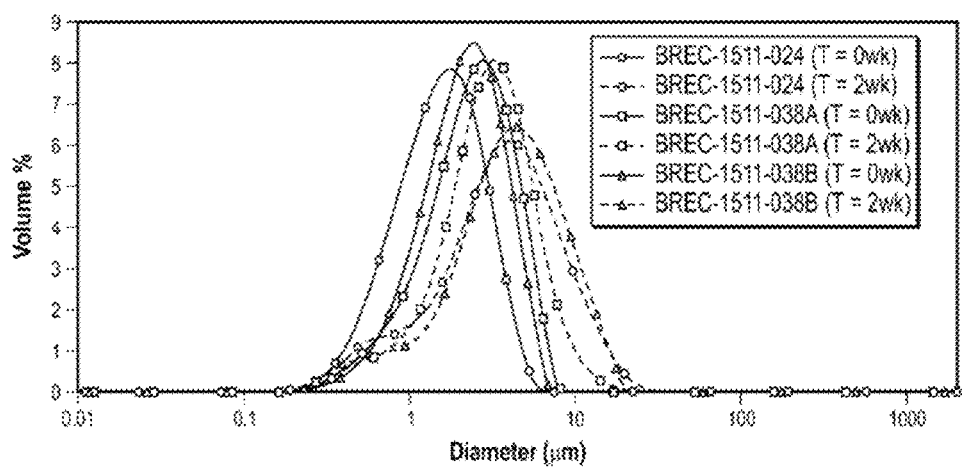
FIG. 14 is a graph of particle size distribution of BREC1511-024, BREC1511-038A, and BREC1511-038B after 2 weeks at 50° C./75% RH.

As illustrated in Table 11 and FIG. 14, all 3 formulations showed an increase in particle size after the 2-week storage period at 50° C./75% RH. However, BREC-1511-038A exhibited the least variation between week 0 and week 2, while BREC-1511-024 and BREC-1511-038B exhibited similar levels of variation in particle size distribution before and after the 2-week storage period. While the particle size of milled ASA spray dried with lecithin was slightly smaller compared to ASA alone, the change in particle size from week 0 to week 2 was greater for BREC-1511-038B then BREC-1511-038A.

The aerodynamic particle size distributions of BREC1511-024, BREC1511-038A, and BREC1511-038B at week 0 and week 2 after storage at 50° C./75% RH were compared determining mass median aerodynamic diameter (MMAD), geometric standard deviation (GSD), emitted fraction (EF), and fine particle fraction (FPF)<5 micron. FIGS. 21-23 illustrate deposition profile of each aspirin formulation before and after the 2-week period in the next-generation impactor following aerosolization, where y axis=deposited fraction (% recovered dose)).

Figure 17:
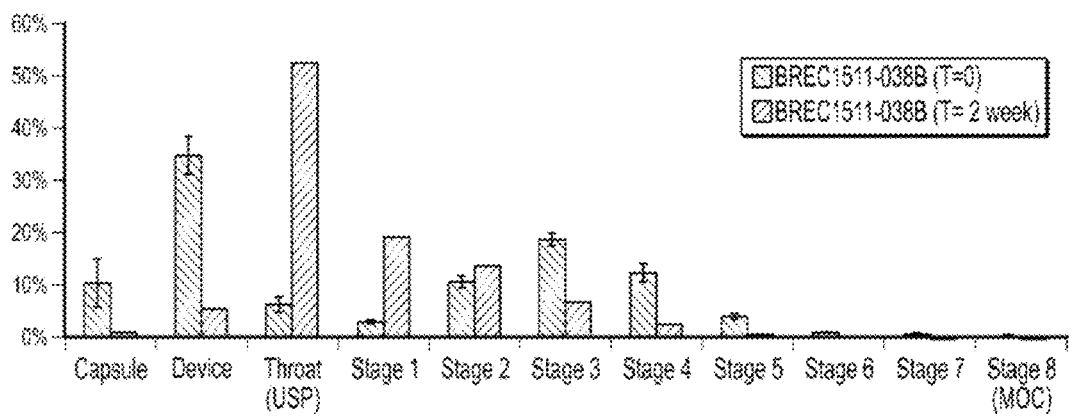
FIG. 17 shows the particle size distribution of BREC1511-038B particles based on NGI analysis (after 2 weeks at 50° C./75% RH).

While BREC1511-024 (FIG. 15) and BREC-1511-038B (FIG. 17) displayed shifts in aerosol properties after 2 weeks, BREC1511-038A showed the smallest change of the 3 formulations (FIG. 16).

Thus, under various temperature, time, and humidity conditions, milled ASA suspended in hexane and spray dried, as well as milled ASA suspended in hexane and spray dried with lecithin, exhibits stability.

In one embodiment. ASA is suspended in hexane prior to spray drying. In another embodiment, ASA is suspended in heptane prior to spray drying. In a further embodiment, ASA is suspended in heptane or hexane isomer. In yet another embodiment, ASA is suspended in heptane or hexane derivative prior to spray drying.

Example 8

Batches of aspirin formulations were manufactured and generally characterized, manufactured using either a jet milled or solution based (wet polishing) approach.

Aspirin (ASA) was jet milled to <5 μm and suspended at 2 wt % in a particular solvent. Briefly, ASA solutions were prepared by adding aspirin to the appropriate solvent followed by stirring until a homogeneous solution was obtained. A BUCHI spray dryer model B-290 Advanced was used in all experiments. High performance cyclones were used to collect the dried product. The spray-drying unit was operated in open cycle, with the aspirator blowing nitrogen at 100% of capacity, corresponding to a flow rate of the dry nitrogen of approximately 40 kg per hour. Before feeding the stock solution, the spray dryer was stabilized with the particular solvent. During the stabilization period, the solvent flow rate was adjusted in order to give the target outlet temperature. After stabilization of the outlet temperature, the feed of the spray dryer was commuted from the solvent to the product solution (inlet temperature was then readjusted to maintain the outlet temperature in the target value). At the end of the stock solution, the feed was once more commuted to solvent, in order to rinse the feed line and carry out a controlled shutdown.

In this specific Example, jet milled ASA was suspended at 2 wt % in hexane, and then spray dried in the presence or absence of lecithin. The properties of the ASA formulation were evaluated.

In some cases, an excipient is provided to dry powder formulation in order to coat the active pharmaceutical ingredient, thus "masking" it. Masking can be useful when the unmodified active pharmaceutical is irritating or otherwise unpleasant to the recipient.

Examples of suitable phospholipid excipients include, without limitation, phosphatidylcholines, phosphatidylethanolamines, phosphatidylinositol, phosphatidylserines, sphingomyelin or other ceramides, as well as phospholipid containing oils such as lecithin oils. As mentioned above, in this example the inventors tested the effects of lecithin addition to hexane ASA suspension.

General manufacturing and yield characteristics of jet-milled control (BREC1511-024 (100% jet-milled ASA), spray dried from hexane 100% ASA (BREC1511-038A), and spray dried from hexane 99.9/0.1 ASA/Lecithin (BREC1511-038B) are depicted in Table 25.

TABLE 25

General characteristics of BREC1511-024, BREC1511-038A, and BREC1511-038B

| Spray Reference (BREC-1511) | -024 | -038A | -038B |
|---|---|---|---|
| Purpose | Jet-Milled Control | Neat ASA; spray dry jet milled ASA | spray dry jet milled ASA |
| Dry Solids Formulation | 100% ASA | | 99.9/0.1 ASA/Lecithin |
| Spray Dryer Scale | NA | BLD-35 | |
| Batch Size (g) | 150 | 6.8 | |
| Spray Solution | NA | 2 Wt % Jet-Milled ASA | 2 Wt % Jet-Milled ASA in Hexane + Lecithin |
| Nozzle | | 2-Fluid | |
| Solution Feed Rate | | 12 | |
| Atomization Pressure | | 60 | |
| Inlet Temp. (° C.) | | 115 | |
| Outlet Temp. (° C.) | | 60 | |
| Yield (%) | 81 | 68 | 65 |
| $D_{10}$, $D_{50}$, $D_{90}$ | 0.7, 1.7, 3.4 | 0.9, 2.3, 4.5 | 0.9, 2.0, 3.9 |

As seen in Table 25, particle size distribution analysis showed that D10 was higher for spray dried formulations than for the initial jet milled product. Furthermore, D50 and D90 were higher for BREC1511-038A (100% ASA in hexane, without lecithin) compared to BREC1511-038B (spray dried from hexane 99.9/0.1 ASA/Lecithin).

Figure 7A:
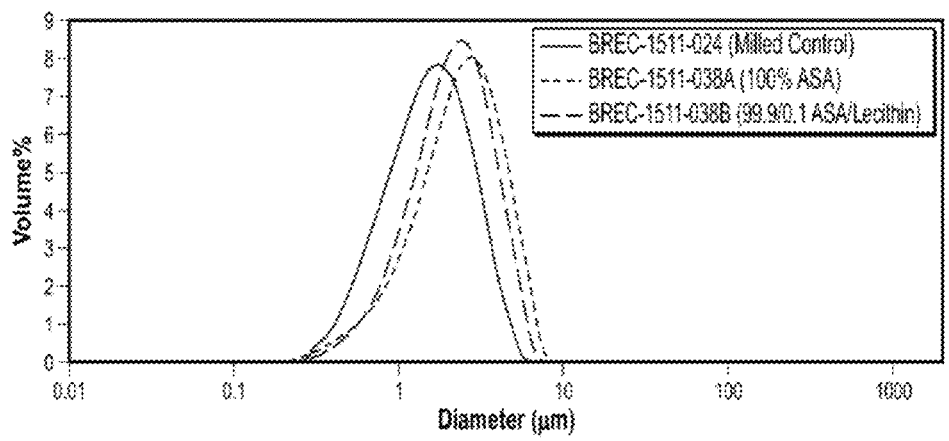
FIGS. 7A and 7B show laser diffraction data (FIG. 7A) and morphology (FIG. 7B) of milled control (BREC-1511-024, 100% jet-milled ASA), 100% ASA (BREC-1511-038A, spray dried from hexane), and 99.9/0.1 ASA/Lecithin (BREC-1511-038B, spray dried from hexane) formulations.
Figure 7B:
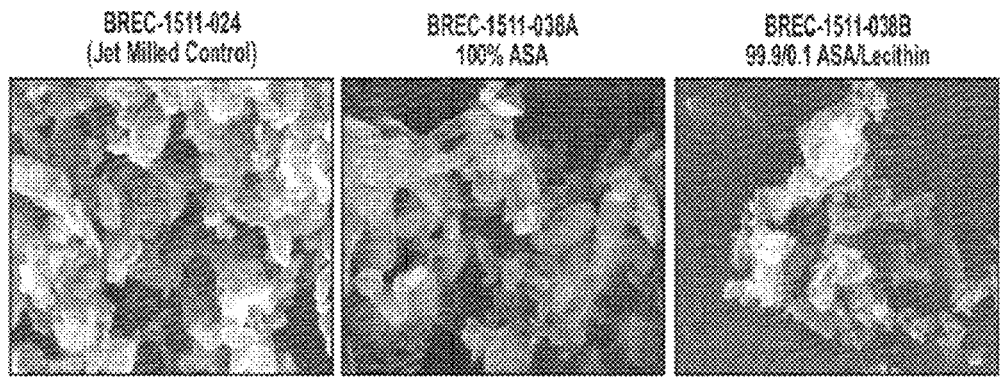

Next, the particle size and particle morphology were evaluated in further detail. Particle size distribution analysis was performed using Malvern Particle size analyzer (FIG. 7A). As shown in FIG. 7A, the collected spray dried particle size was larger than the initial milled product. Without being bound to a particular theory, it is expected that this is likely related to slight agglomeration or fusion of particles during the spray drying process. Furthermore, it is known that cyclone efficiency decreases with smaller particle size, which can result in slight bias of collected particles.

Crystal morphology plays an important role in drug processing and delivery. Here, particle morphology of jet milled control BREC1511-024, 100% ASA BREC1511-038A, and 99.9/0.1 ASA/Lecithin BREC1511-038B was determined by scanning electron microscopy (FIG. 1B). Briefly, field emission scanning electron microscopy (FE-SEM, FEI, Sirion, USA) was used to examine the morphology and surface appearance of various ASA particles. The samples were attached to specimen stubs with two-sided adhesive tape and Pt-coated with a sputter coater (BAL-TEC, SCD 005, Germany) at 30 mA for 150 s. The coated microcapsules were examined using a Sirion SEM at 10 kV with a 1.5 nm resolution according to a previously reported method (Rosenberg et al., 1985).

Thus, this Example shows that in ASA formulations where hexane is used as a solvent, milled ASA spray dried with lecithin leads to slightly smaller particle size as compared to 100% ASA in hexane.

Example 9 Accelerated Stability Study

In the next series of studies (Examples 9 and 10), the bulk stability, particle size stability, and aerosol stability of ASA formulations described in Example 8 were evaluated.

Bulk Stability

Bulk powder aliquots were prepared under dry conditions and placed in amber glass jar, after which they were sealed with desiccant in Mylar bags. The bulk stability study was designed to incorporate a 4-week analysis of samples at 30° C. and 65% relative humidity (RH).

The following formulations were prepared according to the protocol described in Example 8: 100% jet-milled ASA (BREC1511-024). BREC1511-038A (spray dried from hexane 100% ASA), and spray dried from hexane 99.9/0.1 ASA/Lecithin (BREC1511-038B).

RP-HPLC assay showed that there was no significant loss of potency or increase in degredents over the period of 4 weeks (Table 26). Also, under the 65% relative humidity conditions, none of the formulations contained any measureable water, nor was there any uptake detected.

Next, the inventors evaluated particle size stability over the period of 4 weeks for formulations generated from milling (FIG. 8). Particle size analysis at each step (0 wk, 1 wk, 2 wk, and 4 wk) was carried out using Malvern particle size analyzer.

The profile of particles obtained at time 0 (30° C. and 65% relative humidity (RH)) for spray dried milled ASA suspended in 100% hexane (BREC-1511-038A) was the following: D(v0.1)=0.9 µm; D(v0.5)=2.3 µm; D(v0.9)=4.5 µm; D[3, 2]=1.6 µm; and D[4, 3]=2.5 µm (FIG. 8). The profile of particles obtained at 4 weeks (30° C. and 65% relative humidity (RH)) for spray dried milled ASA suspended in 100% hexane (BREC-1511-038A) was the following: D(v0.1)=0.9 µm; D(v0.5)=2.3 µm; D(v0.9)=4.6 µm; D[3, 2]=1.7 µm; and D[4, 3]=2.6 µm (FIG. 8).

The profile of particles obtained at time 0 (30° C. and 65% relative humidity (RH)) for spray dried milled ASA suspended in hexane with lecithin (BREC-1511-038B) was the following: D(v0.1)=0.9 µm; D(v0.5)=2.0 µm; D(v0.9)=3.9 µm; D[3, 2]=1.6 µm; and D[4, 3]=2.2 µm (FIG. 8). The profile of particles obtained at 4 weeks (30° C. and 65% relative humidity (RH)) for spray dried milled ASA suspended in hexane with lecithin (BREC-1511-038B) was the following: D(v0.1)=1.0 µm; D(v0.5)=2.4 µm; D(v0.9)=4.6 µm; D[3.2]=1.7 µm; and D[4, 3]=2.6 µm (FIG. 8).

Taken together, particle size stability studies provide that spray dried milled ASA suspended in 100% hexane, as well as spray dried milled ASA suspended in hexane with lecithin, displays stability over the prolonged period (about at 30° C. and 65% relative humidity (RH), where the particle size distribution changed less than 10% over time.

TABLE 26

RP-HPLC Assay

| Lot | Approach | Formulation (w/w %) | Initial Assay | 1 Week Assay (ASA) | 2 Week Assay (ASA) | 4 Week Assay (ASA) |
|---|---|---|---|---|---|---|
| BREC-1511-024 | Jet milled | 100% ASA | — | 99.9% ± 0.5 | 102.9% ± 4.0 | 99.5% ± 0.3 |
| BREC-1511-038A | Suspended Milled | 100% ASA | 101.3% ± 0.9 | 101.0% ± 0.9 | 100.5% ± 0.0 | 99.6% ± 0.1 |
| BREC-1511-038B | ASA in Hexane | 99.9/0.1 ASA/Lecithin | 101.1% ± 0.4 | 100.0% ± 0.4 | 99.1% ± 0.4 | 100.6% ± 0.2 |

Aerosol Performance

Following the particle size stability analysis, aerosol performance assay was carried out. Briefly, aerosol performance was determined in vitro using a low resistance dry powder inhaler device. The aerodynamic particle size distributions of BREC1511-024, BREC1511-038A, and BREC1511-038B, emitted from the dry powder inhaler (DPI) were measured with an eight stage next generation pharmaceutical impactor (NGI). The NGI is a particle-classifying cascade impactor for testing metered-dose, dry-powder, and similar inhaler devices. One unique feature of NGI is a micro-orifice collector (MOC) that captures in a collection cup extremely small particles normally collected on the final filter in other impactors. The particles captured in the MOC cup can be analyzed in the same manner as the particles collected in the other impactor stage cups (Marple et al. *Journal of Aerosol Medicine*, v. 16, (2003).

For each compound formulation, a single size 3 HPMC capsule was filled with 37 mg of formulated aspirin, and loaded into a RS01 low resistance device. Material was actuated at 60 L/min for 4 seconds. Three replicates were performed per lot. Particle size distributions at week 0 and week 4 were compared determining mass median aerodynamic diameter (MMAD), geometric standard deviation (GSD), emitted fraction (EF), fine particle fraction (FPF)<5 micron, and fine particle dose (FPD). Table 27 provides a summary of findings of aerodynamic properties for each formulation, whereas FIG. 9 (BREC1511-024), FIG. 10 (BREC1511-038A), FIG. 11 (BREC1511-038B), show detailed particle size distribution at week 0 and week 4 based on NGI analysis.

Aerosol performance studies revealed that the only formulation that maintained the same aerosol properties during the 4 weeks was spray dried milled ASA suspended in 100% hexane (BREC1511-038A), (FIG. 10). On the contrary, BREC1511-024 displayed a large shift in properties, with dramatic increase in MMAD and decrease in FPF (FIG. 9). While BREC1511-038B did not exhibit a significant aerosol shift as the one observed for BREC1511-024, a small shift was nevertheless detected (FIG. 11). It is possible that the small shift is due to inherent variability, but this remains to be tested. Furthermore, an improved EF was identified, which resulted in higher FPD.

TABLE 27

Particle Size Stability at 4 weeks

| Lot Number | Formulation | Time Point | MMAD | GSD | Emitted Fraction (EF) (%) | Fine Particle Fraction (FPF) <5 um (%) | Fine Particle Dose (FPD) (mgA) |
|---|---|---|---|---|---|---|---|
| BREC1511-024 | Jet Milled ASA (Control) | Initial | 3.66 ± 0.23 | 1.77 ± 0.06 | 74.1 ± 18.3 | 60.9 ± 6.3 | 16.5 ± 12.9 |
| | | 4 week | 6.00 ± 0.10 | 1.87 ± 0.01 | 87.4 ± 1.2 | 22.1 ± 1.4 | 7.2 ± 0.4 |
| BREC1511-038A | 100% ASA (Hexane) | Initial | 3.92 ± 0.13 | 1.63 ± 0.07 | 63.6 ± 12.7 | 58.8 ± 3.3 | 13.7 ± 2.1 |
| | | 4 week | 3.90 ± 0.08 | 1.64 ± 0.02 | 75.1 ± 3.2 | 58.2 ± 2.2 | 16.2 ± 0.8 |
| BREC1511-038B | 99.9/0.1 ASA/lecithin (Hexane) | Initial | 3.36 ± 0.09 | 1.67 ± 0.02 | 55.2 ± 3.2 | 70.1 ± 3.0 | 14.3 ± 1.1 |
| | | 4 week | 3.36 ± 0.09 | 1.73 ± 0.03 | 73.8 ± 2.3 | 69.4 ± 2.3 | 19.0 ± 0.8 |

In conclusion, the results obtained in these studies demonstrate that (1) general potency and purity of bulk powder is unchanged after 4 weeks at 30° C. and 65% RH; (2) spray dried milled ASA suspended in 100% hexane (BREC1511-038A) and spray dried milled ASA suspended in hexane with lecithin (BREC1511-038B) showed stability over the period of 4 weeks; and (3) spray dried milled ASA suspended in 100% hexane (BREC1511-038A) and spray dried milled ASA suspended in hexane with lecithin (BREC1511-038B) do not exhibit any change (or exhibit slight changes) in the aerosol performance after 4 weeks. On the contrary, jet milled products changed dramatically after 4 week's condition.

As shown in FIG. 10, BREC1511-038A displayed the following characteristics at 0 time point: MMAD: 3.92±0.13 μm; geometric standard deviation (GSD): 1.67±0.02; emitted fraction (EF): 63.6±12.7%; fine particle fraction (FPF)<5 μm: 58.8±3.3%; and fine particle dose (FPD): 11.6±1.1 mg. After 4 weeks at 30° C. and 65% RH, BREC1511-038A had the following characteristics: MMAD: 3.90±0.08 μm; GSD: 1.64±0.02; EF: 75.1±3.2%; FPF: 58.2±2.2%; and FPD: 12.1±0.8 mg.

As shown in FIG. 11, BREC1511-038B displayed the following characteristics at 0 time point: MMAD: 3.36±0.09 μm; geometric standard deviation (GSD): 1.67±0.02; emitted fraction (EF): 55.2±3.2%; fie particle fraction (FPF)<5 μm: 70.1±3.0%; and fine particle dose (FPD): 12.9±1.5 mg.

After 4 weeks at 30° C. and 65% RH, BREC1511-038B had the following characteristics: MMAD: 3.36±0.09 µm; GSD: 1.73±0.03: EF: 73.8±2.3%; FPF: 69.4±2.3%; and FPD: 16.9±1.5 mg.

In certain embodiments, the dry particles of the present composition have an MMAD which varies less than about 10%, less than about 6%, or less than about 1%, after the composition is stored at 30° C. at 65% relative humidity for about 4 weeks.

Example 10 Accelerated Stability Study (2 Weeks at 50° C.75% RH)

In this study, 3 different formulations of spray dried aspirin were evaluated: BREC1511-024 (100% jet-milled ASA), BREC1511-038A (spray dried from hexane 100% ASA), and BREC1511-038B (spray dried from hexane 99.9/0.1 ASA/Lecithin).

Briefly, bulk powder aliquots were prepared under dry conditions and placed in amber glass jar, after which they were sealed with desiccant in Mylar bags. Each sample was then incubated for 2 weeks at 50° C. and 75% relative humidity (RH) conditions. Subsequent to the 2-week incubation period, the following properties of each formulation were examined: 1) particle morphology; 2) water content: 3) potency/purity of the formulation; 4) particle size distribution; and 5) NGI analysis (single replicate).

Particle Morphology

Figures 12A, 12B, 12C:
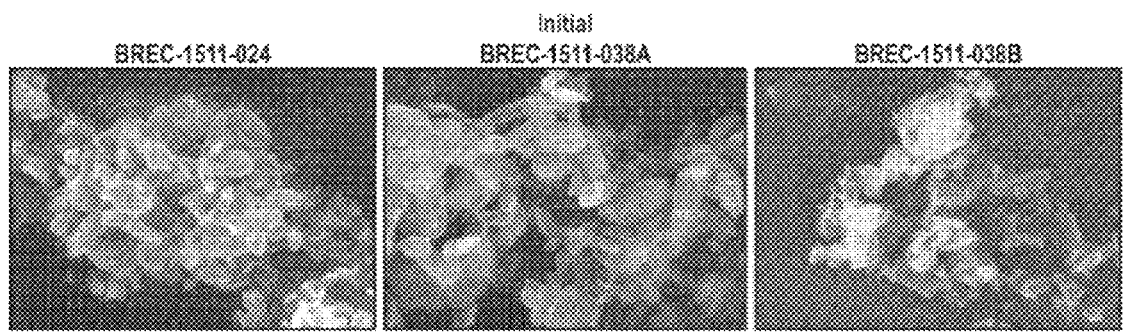
FIGS. 12A-12F show particle morphology of BREC1511-024, BREC1511-038.4, and BREC1511-038B (99.9/0.1 ASA/Lecithin) formulations (at initial time point and 2 weeks, at 50° C./75% RH).
Figures 12D, 12E, 12F:
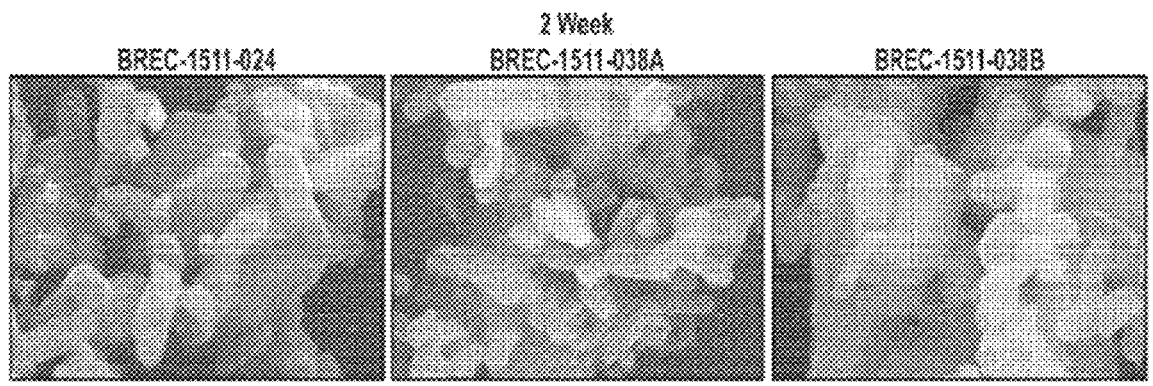

Particle morphology was determined by scanning electron microscopy (FIG. 12). As shown in FIG. 12, some degree of particle fusion was observed in all 3 samples.

Potency/Purity of the Formulation

Figure 13:
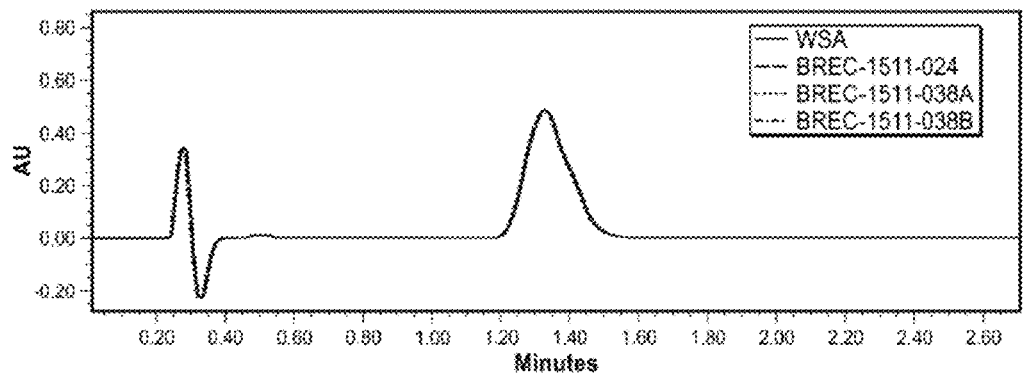
FIG. 13 is a summary of RP-HPLC results of BREC1511-024, BREC1511-038A, and BREC1511-038B after 2 weeks at 50° C./75% RH.

Aspirin is in many pharmacopoeia which recommends a titrimetric method and HPLC for its analysis (British Pharmacopoeia. Vol 1. London: Her Majesty's Stationary Office; 2009. pp. 442-5: The United States Pharmacopoeia. Vol. 30. Rockville: U.S. Pharmacopoeial Convention Inc; 2008. p. 1164: Patel et al. *Indian J Pharm Sci.* 75(4): 413-419 (2013)). Using the reversed-phase high-performance liquid chromatography (RP-HPLC) method, degradation studies were performed on each compound formulation after the 2-week storage period. The chromatogram showing the peak purity of each compound formulation by UV (FIG. 13) demonstrates the lack of significant degradants after 2 weeks. Furthermore, potency of each of the 3 compound formulations is preserved after 2 weeks of incubation (50° C./75% RH) (Table 28).

TABLE 28

No significant loss of potency is observed after 2 weeks at 50° C./75% RH

| Lot | Approach | Formulation (w/w %) | Initial Assay | 2 Week Assay (ASA) |
|---|---|---|---|---|
| BREC-1511-024 | Jet Milled | 100% ASA | | 100.5% ± 0.5 |
| BREC-1511-038A | Suspend milled ASA in hexane | 100% ASA | 101.3% ± 0.9 | 100.4% ± 0.8 |
| BREC-1511-038B | | 99.9/0.1 ASA/Lecithin | 101.1% ± 0.4 | 100.1% ± 0.7 |

Particle Size Distribution

Next, particle size distribution using Malvern particle size analyzer was performed to characterize the formulation before and after the 2 week period. Average D(0.1), D(0.5) and D(0.9), D[3, 2], and D[4,3] values for BREC1511-024, BREC1511-038A, and BREC1511-038B are shown in Table 29.

TABLE 29

Particle Size Distribution

| Lot | D(v 0.1) µm | D(v 0.5) µm | D(v 0.9) µm | D[3, 2] µm | D[4, 3] µm | Span |
|---|---|---|---|---|---|---|
| BREC-1511-024 (T = 0 wk) | 0.6 | 1.5 | 3.0 | 1.2 | 1.7 | 1.597 |
| BREC-1511-024 (T = 2 wk) | 0.8 | 3.4 | 9.0 | 1.9 | 4.3 | 2.401 |
| BREC-1511-038A (T = 0 wk) | 0.9 | 2.3 | 4.5 | 1.6 | 2.5 | 1.592 |
| BREC-1511-038A (T = 2 wk) | 1.1 | 2.9 | 6.0 | 2.0 | 3.3 | 1.720 |
| BREC-1511-038B (T = 0 wk) | 0.9 | 2.0 | 3.9 | 1.6 | 2.2 | 1.487 |
| BREG-1511-038B (T = 2 wk) | 1.0 | 3.8 | 9.2 | 2.1 | 4.6 | 2.171 |

As illustrated in Table 29 and FIG. 14, all 3 compound formulations showed an increase in particle size after the 2-week storage period. While the particle size of milled ASA spray dried with lecithin was slightly smaller compared to ASA alone, the change in particle size from week 0 to week 2 was greater for BREC-1511-038B then BREC-1511-038A.

Aerosol Performance

The aerodynamic particle size distributions of BREC1511-024, BREC1511-038A, and BREC1511-038B were determined according to the following: for each compound formulation, a single capsule was filled with 37 mg of formulated aspirin, and loaded into a low resistance device. Material was actuated at 60 L/min for 4 seconds. Particle size distributions at week 0 and week 2 were compared determining mass median aerodynamic diameter (MMAD), geometric standard deviation (GSD), emitted fraction (EF), and fine particle fraction (FPF)<5 micron. FIGS. 21-23 illustrate deposition profile of each aspirin formulation before and after the 2-week period in the next-generation impactor following aerosolization, where y axis=deposited fraction (% recovered dose)).

While BREC1511-024 (FIG. 15) and BREC-1511-038B (FIG. 17) displayed shifts in aerosol properties after 2 weeks, BREC1511-038A showed the smallest change of the 3 formulations (FIG. 16).

Example 11

Process Optimization

Figure 18:
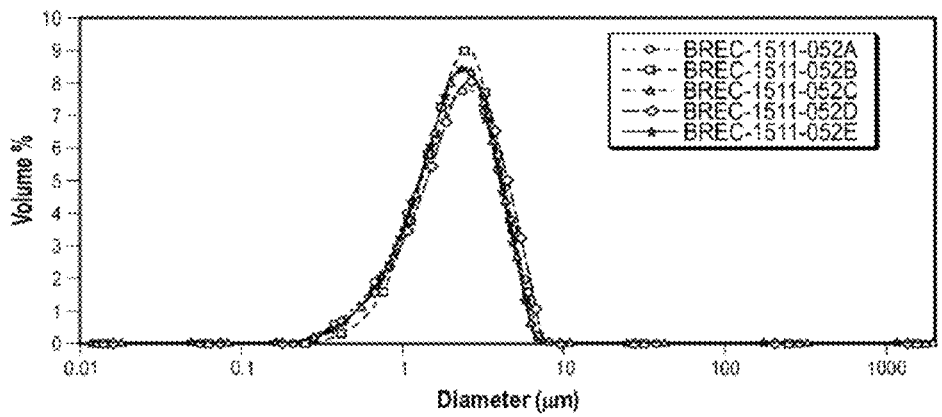
FIG. 18 shows laser diffraction data for (BREC-1511-052A). Spray Dried 100% Jet Milled ASA (High Flow) (BREC-1511-052B), Spray Dried 100% Jet Milled ASA (High Flow, High Solids)(BREC-1511-052C), Spray Dried 100% Jet Milled ASA (High Flow, High Solids, High Tout)(BREC-1511-052D), and Spray Dried 99.9/0.1 Jet Milled ASA/Lecithin (High Flow)(BREC-1511-052E).
Figure 20:
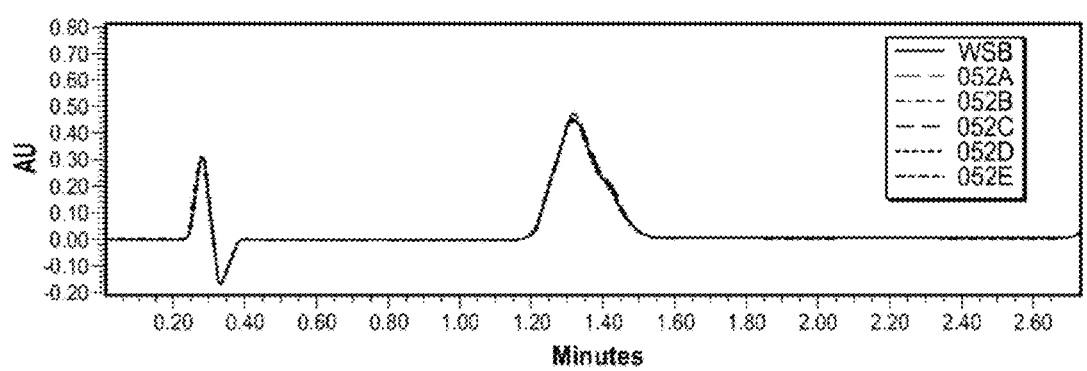
FIG. 20 shows powder characteristics for each batch (BREC-1511-052A, BREC-1511-052B, BREC-1511-052C, BREC-1511-052D, and BREC-1511-052E).

In the next set of experiments, the optimization of suspension spray drying process was conducted, with the goal of evaluating options for increasing throughput of hexane formulations by increasing suspension flow rate and/or increasing suspension concentration. 5 batches of spray-dried ASA suspension were manufactured on a PSD-1 scale spray dryer at batch sizes up to 300 g using jet-milled ASA from a third party supplier. The following variables were evaluated: increased spray drying suspension feed rate and increased solids concentration in suspension. These included the following formulations: Spray Dried 100% Jet Milled ASA (BREC-1511-052A), Spray Dried 100% Jet Milled ASA (High Flow)(BREC-1511-052B), Spray Dried 100% Jet Milled ASA (High Flow, High Solids)(BREC-1511-052C), Spray Dried 100% Jet Milled ASA (High Flow, High Solids, High Tout)(BREC-1511-052D), and Spray Dried 99.9/0.1 Jet Milled ASA/Lecithin (High Flow)(BREC-1511-052E). The goal was to evaluate the feasibility of spray drying batches with higher solids (BREC-1511-052C) and flow rate (BREC-1511-052B). Table 30 provides a summary of manufacturing characteristics. As shown in FIG. 18, all processing conditions produced particles of similar size and within the inhalable range. Furthermore, particle morphology was similar for all five batches (FIG. 19).

Further characterization of powder demonstrated that all samples have similar properties. No measurable amount of residual hexane or water was found in powder. Moreover, potency was within the expected range (FIG. 20).

Finally, time course of stability of each of the five batches described in this example at 5 days and 50° C. was studied. The summary of these findings is depicted in Table 31. Each of the five batches exhibited excellent stability under these conditions.

TABLE 30

| Manufacturing Summary | | | | | |
|---|---|---|---|---|---|
| Spray Reference (BREC-1511) | -052A (Control) | -052B (High Liquid Flow Rate) | -052C (High Solids) | -052D (High Tout) | -052E (Lecithin "control") |
| Formulation | 100% ASA | | | | 99.9/0.1 ASA/Lecithin |
| Anti-Solvent | Hexane | | | | |
| Solids Content | 2 | 2 | 15 | 15 | 2 |
| Batch Size | 300 | | | | |
| Nozzle | 1650/120 LC/AC | 2850/120 LC/AC | | | |
| Atomization Pressure [psi] | 40 | 50 | | | |
| Flowrate [g/min] | 30 | 150 | 150 | 150 | 150 |
| Drying Gas [g/min] | 1250 | | | | |
| Inlet Temperature [° C.] | 100 | 155 | 155 | 196 | 145 |
| Outlet T emperature [° C.] | 60 | 60 | 60 | 78 | 60 |
| Yield | 58 | 56 | 65 | 74 | 69 |

TABLE 31

| Particle Size Stability after 5 days (50 C.) | | | | | | | |
|---|---|---|---|---|---|---|---|
| Lot Number | Sample Description | Storage Condition | D(v 0.1) μm | D(v 0.5) μm | D(v 0.9) μm | D[3, 2] μm | D[4, 3] μm |
| JP Non-Refrigerated Lot | 100% Jet Milled ASA (Initial) | Initial | 0.7 | 1.7 | 3.4 | 1.3 | 1.9 |
| | 100% Jet Milled ASA (5 days, 50° C.) | 5 days, 50° C. | 0.8 | 2.6 | 5.9 | 1.7 | 3.0 |
| JP Refrigerated Lot | 100% Jet Milled ASA (Initial) | Initial | 0.7 | 1.9 | 3.7 | 1.4 | 2.1 |
| | 100% Jet Milled ASA (5 days, 50° C.) | 5 days, 50° C. | 0.8 | 2.7 | 5.8 | 1.7 | 3.1 |
| BREC-1511-052A | Spray Dried 100% Jet Milled ASA (Initial, Baseline) | Initial | 0.8 | 2.0 | 4.0 | 1.4 | 2.2 |
| | Spray Dried 100% Jet Milled ASA (5 days, 50° C., Baseline) | 5 days, 50° C. | 0.9 | 2.6 | 5.3 | 1.8 | 2.9 |
| BREC-1511-052B | Spray Dried 100% Jet Milled ASA (Initial, High Flow) | Initial | 0.9 | 2.1 | 3.9 | 1.7 | 2.3 |
| | Spray Dried 100% Jet Milled ASA (5 days, 50° C., High Flow) | 5 days, 50° C. | 1.0 | 2.6 | 5.2 | 1.8 | 2.9 |
| BREC-1511-052C | Spray Dried 100% Jet Milled ASA (Initial, High Flow) High Solids) | Initial | 0.8 | 2.0 | 3.8 | 1.5 | 2.2 |
| | Spray Dried 100% Jet Milled ASA (5 days, 50° C., High Flow, High Solids) | 5 days, 50° C. | 0.9 | 2.5 | 5.2 | 1.8 | 2.8 |
| BREC-1511-052D | Spray Dried 100% Jet Milled ASA (Initial, High Flow) High Solids, High Tout) | Initial | 0.8 | 2.2 | 4.3 | 1.6 | 2.4 |
| | Spray Dried 100% Jet Milled ASA (5 days, 50° C., | 5 days, 50° C. | 0.9 | 2.7 | 5.4 | 1.8 | 3.0 |

TABLE 31-continued

Particle Size Stability after 5 days (50 C.)

| Lot Number | Sample Description | Storage Condition | D(v 0.1) μm | D(v 0.5) μm | D(v 0.9) μm | D[3, 2] μm | D[4, 3] μm |
|---|---|---|---|---|---|---|---|
| BREC 1511-052E | High Flow, High Solids, High Tout) Spray Dried 99.9/0.1 Jet Milled ASA/Lecithin (Initial, High Flow) | Initial | 0.8 | 1.9 | 3.8 | 1.5 | 2.1 |
|  | Spray Dried 99.9/0.1 Jet Milled ASA/Lecithin (5 days, 50° C., High Flow) | 5 days, 50° C. | 1.0 | 2.8 | 5.8 | 1.9 | 3.1 |

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

It is to be understood that, while the subject technology has been described in conjunction with the detailed description, thereof, the foregoing description is intended to illustrate and not limit the scope of the subject technology. The citation of any references herein is not an admission that such references are prior art to the present invention.

Those skilled in the art will recognize, or be able to ascertain using no more than routine experimentation, many equivalents to the specific embodiments of the invention described herein. Such equivalents are intended to be encompassed by the following embodiments.

The invention claimed is:

1. A drug delivery system comprising a dry powder, the dry powder comprising a non-steroidal anti-inflammatory drug (NSAID), a pharmaceutically acceptable excipient and having an emitted dose from 70% to 95%;
wherein
the NSAID is 50% w/w or more of the dry powder,
the pharmaceutically acceptable excipient is 0.01% w/w to 10% w/w of the dry powder, and
the dry powder has a particle size distribution with a DV50 in a range of 3 μm to 6.7 μm and a DV10 in a range of 0.9 μm to 3.3 μm.

2. The drug delivery system according to claim 1, wherein the emitted dose is from 75% to 95%.

3. The drug delivery drug delivery system according to claim 1, wherein the NSAID is a salicylate.

4. The drug delivery system according to claim 1, wherein the NSAID is acetylsalicylic acid or a pharmaceutically acceptable salt thereof.

5. The drug delivery system according to claim 1, wherein the dry powder has a mass median aerodynamic diameter (MMAD) within a range of about 0.5 μm to about 10 μm.

6. The drug delivery system according to claim 1, wherein the NSAID is 90% (w/w) or more of the dry powder.

7. The drug delivery system according to claim 1, wherein the pharmaceutically acceptable excipient is 0.01% (w/w) to 4% (w/w) of the dry powder.

8. The drug delivery system according to claim 1, wherein the pharmaceutically acceptable excipient comprises one or more surfactants.

9. The drug delivery system according to claim 1, wherein the pharmaceutically acceptable excipient comprises one or more phospholipids.

10. The drug delivery system according to claim 1, further comprising a dry powder inhaler,
wherein the dry powder inhaler comprises a mouthpiece, a reservoir for receiving the respirable dry powder, and an actuation member for making available the respirable dry powder.

11. The drug delivery system according to claim 1, wherein the NSAID is present in a dose of less than 81 mg.

12. The drug delivery system according to claim 1, wherein the dry powder further comprises clopidogrel.

13. The drug delivery system according to claim 5, wherein the MMAD varies less than about 30% after the dry powder is stored at 30° C. at 65% relative humidity for about 4 weeks.

14. The drug delivery system according to claim 5, wherein the MMAD varies less than about 30% after the dry powder is stored at 50° C. at 75% relative humidity for about 2 weeks.

15. The drug delivery system according to claim 5, wherein the MMAD varies less than about 10% after the dry powder is stored at 50° C. for about 5 days.

16. A method of preventing or treating a thromboembolic event in a subject in need thereof using the drug delivery system of claim 1.

* * * * *